United States Patent
Khalid et al.

(10) Patent No.: US 11,596,482 B2
(45) Date of Patent: Mar. 7, 2023

(54) SYSTEM AND METHOD FOR SURGICAL PERFORMANCE TRACKING AND MEASUREMENT

(71) Applicant: SURGICAL SAFETY TECHNOLOGIES INC., Toronto (CA)

(72) Inventors: Shuja Khalid, Toronto (CA); Mitchell Geoffrey Goldenberg, Toronto (CA); Teodor Pantchev Grantcharov, Stouffville (CA); Babak Taati, Toronto (CA); Frank Rudzicz, Toronto (CA)

(73) Assignee: SURGICAL SAFETY TECHNOLOGIES INC., Toronto (CA)

( * ) Notice: Subject to any disclaimer, the term of this patent is extended or adjusted under 35 U.S.C. 154(b) by 379 days.

(21) Appl. No.: 16/881,906

(22) Filed: May 22, 2020

(65) Prior Publication Data

US 2020/0367974 A1    Nov. 26, 2020

Related U.S. Application Data

(60) Provisional application No. 62/852,054, filed on May 23, 2019.

(51) Int. Cl.
*G05B 13/02* (2006.01)
*A61B 34/20* (2016.01)
(Continued)

(52) U.S. Cl.
CPC .............. *A61B 34/20* (2016.02); *A61B 34/25* (2016.02); *G06K 9/6256* (2013.01); *G06N 3/063* (2013.01);
(Continued)

(58) Field of Classification Search
CPC .... G06N 3/063; G06N 3/0454; G06N 3/0445; G06N 3/08; G06N 20/00; A61B 34/25;
(Continued)

(56) References Cited

U.S. PATENT DOCUMENTS 11,116,587 B2 *  9/2021  Wolf ....................... G06F 3/048
2020/0337776 A1 * 10/2020  Saun ........................ G06T 1/60

OTHER PUBLICATIONS

Niitsu H, Hirabayashi N, Yoshimitsu M, et al. Using the Objective Structured Assessment of Technical Skills (OSATS) global rating scale to evaluate the skills of surgical trainees in the operating room. Surg Today. 2013;43(3):271-275. doi:10.1007/s00595-012-0313-7.

(Continued)

*Primary Examiner* — Robert Chevalier
(74) *Attorney, Agent, or Firm* — Norton Rose Fulbright Canada LLP

(57) ABSTRACT

Computer implemented methods and systems are provided for training a machine learning architecture for surgical performance tracking and measurement based on surgical procedure video data set. The methods and systems include, in a first aspect, a sequential relation architecture and a dimensionality reduction architecture. In a second aspect, the methods and systems include a surgical instrument instance segmentation architecture, a decomposition model, and a sequential relation architecture. The video data is processed on a frame level to generate compressed or reduced representations of the video data.

20 Claims, 34 Drawing Sheets

(51) Int. Cl.
*G06N 20/00* (2019.01)
*G06N 3/063* (2023.01)
*A61B 34/00* (2016.01)
*H04N 19/54* (2014.01)
*G06K 9/62* (2022.01)
*G06V 20/40* (2022.01)

(52) U.S. Cl.
CPC ............. *G06N 20/00* (2019.01); *G06V 20/46* (2022.01); *H04N 19/54* (2014.11)

(58) Field of Classification Search
CPC . A61B 34/20; A61B 90/361; A61B 2034/102; G06V 20/46; G06V 10/82; G06K 9/6256; G06K 9/6271; H04N 19/54
USPC ............................ 700/48, 47, 28, 52, 30, 31
See application file for complete search history.

(56) References Cited

OTHER PUBLICATIONS

Tsung-Yi Lin, Michael Maire, Serge Belongie, James Hays, Pietro Perona, Deva Ramanan, Piotr Dollar, and C Lawrence Zitnick. Microsoft coco: Common objects in context. In European conference on computer vision, pp. 740-755. Springer, 2014.

Martin JA, Regehr G, Reznick R, et al. Objective Structured Assessment of Technical Skill (OSATS) for surgical residents. Br J Surg 1997;84(2):273-278. doi:10.1002/bjs.1800840237.

Hatala R, Cook DA, Brydges R, Hawkins R. Constructing a validity argument for the Objective Structured Assessment of Technical Skills (OSATS): a systematic review of validity evidence. Adv Health Sci Educ Theory Pract. 2015;20(5):1149-1175. doi: 10.1007/s10459-015-9593-1.

Lea C, Reiter A, Vidal R, Hager GD. Segmental spatiotemporal CNNs for fine-grained action segmentation. Accessed Feb. 25, 2020. https://arxiv.org/abs/1602.02995.

Gao Y, Swaroop Vedula S, Reiley CE, et al. JHU-ISI Gesture and Skill Assessment Working Set (JIGSAWS): a surgical activity dataset for human motion modeling. Accessed Feb. 25, 2020. https://cirl.lcsr.jhu.edu/wpcontent/uploads/2015/11/JIGSAWS.pdf.

Ituitive Surgical. DaVinci by Intuitive. Accessed Feb. 25, 2020. https://www.intuitive.com/en-us/productsand-services/da-vinci.

DiPietro R, Lea C, Malpani A, et al. Recognizing surgical activities with recurrent neural networks. Accessed Feb. 25, 2020. https://arxiv.org/abs/1606.06329.

Sarikaya D, Jannin P. Surgical gesture recognition with optical flow only. Accessed Feb. 25, 2020. https://arxiv.org/abs/1904.01143.

Diederik P Kingma and Jimmy Ba. Adam: A method for stochastic optimization. arXiv preprint arXiv:1412.6980, 2014.

Vincent P, Larochelle H, Bengio Y, Manzagol P-A. Extracting and composing robust features with denoising autoencoders. Accessed Feb. 25, 2020. https://www.cs.toronto.edu/~larocheh/publications/icml-2008-denoising-autoencoders.pdf.

Tung H-YF, Tung H-W, Yumer E, Fragkiadaki K. Self-supervised learning of motion capture. Accessed Feb. 25, 2020. https://arxiv.org/abs/1712.01337.

He K, Gkioxari G, Dollár P, Girshick R. Mask R-CNN. Accessed Feb. 25, 2020. https://arxiv.org/abs/1703.06870.

Hassan Ismail Fawaz, Germain Forestier, Jonathan Weber, Lhassane Idoumghar, and Pierre-Alain Muller. Evaluating surgical skills from kinematic data using convolutional neural networks. arXiv preprint arXiv:1806.02750, 2018.

Tao L, Zappella L, Hager GD, Vidal R. Surgical gesture segmentation and recognition. Med Image Comput Assist Interv. 2013;16(Pt 3):339-346.

Sefati S, Cowan NJ, Vidal R. Learning shared, discriminative dictionaries for surgical gesture segmentation and classification. Accessed Feb. 25, 2020. http://www.vision.jhu.edu/assets/SefatiM2CAI15.pdf.

Forestier G, Petitjean F, Senin P, et al. Surgical motion analysis using discriminative interpretable patterns. Artif Intell Med. 2018;91:3-11. doi:10.1016/j.artmed.2018.08.002.

Liu D, Jiang T. Deep reinforcement learning for surgical gesture segmentation and classification. Accessed Feb. 25, 2020. https://arxiv.org/abs/1806.08089.

Wang Z, Fey AM. Deep learning with convolutional neural network for objective skill evaluation in robotassisted surgery. Accessed Feb. 25, 2020. https://arxiv.org/abs/1806.05796.

Jin A, Yeung S, Jopling J, et al. Tool detection and operative skill assessment in surgical videos using region based convolutional neural networks. Accessed Feb. 25, 2020. https://arxiv.org/abs/1802.08774.

Girshick R. Fast R-CNN. Accessed Feb. 25, 2020. https://arxiv.org/abs/1504.08083.

Medical Image Computing and Computer Assisted Intervention Society. Tool presence detection challenge results. Accessed Feb. 25, 2020. http://camma.u-strasbg.fr/ m2cai2016/index.php/tool-presence-detection-challenge-results.

Wang Z, Fey AM. SATR-DL: improving surgical skill assessment and task recognition in robot-assisted surgery with deep neural networks. Accessed Feb. 25, 2020. https://arxiv.org/abs/1806.05798.

Hung AJ, Chen J, Che Z, et al. Utilizing machine learning and automated performance metrics to evaluate robot-assisted radical prostatectomy performance and predict outcomes. J Endourol. 2018;32(5):438-444. doi 10.1089/end.2018.0035.

Twinanda AP, Shehata S, Mutter D, Marescaux J, de Mathelin M, Padoy N. EndoNet: a deep architecture for recognition tasks on laparoscopic videos. Accessed Feb. 25, 2020. https://arxiv.org/abs/1602.03012.

Sahu M, Mukhopadhyay A, Szengel A, Zachow S. Tool and phase recognition using contextual CNN features. Accessed Feb. 25, 2020 https://arxiv.org/abs/1610.08854.

Waleed Abdulla. Mask r-cnn for object detection and instance segmentation on keras and tensorflow. https://github.com/matterport/Mask_RCNN, 2017.

David P Azari, Lane L Frasier, Sudha R Pavuluri Quamme, Caprice C Greenberg, Carla M Pugh, Jacob A Greenberg, and Robert G Radwin. Modeling surgical technical skill using expert assessment for automated 1omputer rating. Annals of surgery, 2017.

Shaojie Bai, J. Zico Kolter, and Vladlen Koltun. An empirical evaluation of generic convolutional and recurrent networks for sequence modeling. CoRR, abs/1803.01271, 2018. URL http://arxiv.org/abs/1803.01271.

Vassiliou MC, Feldman LS, Andrew CG, et al. A global assessment tool for evaluation of intraoperative laparoscopic skills. Am J Surg. 2005;190(1):107-113. doi:10.1016/j.amjsurg.2005.04.004.

Gao Y, Vedula SS, Lee GI, LeeMR, Khudanpur S, Hager GD. Query-by-example surgical activity detection. Int J Comput Assist Radiol Surg. 2016;11(6):987-996. doi:10.1007/s11548-016-1386-3.

Gurcan I, Nguyen HV. Surgical activities recognition using multi-scale recurrent networks. In: ICASSP 2019-2019 IEEE International Conference on Acoustics, Speech and Signal Processing (ICASSP). IEEE; 2019:2887-2891. doi:10.1109/ICASSP.2019.8683849.

* cited by examiner (a) Case 1

(b) Case 2

(c) Case 3

(d) Case 4

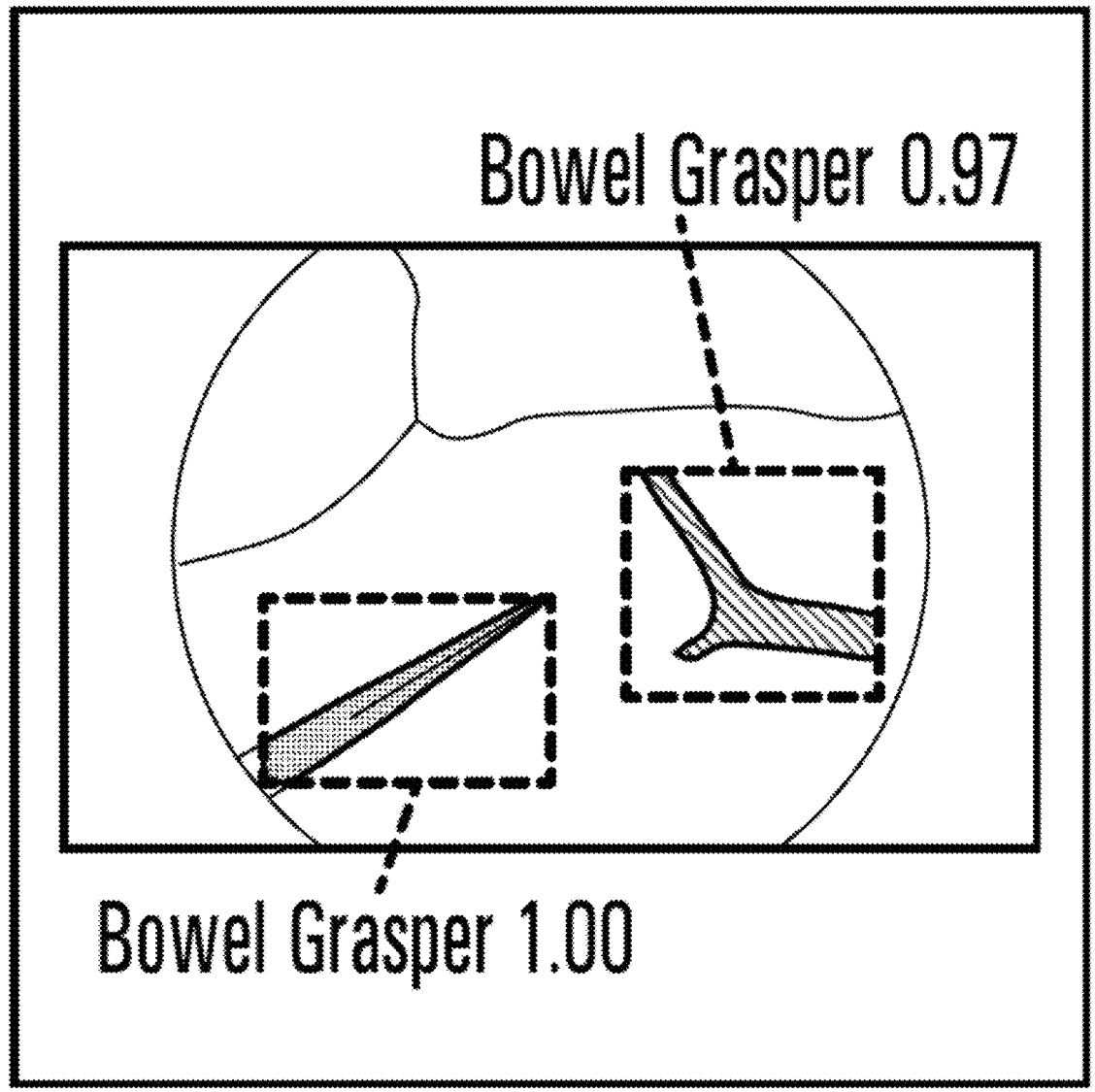
FIG. 11-AA

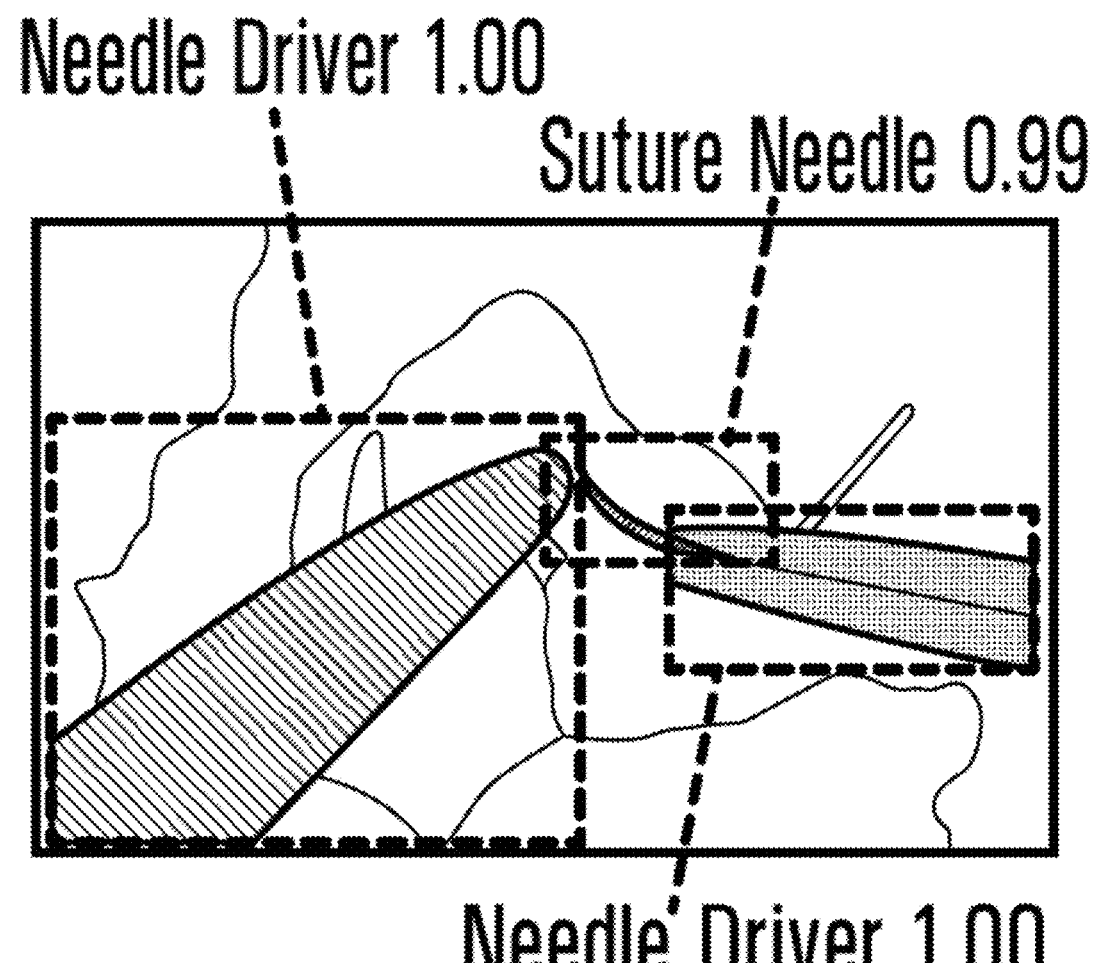
FIG. 11-AB

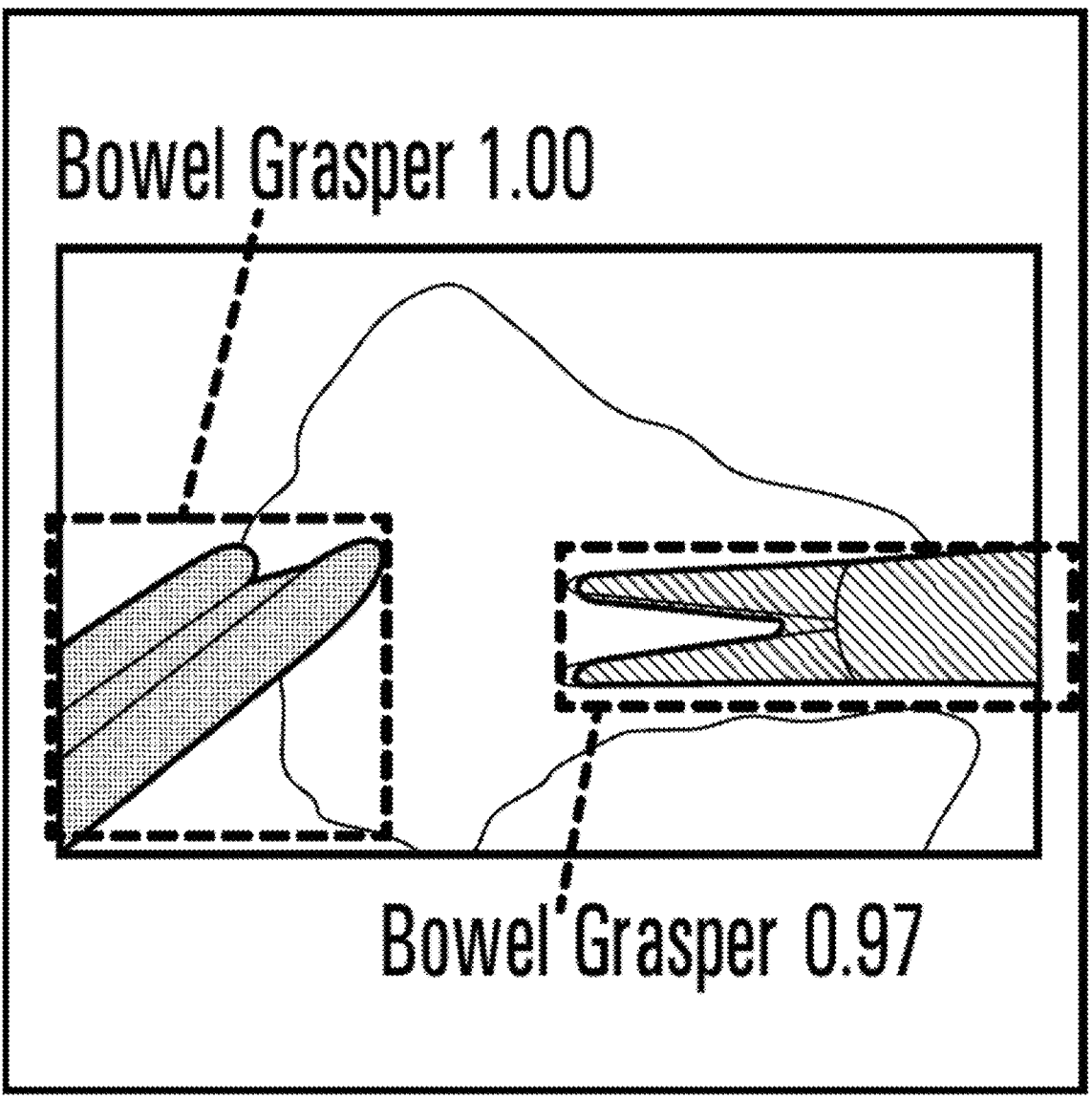
FIG. 11-AC

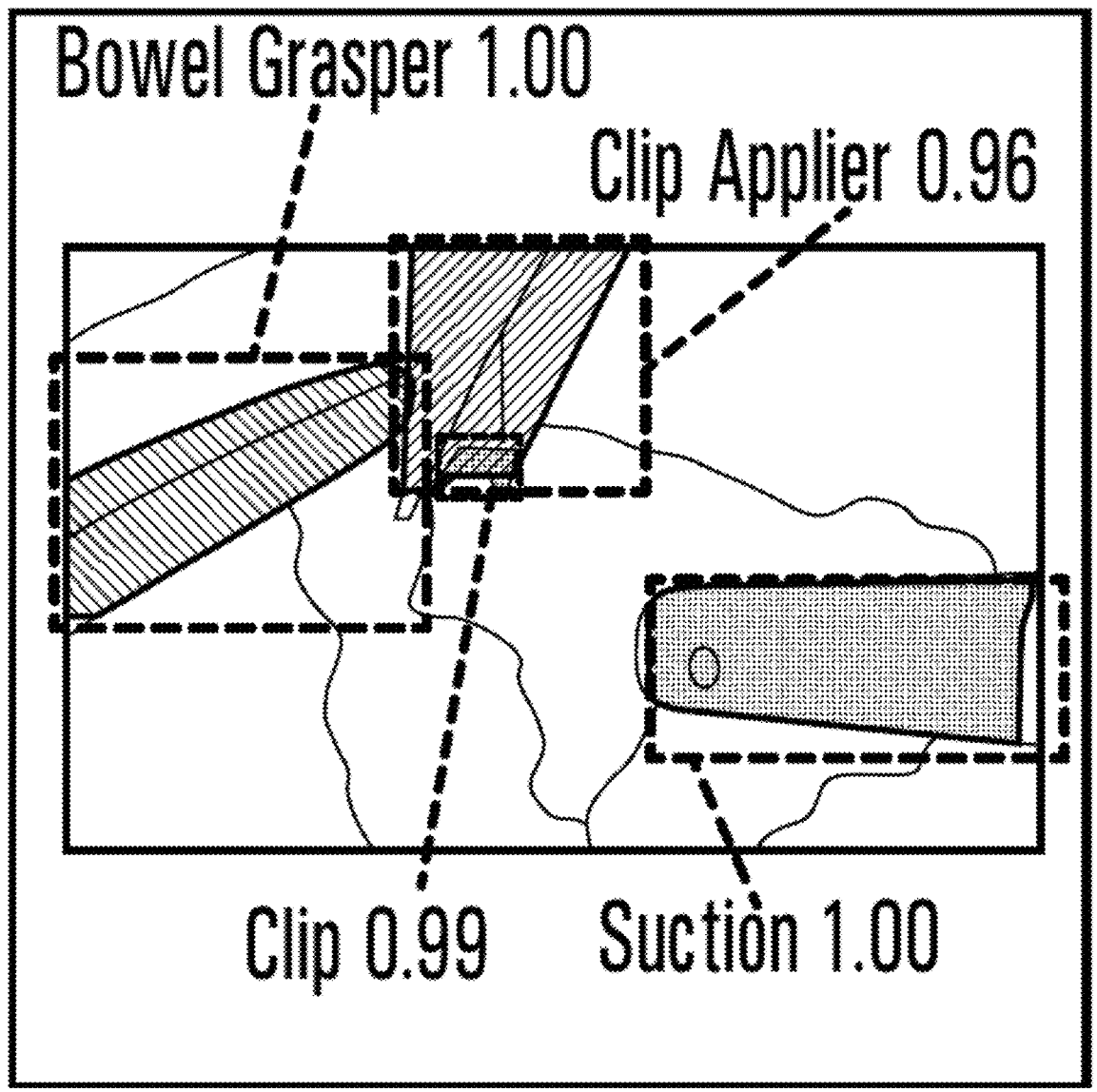
FIG. 11-AD

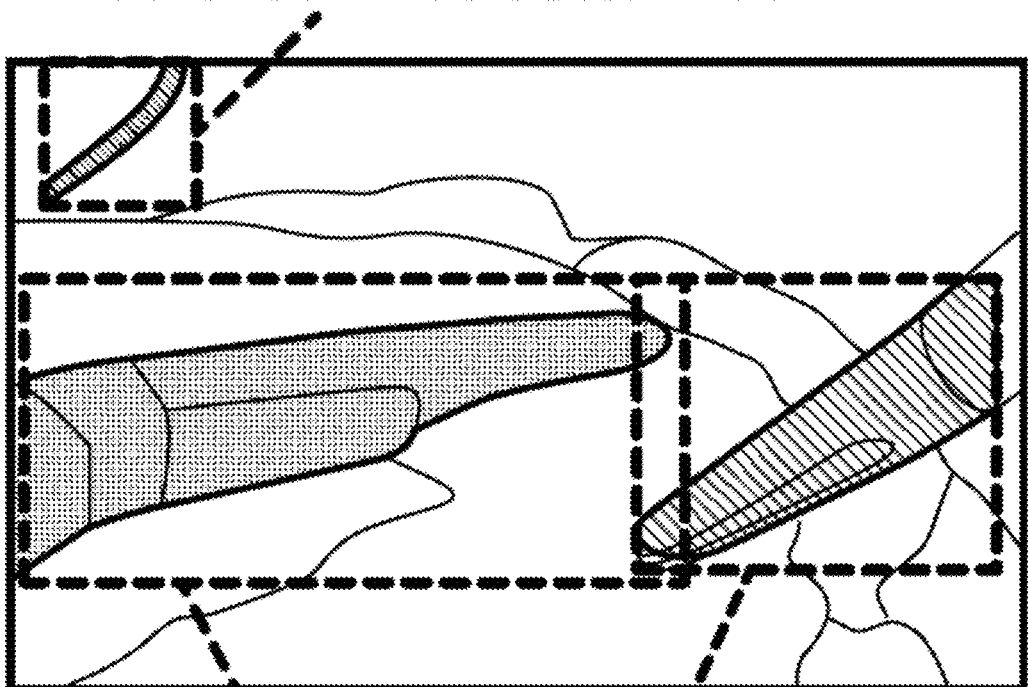
FIG. 11-AE

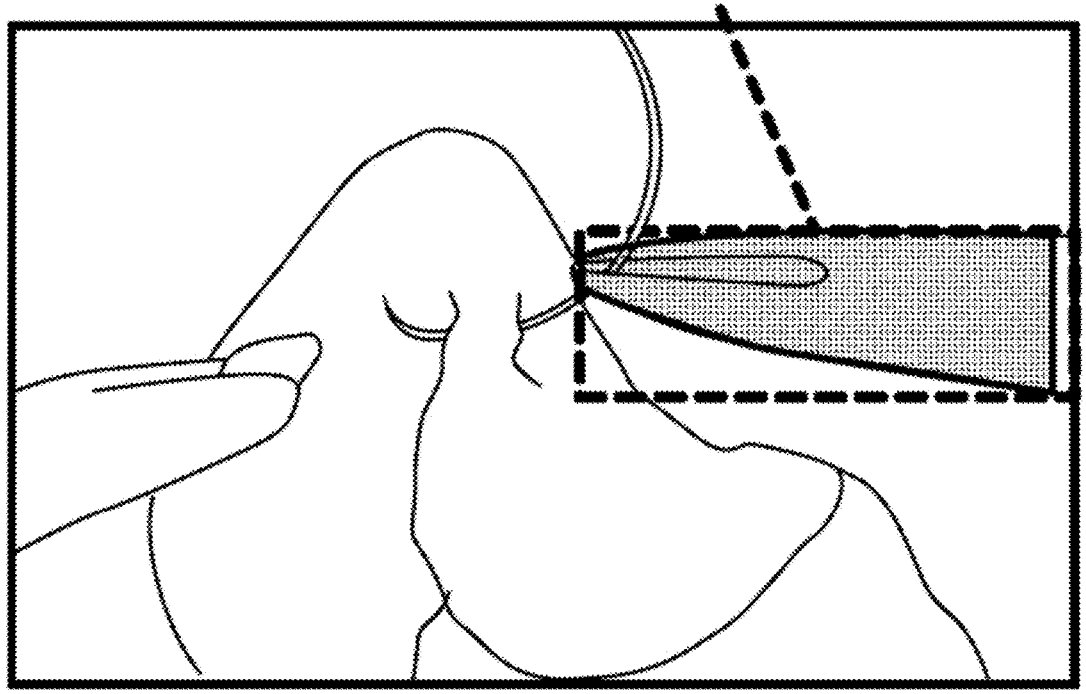
FIG. 11-AF

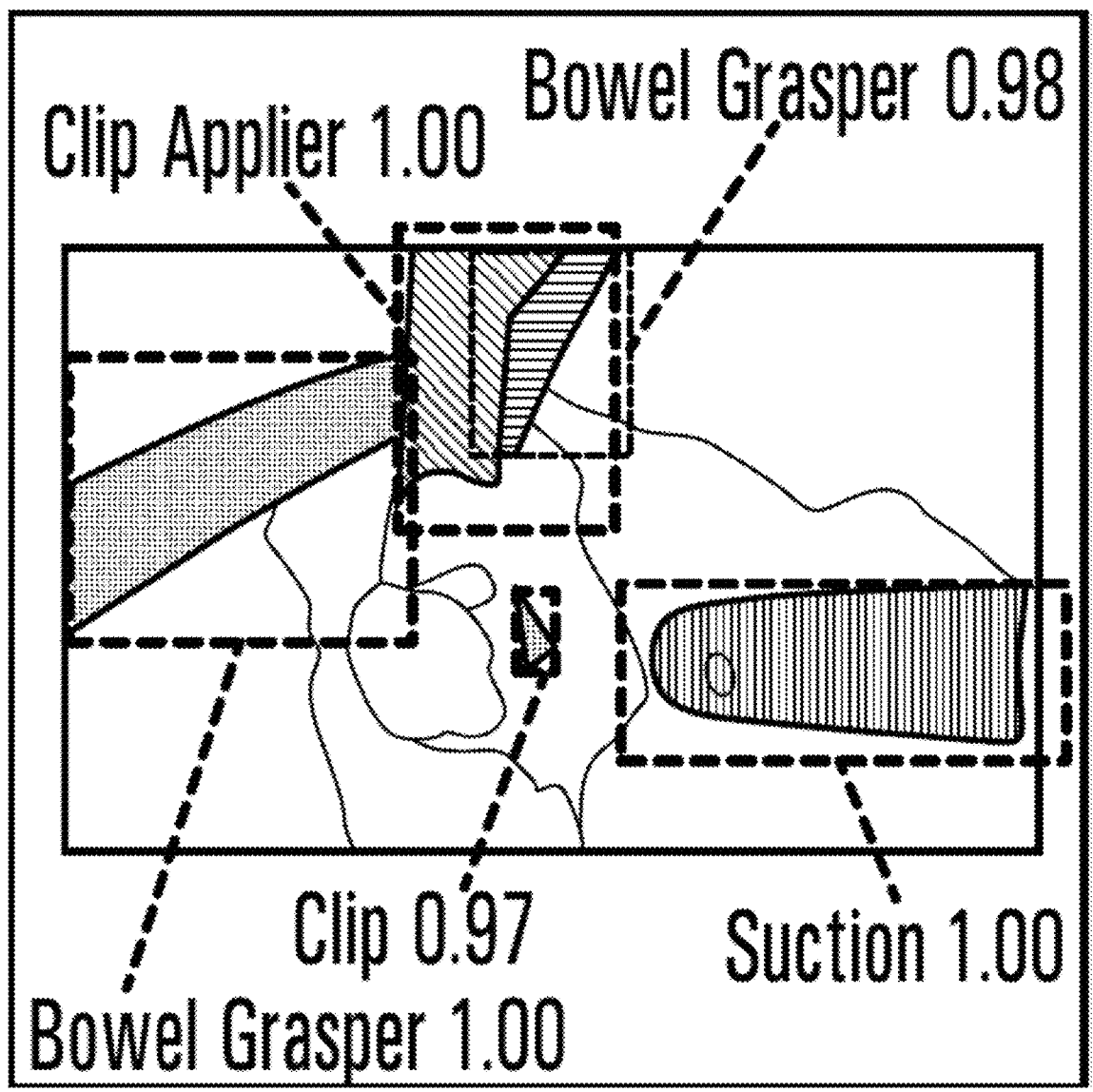
FIG. 11-AG

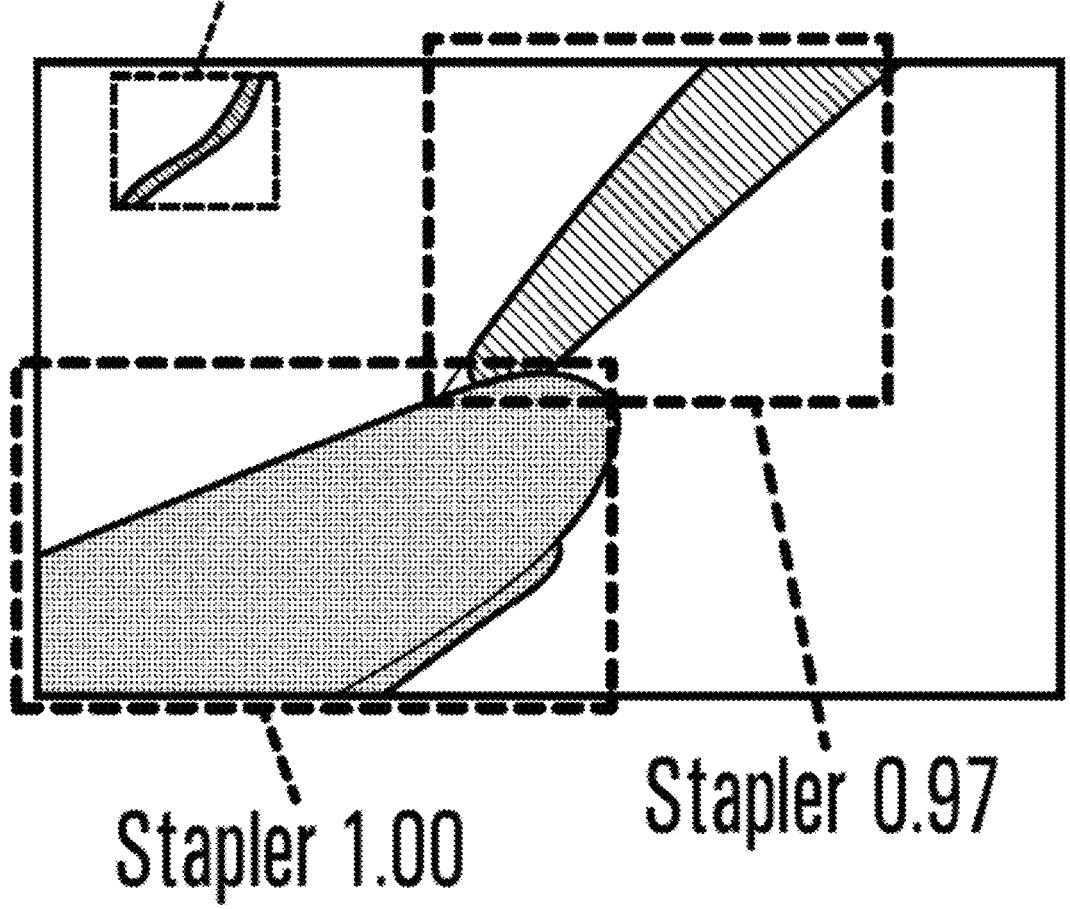
FIG. 11-AH

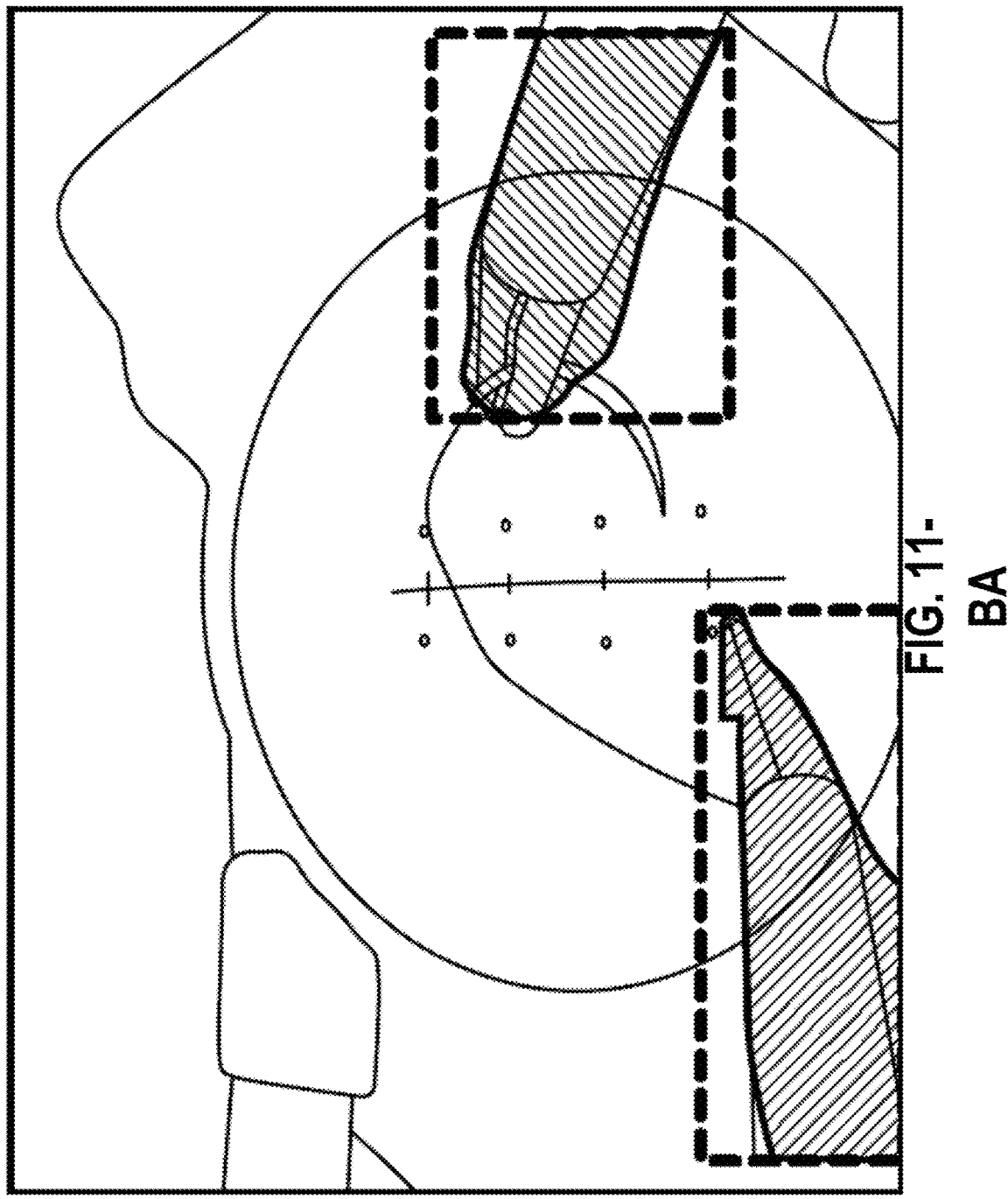
FIG. 11-BA

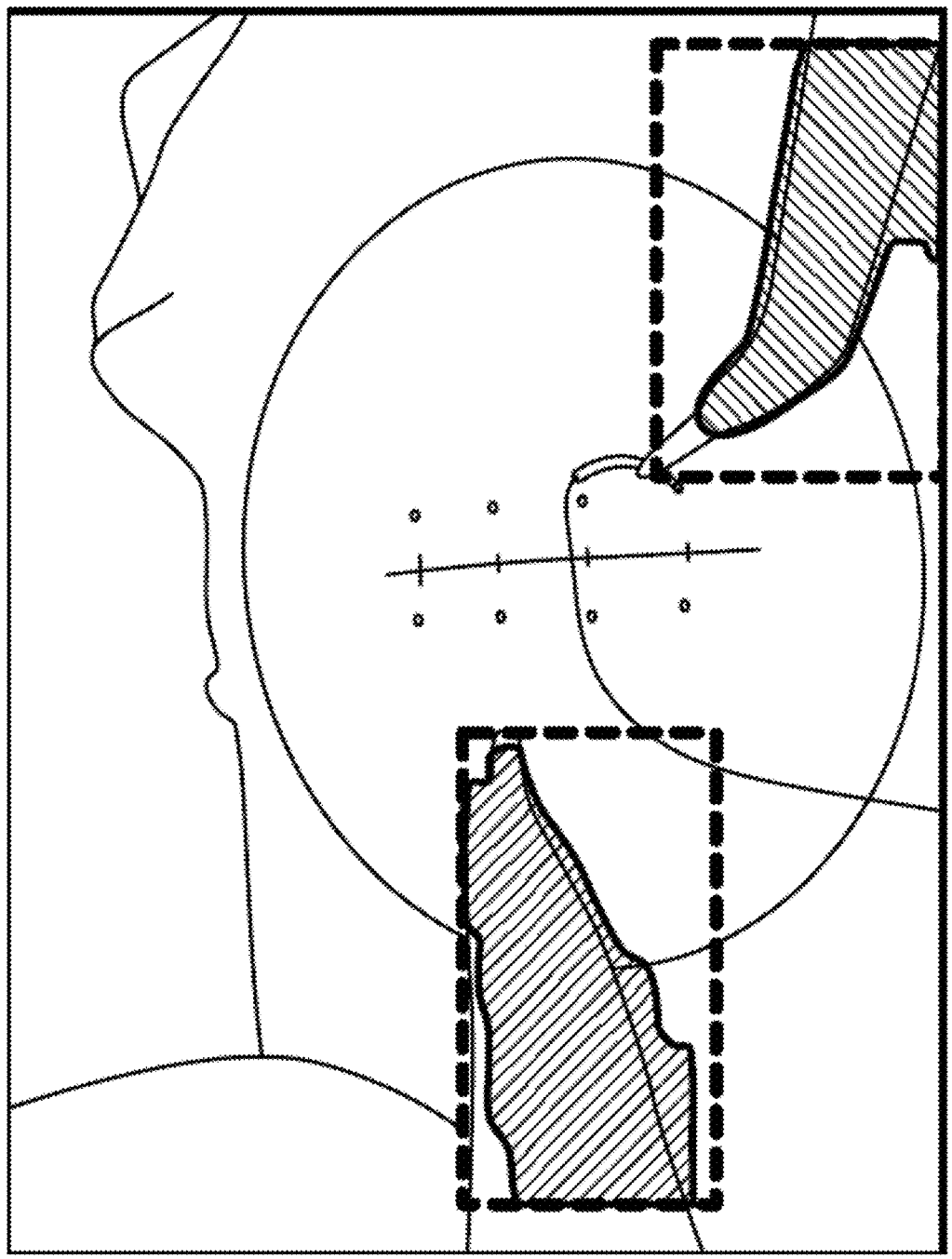
FIG. 11-BB

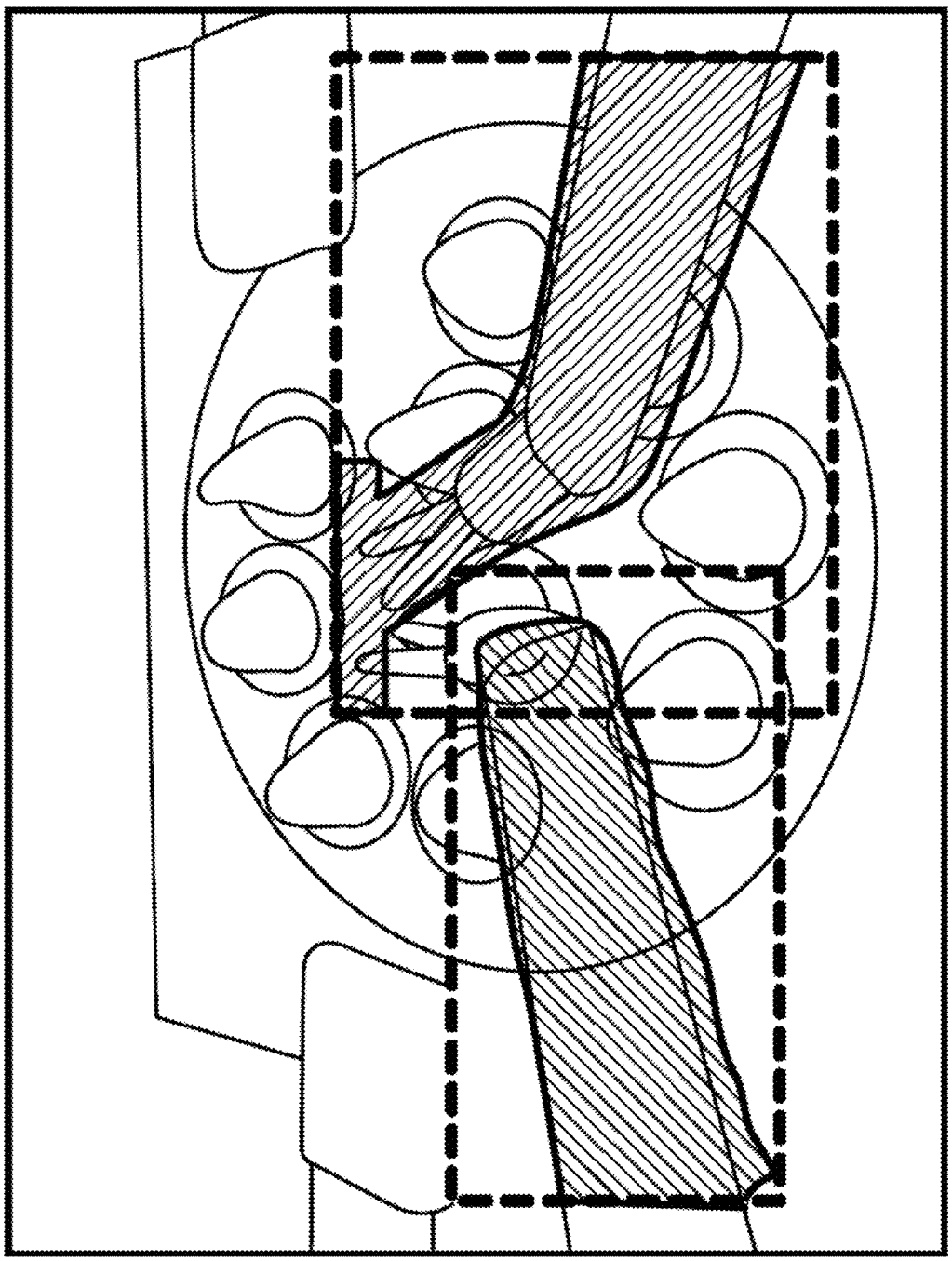
FIG. 11-BC

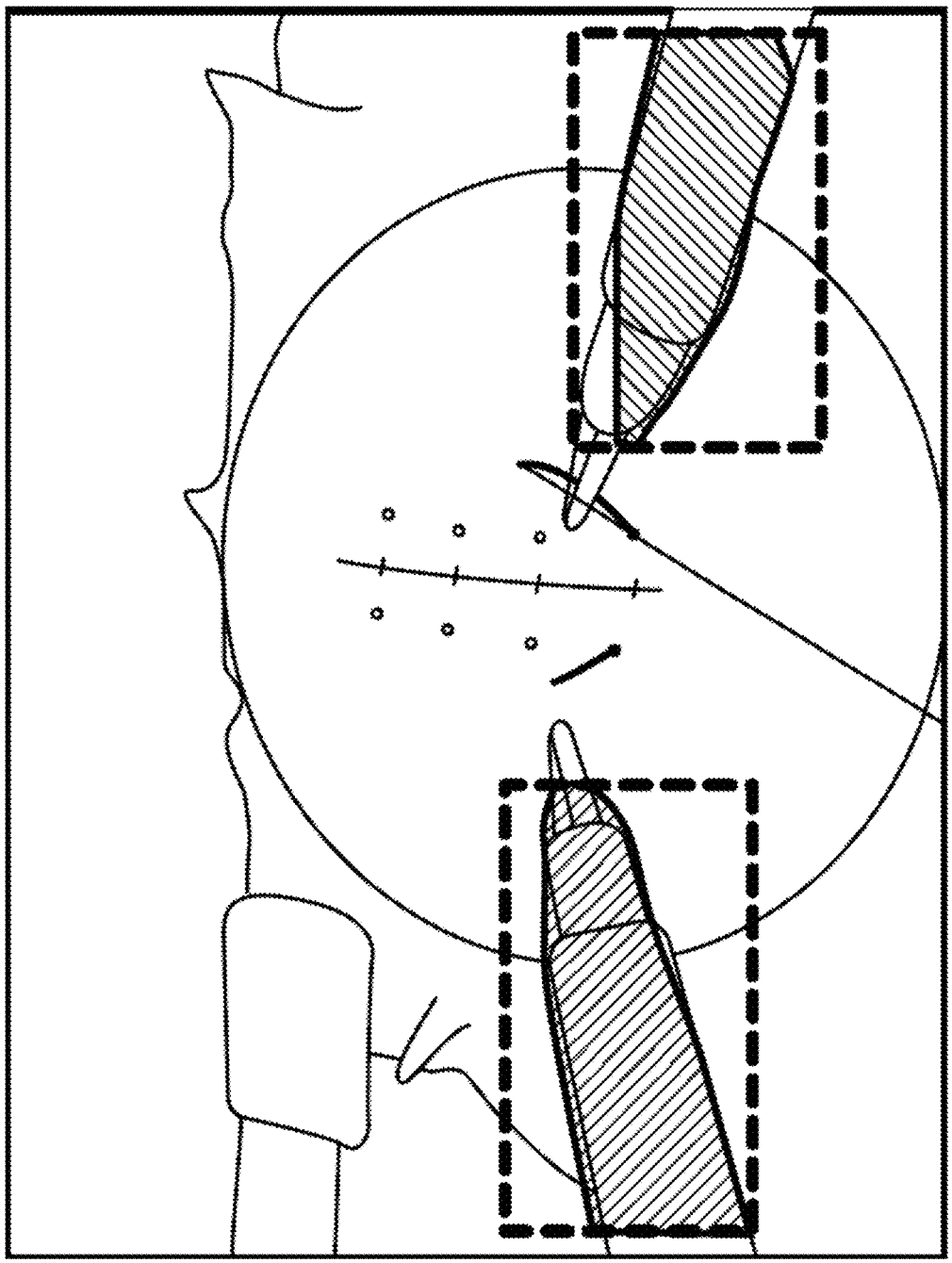
FIG. 11-BD

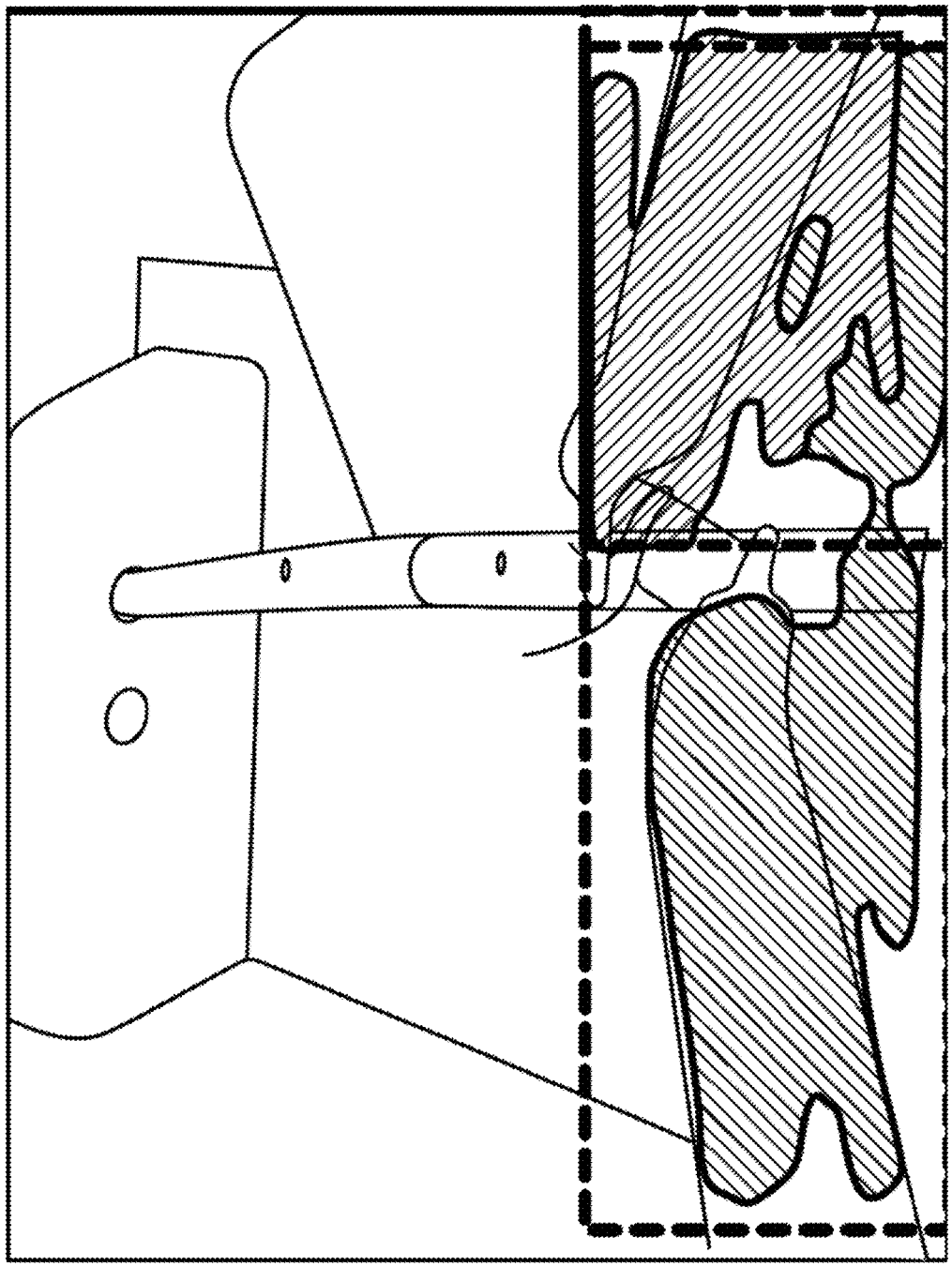
FIG. 11-BE

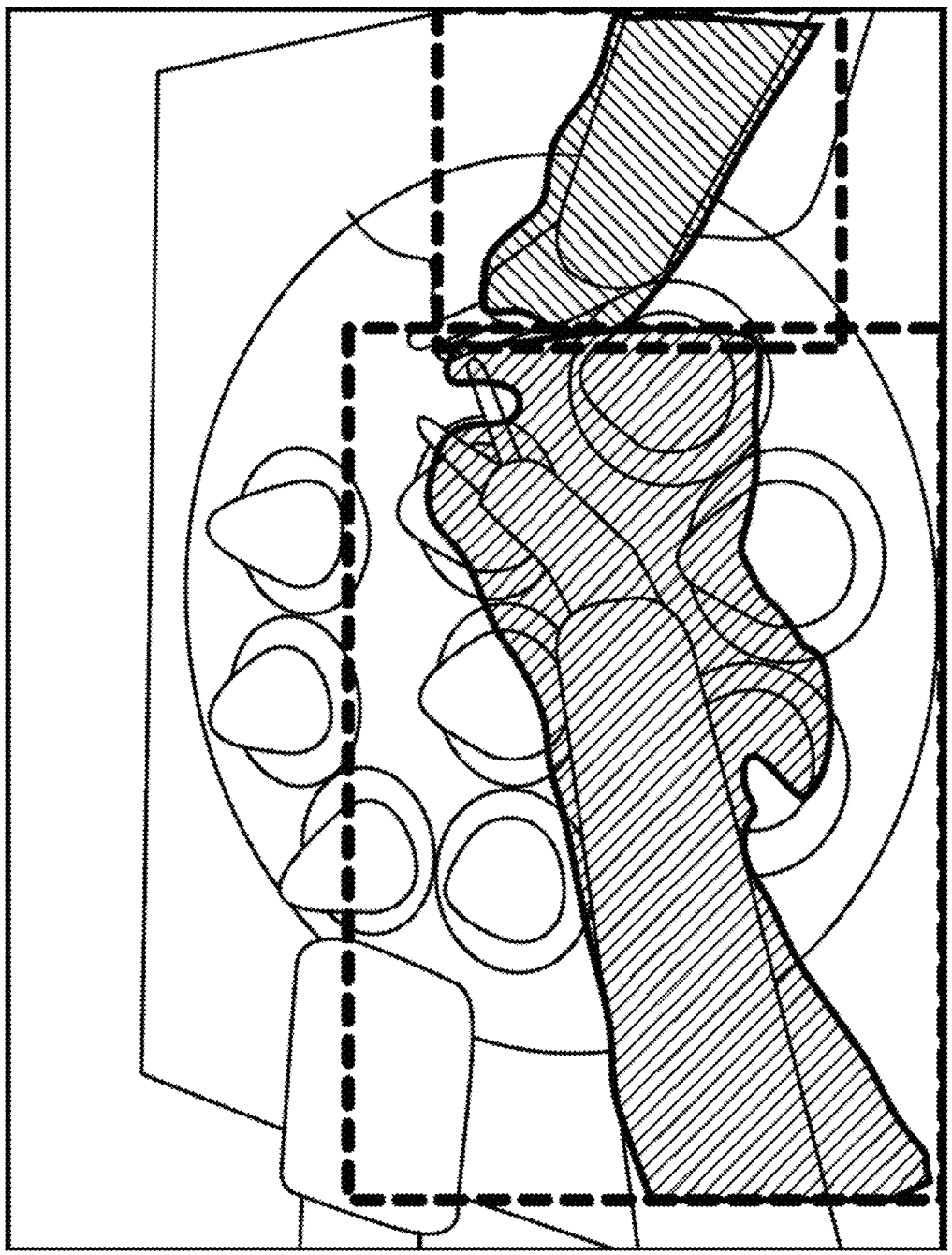
FIG. 11-BF

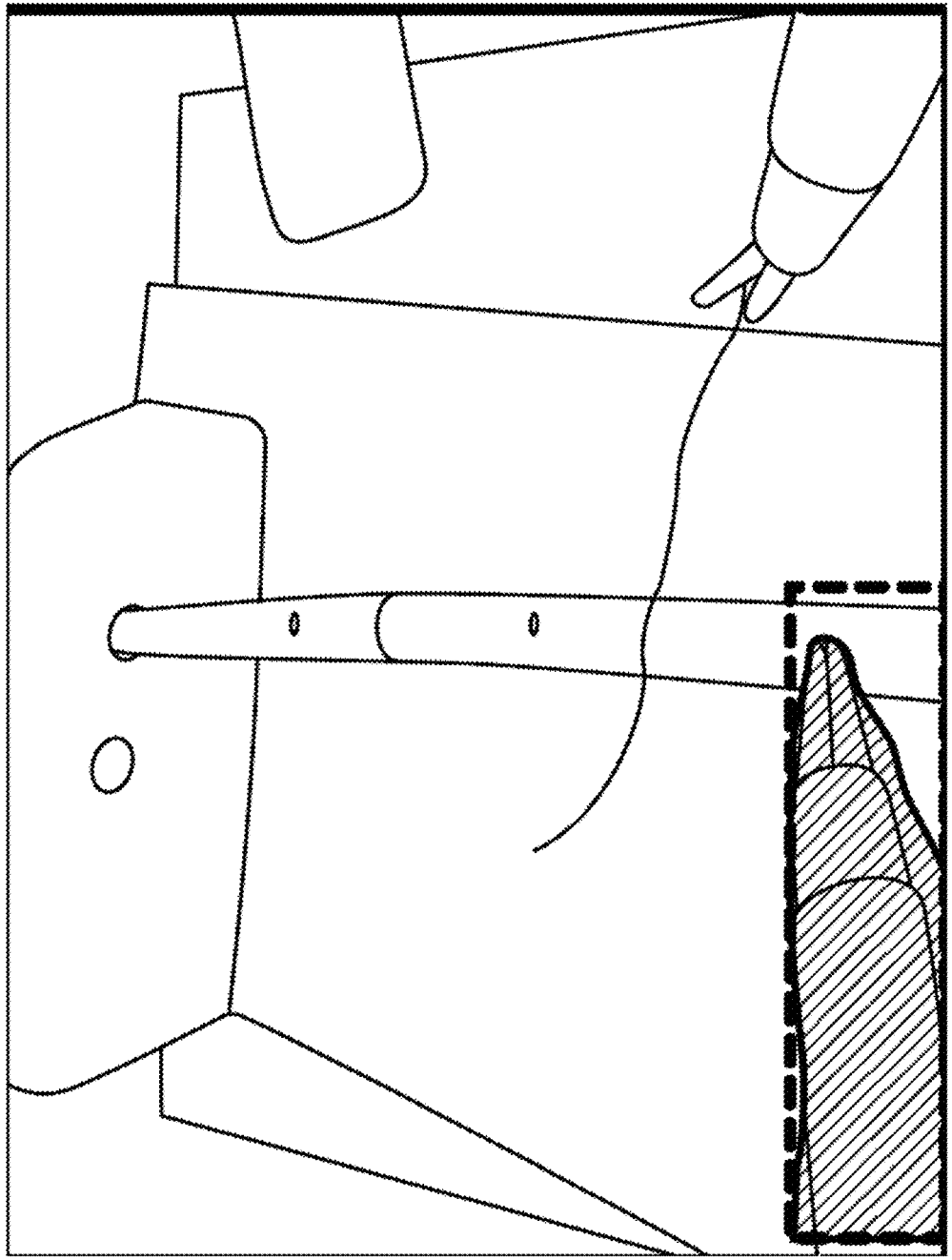
FIG. 11-BG

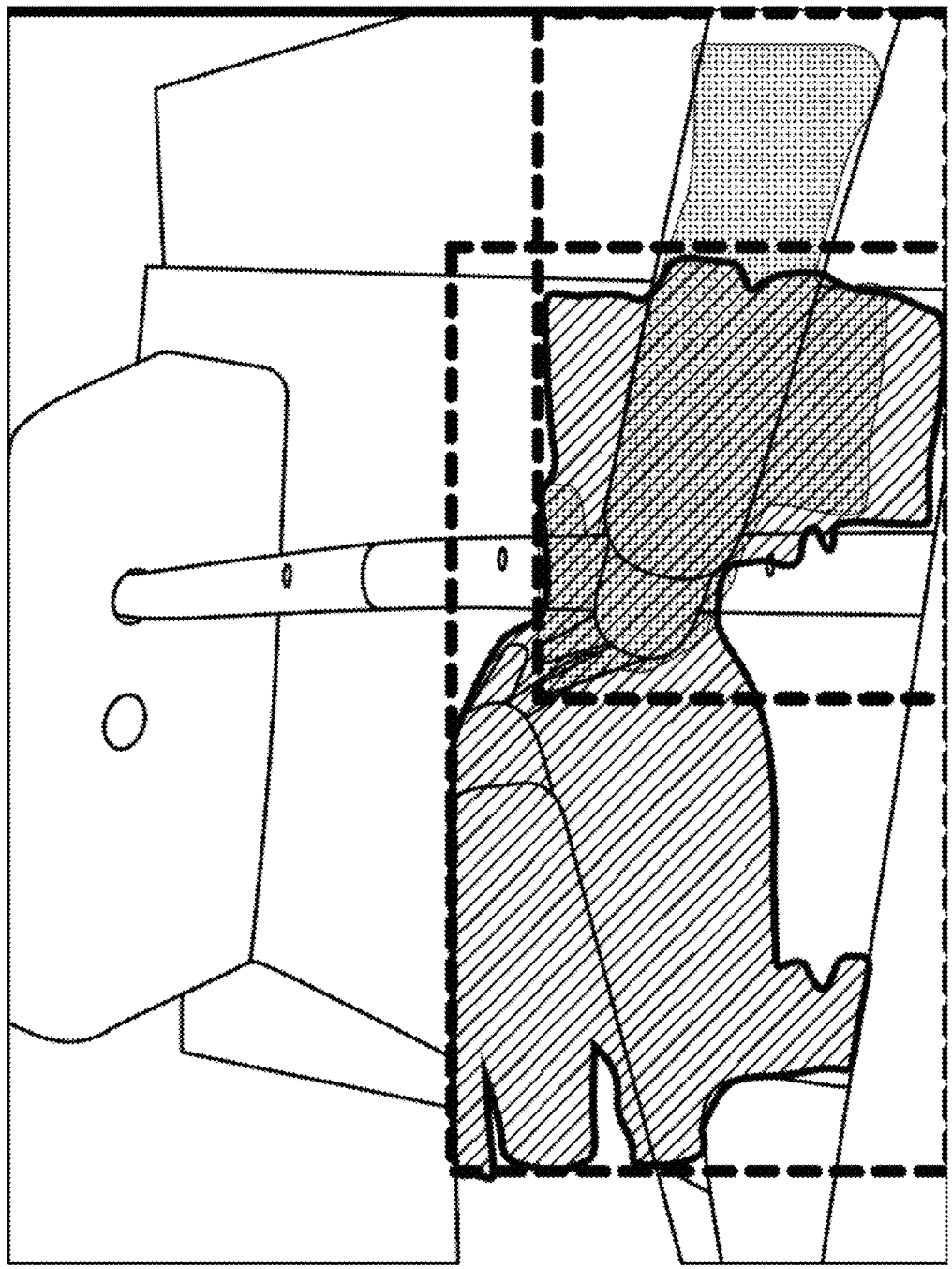
FIG. 11-BH

# SYSTEM AND METHOD FOR SURGICAL PERFORMANCE TRACKING AND MEASUREMENT

CROSS-REFERENCE

This application is a non-provisional of, and claims all benefit, including priority of U.S. Provisional Application No. 62/852,054 filed May 23, 2019, entitled "SYSTEM AND METHOD FOR SURGICAL PERFORMANCE TRACKING AND MEASUREMENT", incorporated herein by reference.

FIELD

The present disclosure generally relates to machine learning architectures for performance measurement of surgical procedure video data set, and in particular to machine learning architectures for reducing surgical procedure video data set for processing with sequential relation architectures operating on commercially available computing resources.

INTRODUCTION

Embodiments described herein relate to the field of medical devices, systems and methods and, more particularly, to medical or surgical devices, systems, methods and computer readable medium to assess surgical procedure performance based on surgical procedure video data set.

SUMMARY

In accordance with an aspect, there is provided a system and method for assessing surgical procedures based on processing surgical procedure video data set with a machine learning architecture. In a first aspect, the machine learning architecture includes a dimensionality reduction architecture to discover and extract, from the video data, features which are indicative of surgical instruments, and a sequential relation architecture, to assess a sequence of features which are indicative of surgical instruments and link said features to surgical performance and surgical skill. The machine learning architecture may process the video data with commercially available computing resources, allowing for review of a greater amount of the large number of surgical procedures performed daily, which are infeasible to review; therefore, reducing the loss of invaluable performance data that would otherwise be useful for improving surgical safety.

In accordance with another aspect, there is provided a second system and method for assessing surgical procedures based on processing surgical procedure video data set with a machine learning architecture which includes, a surgical instrument instance segmentation architecture, a decomposition model, and a sequential relation architecture. The surgical instrument instance segmentation architecture is used to discover and extract, from the video data, features which are indicative of surgical instruments and create a mask of the instrument based on said features. The decomposition model extracts critical information (i.e., key point characteristics) from the mask (e.g., a length, orientation, and centroid of the instrument), passing key point characteristics which are capable of being processed by the sequential relation architecture with commercially available computing resources. The sequential relation architecture assesses key point characteristics to determine surgical performance and surgical skill. The machine learning architecture may process the video data with commercially available computing resources, allowing for review of a greater amount of the large number of surgical procedures performed daily, which are infeasible to review; therefore, reducing the loss of invaluable performance data that would otherwise be useful for improving surgical safety.

The machine learning architecture described herein, in example embodiments, is capable of accurately assessing surgical performance based on video data by dimensionally reducing frames of the video data from 224×224 (pixels)×3 (with 3 colour channels) dimensions (e.g., 150,528 data points per frame, or 3,612,672 data points per second based on 24 fps, or 216,760,320 data points per minute based on 24 fps) to fewer than 10,000 data points per frame, 240,000 data points per second based on 24 fps, or 14,400,000 data points per minute based on 24 fps), decreasing the amount of data processed by the sequential relation architecture in excess of ten fold, allowing for rapid processing of and increased utilization of surgical procedure video data set. In some example embodiments, the difficulty of processing surgical procedure video data set sampled at ~30 frames/sec, with each frame including approximately 1 MB of data, without prohibitively expensive commercially available means is overcome with the disclosed machine learning architecture by effectively capturing only the most important characteristics of each frame.

As a result of the more rapid processing of the surgical procedure video data set, in example embodiments, the machine learning architecture disclosed herein may be able to generate real-time alerts to surgeons based on the surgical procedure video data set, potentially increasing patient outcomes and reducing loss resulting from surgeon fatigue.

A technical challenge associated with the practical implementation of the machine learning architectures includes extracting features from the limited amount of labelled data available in a timely, cost effective manner while maintaining accuracy in assessing surgical performance.

One aspect of the technical challenge can include extracting, from the surgical procedure video data set, an amount of information sufficient to enable the machine learning architecture to provide real time results without overloading available computer resources of the system. For example, in some approaches, frames from the video data are extracted and linearized, reducing the dimensionality of videos. Selecting the correct combination of linearization tools and types and combinations of dimensionality reduction techniques which are capable of being performed without prohibitively costly computing resources is a technical challenge. As surgeries occur in a variety of locations, and providing a robust solution capable of reducing the dimensionality of videos with widely available computing resources, and without the need for a large investment in computing resources is a technical challenge.

Similarly, the extracting, from the surgical procedure video data set, of an amount of information sufficient to enable the machine learning architecture to provide real time results while maintaining accurate representations of surgical performance is a technical challenge. Computer resources need to be efficiently allocated while maintaining accuracy so as to not compromise patient outcomes. Determining the correct means of extracting correct information which allows accurate predictions with limited computing resources is a technical challenge.

Another aspect of the technical challenge includes being able to provide physicians or surgeons or decision makers with explainable or understandable results. While some deep learning techniques associated with machine learning architectures are, with unlimited resources, capable of accurate assessments of certain phenomena, the techniques ability to provide insights into assessments (e.g., the "why") is lacking. Techniques which produce assessments that can be interpreted by physicians or surgeons or decision makers to better understand the assessments and possibly improve (e.g., using the machine learning architecture as a learning tool) is challenging. Simply advising a surgeon of poor performance is not as challenging as advising a surgeon as to why the performance is poor (e.g., too much rapid movement). Configuring an interpretable machine learning architecture which is explainable is a technical challenge.

A technical challenge includes configuring a machine learning architecture which satisfies a required blend of accuracy, speed and explainability simultaneously. The technical challenge can, for example, include determining a means of extracting surgical instrument characteristics from surgical procedure video data set and assessing surgical performance in a computationally limited setting such as a hospital or based on a lower computational resource availability, correctly and in a repeatable and consistent manner.

Such a machine learning architecture may, if run on commercial hardware, process frames at a much higher speeds than humans, run overnight, is not conditional on the availability of experienced physicians for review, and may operate independent of fatigue. Such a machine learning architecture may take advantage of the large amount of surgical procedure video data set available. Similarly, such architectures may be free from cognitive biases, and bias as a result of variations across surgeons, hospitals, countries, etc.

Another technical challenge is to discover and extract the necessary information from the video data which allows the machine learning architecture to link surgical performance and surgical skill. This is challenging for machines, as there are complex interrelationships between surgical performance and surgical skill. A machine learning architecture which can, for example, estimate skill levels of surgeons performing in surgical procedure video data set is desirable because it is otherwise very costly to assess skill levels (e.g., impractical for human reviewer to review all videos and all elements of videos), and it can be used for various downstream applications, such as identifying and promoting process improvements for patient safety, or insurance tracking applications (e.g., reducing malpractice insurance for particularly skilled practitioners). As the system is a machine learning system, the model architecture can be widely applicable across different instruments and procedure type, depending on the availability of training data.

Other approaches have variously focused on using kinematic data in addition to surgical procedure video data set to determine surgical performance and characteristics, or extracting spectra from surgical procedure video data set with computer vision. However, these approaches do not adequately provide a means of extracting information from surgical procedure video data set which can be processed with the machine learning architecture to provide timely and accurate results of the surgical video, both in terms of detecting a type of surgical action being performed and in terms of a skill level of the surgical performance.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

This application is directed to approaches for assessing surgical performance by configuring a machine learning architecture to extract surgical instrument characteristics from a surgical procedure video data set and assessing surgical performance based on the extracted surgical instrument characteristics. Variants can be implemented in the form of computer systems, methods, and computer program products (e.g., non-transitory computer readable media storing machine-readable instructions).

A system having the machine learning architecture receives as inputs video data of surgical procedures, and processes them either in real-time or near-real time or at some time after the surgical procedure, according to different embodiments. The system can be implemented in the form of a physical computer server that is adapted for processing the videos to generate data outputs, such as data structures storing data values or features representative of inferred temporal patterns from surgical instrument motions that are related to surgical gestures, actions, and performance related cues, which can be used for generating machine-estimate outputs relating to assessments of surgical skill (without the need for a human reviewer).

In a first approach, the machine learning architecture is defined at least in part by a plurality of parameters representative of a dimensionality reduction architecture (e.g., an autoencoder) and a sequential relation architecture (e.g., GRU, self-attention network, etc.).

The first approach includes self-supervised training of the dimensionality reduction architecture to compress and decompress frames from the surgical procedure video data set to extract surgical instrument characteristics in the respective frame of the surgical procedure video data set while reducing dimensionality. The dimensionality reduction architecture includes, an encoder portion (i.e., the first portion), which compresses the frames, and a decoder portion (i.e., the second portion), which reconstructs frames from the compressed frames generated by the encoder portion. The dimensionality reduction architecture is self-supervised by updating its plurality of weights based on a reconstruction loss, which is a loss determined by comparing the reconstructed frame with the input frame (i.e., the frame prior to processing by the dimensionality reduction architecture). In this way, the dimensionality reduction architecture learns to preserve the most important features of the frame when compressing the frame.

In the first approach, the dimensionality reduction architecture is trained based on surgical performance video data. In this manner, the dimensionality reduction architecture learns to preserve surgical instrument characteristics, tissue characteristics, and other characteristics important to surgical performance assessment during the compression process.

Once the dimensionality reduction architecture is trained in an unsupervised manner on a training data set (e.g., the first data set), the trained encoder portion of the dimensionality reduction architecture is used to processes frames of subsequent surgical procedure video data set which have at least one surgical instrument. The encoder portion of the dimensionality reduction architecture reduces the dimensionality of the frames of surgical procedure video data set to a size that is capable of being processed by the sequential relation architecture while retaining necessary information to allow for training the sequential relation architecture to produce accurate assessments of surgical performance. For example, an encoder may be configured to, in response to receiving an image having 512×512 pixels, decrease the dimensionality of the image to 100 pixels, downsampling the input image.

The subsequent surgical performance video data may be the same surgical performance video data used to train the dimensionality reduction architecture. According to some scenarios, the subsequent surgical performance video data are videos of different procedures not seen during training.

The encoder portion of the dimensionality reduction architecture may include a series of convolutional layers (e.g., 2D convolutional layers) which have related activation layers (e.g., ReLu activation layers), which extract various features from a frame, and a pooling layer which processes the extracted features into a representation of the input frame (i.e., an embedding of the frame or a compressed frame). In example embodiments, the encoder includes two sets of convolutional layers and related activation layers which are connected to a pooling layer to provide the embedding.

Similarly, the decoder portion of the dimensionality reduction architecture may include a series of convolutional layers (e.g., 2D convolutional layers) which have related activation layers (e.g., ReLu and Tan h activation layers), which extract various features from a frame. In example embodiments, the decoder includes three sets of convolutional layers and related activation layers are used to reconstruct the input frame. In regards to the example of an image having 512×512 pixels, the decoder may increase the dimensionality of the downsampled 100 frames, and upsample the reduced dimensional image back to the original 512×512 pixels. This upsampled image can be a most effective representation (i.e., the 100 most important/meaningful pixels in the original image) where the encoder and decoder are trained to process the original image (i.e., frame) to determine the most meaningful 100 pixels. The dimensionality reduction architecture can be trained to find the most effective representation based on a processing speed threshold, or an expected computing resource availability, or an accuracy threshold, or some combination of the three.

Some embeddings (i.e., compressed frames) yielded representations of better quality but were too large to be able to train the machine learning architecture on commercially available hardware. The technical solution of determining a smallest representation which gives flexibility while training and retains accuracy is challenging to achieve.

The trained encoder portion passes the respective frame embeddings (i.e., compressed frames) to the sequential relation architecture which contain the extracted surgical instrument characteristics for each frame. The sequential relation architecture processes the extracted surgical instrument characteristics over the plurality of frames within the surgical performance video data object, and generates, for each frame, a value indicative of the surgical instrument motion of the surgical instrument. The sequential relation architecture may be a bi-directional or self-attention sequential relation architecture for incorporating past and future values of the extracted surgical instrument characteristics to determine the value indicative of the surgical instrument motion.

The value indicative of surgical instrument motion is compared to a label of the surgical procedure video data set, and the comparison is used to update the plurality of parameters. In some scenarios, the label is a label indicative of surgical skill shown in the video and the machine learning architecture learns to better predict surgical skill in surgical procedure video data set. In some scenarios, the label is a label indicative of a type of surgical procedure being performed in the video (e.g., a laparoscopy) and the machine learning architecture learns to better predict type of surgical procedures shown in surgical procedure video data set. In some embodiments, the label is a Global Rating Score (GRS), or a category defined by the Objective Structured Assessment of Technical Skills (OSATS), and so forth. The label may be any ratings score for surgical skill which is compared to a predicted rating score for surgical skill represented by the value indicative of surgical instrument motion.

In example embodiments, the sequential relation architecture is a bi-directional sequential relation architecture, and the dimensionality reduction architecture includes a first convolutional layer connected to a first activation layer for successively compressing a part of each frame in the respective plurality of frames in the respective surgical procedure video data set into a partially compressed frame kernel; a second convolutional layer receiving the partially compressed frame kernel and connected to a second activation layer for processing each the partially compressed frame kernel in the respective frame into a further partially compressed frame kernel; a pooling layer for extracting a respective partial feature from each further partially compressed frame kernel; wherein the respective partial feature of the respective frame is processed into the compressed frame; a third convolutional layer connected to a third activation layer for successively decompressing a part of each compressed frame into a partially decompressed frame kernel; a fourth convolutional layer connected to a fourth activation layer for successively decompressing the partially decompressed frame kernel of each compressed frame into a further partially decompressed frame kernel; a fifth convolutional layer connected to a fifth activation layer for successively decompressing the further partially decompressed frame; wherein the respective further partially decompressed frame of the respective frame is processed into a reconstructed representation of the respective frame; and wherein the reconstruction loss is based on a comparison of the respective frame and the reconstructed representation of the respective frame. This specific configuration of the dimensionality reduction architecture and sequential relation architecture may yield state-of-the-art results on the JIG-SAWS dataset.

The plurality of parameters which define the machine learning architecture constituent elements, such as the sequential relation architecture and the dimensionality reduction architecture, may be updated according to a dynamic gradient, such as an Adam optimizer, to learn relevant surgical instrument characteristics faster.

In a second approach, the machine learning architecture is defined at least in part by a plurality of parameters representative of a surgical instrument instance segmentation architecture, a decomposition model, and a sequential relation architecture.

The surgical instrument instance segmentation architecture generates a mask representative of a surgical instrument in each frame of the surgical procedure video data set. The surgical instrument instance segmentation architecture may include a Mask-RNN, configured to generate masks based on a pixel level likelihood of each pixel within a frame belonging to a surgical instrument. For example, the surgical instrument instance segmentation architecture may be a Mask-RNN pre-trained on the COCO dataset, and subsequently further trained with a data set which includes surgical instruments. Each mask may be represented by a series of binary vectors, where the non-zero coordinates indicate the presence of an identified mask.

According to some scenarios, further training a pre-trained Mask-RNN machine learning architecture (alternatively referred to as a mask generator) includes freezing a fixed number of layers (represented by a plurality of interconnected parameters) of the mask generator to focus the mask on a reduced number of mask types. For example, a pre-trained mask generator machine learning architecture, which can identify the difference between a horse and a house, may have layers fixed to simplify learning to layers that distinguish between objects, or high level features such as edges, relevant to surgical instrument identification.

In example embodiments, to prevent overloading available computing resources, the pre-trained mask generator machine learning architecture of the surgical instrument instance segmentation architecture may have every layer therein frozen, and a final layer modified to have only outputs indicative of surgical instrument characteristics. Subsequent training of the surgical instrument instance segmentation architecture based on input surgical performance video data may teach the pre-trained mask generator machine learning architecture to more accurately identify surgical instruments.

In some embodiments, for example, the mask generator machine learning architecture may be fine tuned to identify surgical instruments by only having output layers which are representative of surgical instrument characteristics.

In the second aspect, for each frame, and for each mask generated by the surgical instrument instance segmentation architecture in each frame, the respective mask is decomposed into key point mask characteristics to extract surgical instrument characteristics.

In some scenarios, the key point mask characteristics include a centroid, length, and orientation of the respective masks. For example, a centroid of the key point mask characteristics can be determined based on (1) determining a covariance matrix for each mask, (2) performing an eigenvector decomposition for the covariance matrix to determine a first eigenvector for each mask in corresponding to the direction of a largest variance within the mask, and a second eigenvector for each mask corresponding to the direction of a second largest variance within the mask; and (3) determining a centroid mask characteristic based on the first eigenvector and the second eigenvector for each mask. In this way, the determined centroid can be used to capture aspects indicative of surgical instrument motion.

Similarly, the length and orientation of the respective masks can be determined based on, respectively, the orientation of the first eigenvector and a function based on the centroid of the mask and the orientation and can be used to capture aspects indicative of surgical instrument motion.

These extracted surgical instrument characteristics are processed over the plurality of frames by the sequential relation architecture, which generates, for each frame, a value indicative of the surgical instrument motion of surgical instruments over the plurality of frames. The sequential relation architecture may be a bi-directional or self-attention sequential relation architecture for incorporating past and future values of the extracted surgical instrument characteristics to determine the value indicative of the surgical instrument motion.

The value indicative of surgical instrument motion is compared to a label of the surgical procedure video data set, and the comparison is used to update the plurality of parameters. In some scenarios, the label is a label indicative of surgical skill shown in the video and the machine learning architecture learns to better predict surgical skill in surgical procedure video data set. In some scenarios, the label is a label indicative of a type of surgical procedure being performed in the video (e.g., a laparoscopy) and the machine learning architecture learns to better predict type of surgical procedures shown in surgical procedure video data set. In some embodiments, the label is a score tied to a rating, such as a Global Rating Score (GRS), or a category defined by the Objective Structured Assessment of Technical Skills (OSATS), and so forth.

In this way, it may be possible to capture sufficient characteristics of the surgical instruments with fewer data points, extracted from the surgical procedure video data set, allowing for faster evaluation of the surgical procedure video data set. For example, key point mask characteristics may allow the machine architecture to determine a surgical skill shown in surgical procedure video data set representing a real time surgery.

Approaches as set out herein may improve inter-rater reliability across surgeons/hospitals/countries, as the approaches may remove surgeon specific, region specific, or other biases.

Many further features and combinations thereof concerning embodiments described herein will appear to those skilled in the art following a reading of the instant disclosure.

DESCRIPTION OF THE FIGURES

Embodiments will be described, by way of example only, with reference to the attached figures, wherein in the figures:

FIGS. 11AA-11AH illustrate an example set of a predicted segmentation masks overlaid on original image, in accordance with some embodiments;

FIGS. 11BA-11BH illustrates another set of example predicted segmentation masks overlaid on original image, in accordance with some embodiments;

It is understood that throughout the description and figures, like features are identified by like reference numerals.

DETAILED DESCRIPTION

Figure 1:
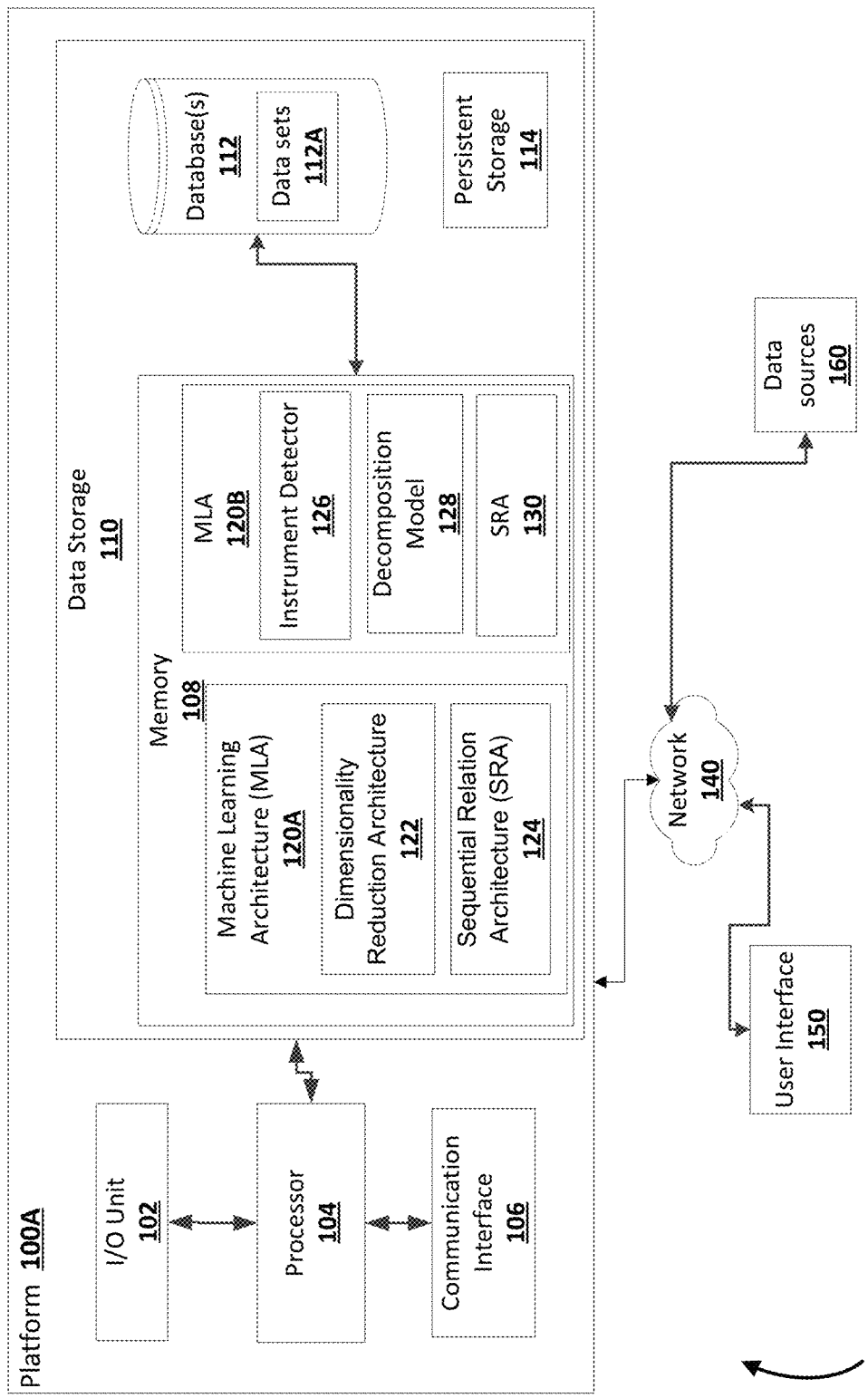
FIG. 1 illustrates, in a component diagram, an example of a system for surgical performance tracking and measurement, in accordance with some embodiments.

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing implementation of the various example embodiments described herein.

In accordance with an aspect, there is provided a system and method for assessing surgical procedures based on processing surgical procedure video data set with a machine learning architecture.

A technical challenge associated with the practical implementation of the machine learning architectures includes extracting features from the limited amount of labelled data available in a timely, cost effective manner while maintaining accuracy in assessing surgical performance. One aspect of the technical challenge can include extracting, from the surgical procedure video data set, an amount of information sufficient to enable the machine learning architecture to provide real time results without overloading available computer resources of the system. Similarly, the extracting, from the surgical procedure video data set, of an amount of information sufficient to enable the machine learning architecture to provide real time results while maintaining accurate representations of surgical performance is a technical challenge.

For example, in some approaches, frames from the video data are to assess surgical performance. Implementing the correct combination of linearization tools and types and combinations of dimensionality reduction techniques which are capable of being performed without prohibitively costly computing resources is a technical challenge. As surgeries occur in a variety of locations, and providing a robust solution capable of reducing the dimensionality of videos with widely available computing resources, and without the need for a large investment in computing resources is a technical challenge.

As the technology which is used to capture surgical videos has greatly increased the granularity of data captured by a surgical video data set, a proposed solution needs to address the fact that commercially available computing resources are unable to process the full richness of the captured data in a surgical video data set. For example, a 1080p video frame has 1,920 pixels, and with equipment which can capture 60 frames per second, a single second of a surgical video data set can include 115,200 data points. With this standard, it is not uncommon for a single minute of video to require 130 MB of space.

A machine learning architecture which can process that amount of information, in a timely manner, and sorting through data which is not relevant, needs to solve the technical problems of determining which data to capture from the available data, and how to process that data without overloading the available computing resources while maintaining accuracy. The technical challenge includes configuring the machine learning architecture which satisfies a required blend of accuracy, speed and explainability simultaneously. The technical challenge can, for example, include determining a means of extracting surgical instrument characteristics from surgical procedure video data set and assessing surgical performance in a computationally limited setting such as a hospital or based on a lower computational resource availability, correctly and in a repeatable and consistent manner.

Such a machine learning architecture may, if run on commercial hardware, process frames at a much higher speeds than humans, run overnight, is not conditional on the availability of experienced physicians for review, and may operate independent of fatigue. Such a machine learning architecture may take advantage of the large amount of surgical procedure video data set available. Similarly, such architectures may be free from cognitive biases, and bias as a result of variations across surgeons, hospitals, countries, etc.

Other approaches have variously focused on using kinematic data in addition to surgical procedure video data set to determine surgical performance and characteristics, or extracting spectra from surgical procedure video data set with computer vision. However, these approaches do not adequately provide a means of extracting information from surgical procedure video data set which can be processed with the machine learning architecture to provide timely and accurate results of the surgical video, both in terms of detecting a type of surgical action being performed and in terms of a skill level of the surgical performance.

In a first aspect, the proposed machine learning architecture includes a dimensionality reduction architecture to discover and extract, from the video data, features which are indicative of surgical instruments, and a sequential relation architecture, to assess a sequence of features which are indicative of surgical instruments and link said features to surgical performance and surgical skill. The machine learning architecture may process the video data with commercially available computing resources, allowing for review of a greater amount of the large number of surgical procedures performed daily, which are infeasible to review; therefore, reducing the loss of invaluable performance data that would otherwise be useful for improving surgical safety.

In accordance with another aspect, there is provided a proposed second system and method for assessing surgical procedures based on processing surgical procedure video data set with a machine learning architecture which includes, a surgical instrument instance segmentation architecture, a decomposition model, and a sequential relation architecture. The surgical instrument instance segmentation architecture is used to discover and extract, from the video data, features which are indicative of surgical instruments and create a mask of the instrument based on said features. The decomposition model extracts critical information (i.e., key point characteristics) from the mask (e.g., a length, orientation, and centroid of the instrument), passing key point characteristics which are capable of being processed by the sequential relation architecture with commercially available computing resources. The sequential relation architecture assesses key point characteristics to determine surgical performance and surgical skill. The machine learning architecture may process the video data with commercially available computing resources, allowing for review of a greater amount of the large number of surgical procedures performed daily, which are infeasible to review; therefore, reducing the loss of invaluable performance data that would otherwise be useful for improving surgical safety.

The machine learning architecture described herein, in example embodiments, is capable of accurately assessing surgical performance based on video data by dimensionally reducing frames of the video data from 224×224 (pixels)×3 (with 3 colour channels) dimensions (e.g., 150,528 data points per frame, or 3,612,672 data points per second based on 24 fps, or 216,760,320 data points per minute based on 24 fps) to fewer than 10,000 data points per frame, 240,000 data points per second based on 24 fps, or 14,400,000 data points per minute based on 24 fps), decreasing the amount of data processed by the sequential relation architecture in excess of ten fold, allowing for rapid processing of and increased utilization of surgical procedure video data set. In some example embodiments, the difficulty of processing surgical procedure video data set sampled at ~30 frames/sec, with each frame including approximately 1 MB of data, without prohibitively expensive commercially available means is overcome with the disclosed machine learning architecture by effectively capturing only the most important characteristics of each frame.

As a result of the more rapid processing of the surgical procedure video data set, in example embodiments, the machine learning architecture disclosed herein may be able to generate real-time alerts to surgeons based on the surgical procedure video data set, potentially increasing patient outcomes and reducing loss resulting from surgeon fatigue.

Embodiments of methods, systems, and apparatus are described through reference to the drawings.

Embodiments may provide a system, method, platform, device, and/or a non-transitory computer readable medium for tracking, monitoring and measuring performance in a surgical operating room (OR), intensive care unit, trauma room, emergency department, interventional suite, endoscopy suite, obstetrical suite, and/or medical or surgical ward, outpatient medical facility, clinical site, or healthcare training facility (simulation centres). These different example environments or settings may be referred to as an operating or clinical site.

Embodiments described herein may provide devices, systems, methods, and/or computer readable medium for performance tracking and measurement in surgical videos.

Performance evaluation of surgical operators is currently done by experienced doctors who rely on either real-time live observations, or the review of surgical videos to assess the ability of surgeons. This evaluation is based on sets criterion that are dependent on local, provincial, federal or other governmental policies. This task is tire-some, prone to subjectivity and inconsistency due to the variability between evaluators and evaluation criteria, prone to human loss, requires extensive training/education of evaluators, and is time consuming such that it is impossible to exhaustively review all surgical procedures. Due to the large number of surgical procedures performed daily, it is infeasible to have doctors review every procedure. There is thus a loss of invaluable performance data that would be invaluable to surgeons as they hone their craft to become more effective at their jobs.

As such, the ability to perform objective performance assessments is significantly limited in both the quantity of surgical procedures that can be assessed, as well as the quality of the surgical procedures that do get assessed.

Surgeons can benefit from tools that can provide them with feedback regarding their performance so that they can work on their skills and become better surgeons. In some embodiments, computer vision and deep learning techniques are leveraged to create models and algorithms that can provide a quantitative analysis of surgical performance. In some embodiments, deep learning software and computer vision technology are implemented on the internal views of surgeries (i.e., from surgical recordings) to classify the performance of surgical teams into categories defined by the Objective Structured Assessment of Technical Skills (OSATS).

In some embodiments, computer vision and deep learning techniques may be leveraged to create end-to-end models that can provide a quantitative analysis of surgical performance. The ability to classify or grade surgical performance has the added benefit to potentially improving surgical outcomes as studies have shown that there exists a correlation between performance and outcome.

In some embodiments, a series of deep-learning models are incorporated into machine learning architecture to take in a plurality of frames from surgical procedure video data set as input. Each machine learning architecture may be tasked with extracting important features of interest from these frames, and then using the information derived from these features (e.g., the value related to surgical instrument motion) for the purposes of classification. An example of this process would be the identification and location of surgical instruments within the frames. The movement of these surgical instruments between frames can be determined, and such information can be used in a variety of ways in order to assess the ability of the surgical teams. In some embodiments, the completed solution comprises an end-to-end classifier of OSATS scores for surgical videos and will produce results in real-time or near-real-time.

In some embodiments, the present disclosure teaches automated application of OSATS scores for surgical video data. In some embodiments, the present disclosure teaches a novel system architecture consisting of a sequence of classification and feature extraction models. In some embodiments, the present disclosure teaches self-supervised architectures using novel deep-learning architectures for surgical tool detection. In some embodiments, the present disclosure teaches self-supervised models using novel deep-learning architectures for surgical tool tracking. In some embodiments, real-time or near-real-time assignment of scores are provided.

The segmentation of surgical instruments and the automatic classification of video data to produce OSATS scores is an incredibly meticulous task. It encompasses the careful curation of manually labeled data, from self-recorded surgical videos. The proposed machine learning architectures (MLAs) can be trained separately using a variety of labeled data. One aspect includes training the MLAs with training data comprising masks of surgical instruments (e.g., medical tools). Such a dataset did not exist prior to the present disclosure. Months of manual annotation was performed to prepare such a dataset. The OSATS labels were prepared over a period of months by the manual annotation of experienced analysts. In some embodiments, the present disclosure provides a resulting MLAs and the training data used for the training of their constituent elements.

In some embodiments, a system will provide real-time or near-real-time tracking of surgical tools and the assignment of OSATS scores for surgical video data by leveraging novel MLA(s). Existing attempts at doing this do not provide real-time or near-real-time results, and they do not use MLAs for training models to predict the utility of time-sequential tracking data for the designation of OSATS scores. By leveraging this novel technology, it may become possible to objectively assess performance of surgical teams for training purposes, rather than have to sacrifice consistency via the inherent subjectivity and biases of manual human assessment. Further, this technology can be applied to, theoretically, a limitless number of procedures to learn more about the surgical environment than otherwise would be possible from manual assessment by humans.

In some embodiments, the system will consider only the contents of video data and the constituent frames in order to predict OSATS scores. This can be replicated largely by utilizing low-level computer vision tools that simply achieve that task of tool tracking but with low accuracy. The extracted features can then be engineered to create a simple analytical/regression model to predict scores of some kind (not necessarily OSATS).

In some embodiments, the MLA may be refined or augmented to incorporate elements which take into consideration other inputs such as audio data or kinematic data which can ultimately increase the predictive capability of the overall MLA by providing further relevant data.

In some embodiments, in the extreme case that the surgeon is fatigued and is taking much longer to do the surgery than is expected, the OSATS score assigned to the surgeon for the "Flow of Operation" category will be low. This might trigger an alarm which would allow for a response from the hospital to bring in a different surgeon to complete the surgery, thereby lowering the risk of an adverse event during surgery.

In some embodiments, if the surgeon or surgical assistant forgets to remove a clamp during surgery, the real-time or near-real-time detection of tools would help with the identification of a tool that is not supposed to be present during a particular phase of the surgery. Again, this may lead to an alarm allow for corrective action which has the potential to reduce the possibility of an adverse event.

In one embodiment, a first computer vision process extracts hand-crafted features from the segmentation of surgical instruments from the constituent frames of surgical videos. A state-of-the-art semantic segmentation model (Mask RCNN) may be used in order to capture surgical tool information at a frame level. Accurately detecting and tracking surgical tools within each of these videos allows for a fine-grained analysis of the surgeon's instrument handling efficiency, elegance of motion and autonomy over the course of the surgery. Attempting to relate the extracted data to the qualitative attributes mentioned above is a challenging task as it requires the modelling of both spatial and temporal features.

In another embodiment, a second computer vision process explores the latent space of each of the constituent frames of the input laparoscopic videos by building a low dimensional embedding (i.e., compressed frames) of spatial features. In some embodiments, the OSATS category of Instrument Handling may be used.

Extensive research has been done to capture the motion of tools in order to infer the performance or skill level of the controlling surgeon directly from laparoscopic videos. The most recent of which quantified operative skill through the use of deep convolutional networks. A Fast-RCNN architecture may be trained using a subset of frames from the m2cai16-tools dataset in order to detect surgical tools present in each frame. The motion of the detected object is then tracked along a sequence of frames and an attempt was made to correlate this tracked motion to surgical performance. The previous paper used GOALS as a template for surgical performance and thus attempts to extract information about areas of interest such as tool usage patterns, movement range and economy of motion.

In contrast, the present disclosure extracts more insights directly from the frames and provides an end-to-end solution which not only extracts a combination of high-level and low-level features directly from the input video frames but runs the resulting features through a sequential relation architecture to infer temporal relations from the data. The present disclosure may generalize to surgical procedures without robotic assistance and can use exclusively visual cues to estimate validated performance scores and GRS scores directly from surgical procedure video data set. The present disclosure provides a framework to automatically evaluate performance during surgical tasks shown in surgical procedure video data set, which has the potential to provide feedback to surgeons, potentially in the context of effective curriculum creation and advanced surgical education.

In some embodiments, not only detection, but also segmentation of the tools visible in each frame of the input video is performed. This allows for extraction of not just the position of the instruments but also its corresponding orientation. In some embodiments, to achieve this, a pre-trained Mask-RCNN model is trained on the COCO dataset and fine-tuned using 4180 annotated frames.

The area of skill assessment through statistical analysis of kinematic data extracted from robot-assisted surgeries has also been widely explored. Recent publications have used kinematic data acquired from a computer that is built into a robotic system and processed using a set of convolutional and recurrent networks in order to classify performance and in the case of the latter, to correlate the results to patient outcomes. Another publication presents a convolution-based architecture as an alternative to Hidden Markov Models based evaluation approaches which depend on unreliable gesture boundaries. Another publication proposes an approach that uses computer vision techniques in conjunction with kinematic data to model performance evaluation as a regression-based task. The aforementioned paper considers the motion of the surgeon's hands during conventional open procedures. In contrast, the present disclosure teaches the tracking of tool motion during laparoscopic procedures.

Another publication also provides a basis for measuring surgical performance by considering symbolic, texture and frequency-based feature types. Also, the training dataset presented by the group contains images of surgeons performing simple surgical actions. Their hand motions are then tracked by extracting the aforementioned features. The results indicate that frequency-based features outperform both symbolic and texture features.

These publications are understandably very subjective in nature and focus mostly on surgeries where kinematic data of robotic surgical instruments is readily available.

In some embodiments, the present disclosure provides an end-to-end pipeline that can be used to predict surgical performance (for example, as defined by the OSATS).

FIG. 1 is a diagram of a system 100 for tracking and measuring performance in surgical procedure video data set. This system 100 implements a machine learning architecture to identify surgical instruments or surgical instrument characteristics in the surgical procedure video data set, and may estimate the performance of the surgical procedure shown in the surgical procedure video data set based on a standardized classification systems.

The system 100 implements a machine learning architecture for assessing surgical performance based on an input surgical procedure video data set. Previous approaches require manual human detection, which would require human labour to review surgical video recordings post-operatively to detect surgical tool and/or technical performance tracking vents and evaluate them. This is labour intensive, cannot be done in real-time, and is prone to the traditional limitations (biases, inconsistencies between reviewers, time limitations, fatigue, etc.) that human-centric endeavours entail.

According to a first aspect, the system 100 implements system for a machine learning architecture for surgical performance tracking and measurement defined by a plurality of parameters representative of a dimensionality reduction architecture and a sequential relation architecture. According to a second aspect, the system 100 implements system for a machine learning architecture for surgical performance tracking and measurement defined by a plurality of parameters representative of a surgical instrument instance segmentation architecture, a decomposition model, and a sequential relation architecture.

The system 100 can incorporate a plurality of parameters representative of pre-trained models into the machine learning architecture and re-train the pre-trained models with surgical performance video data to maximize the accuracy, resource effectiveness, and cost effectiveness of the machine learning architecture determining surgical performance and measurement tasks.

In example embodiments, the system 100 implements a modular machine learning architecture for determining surgical performance tracking and measurement which can include various inputs. For example, various plurality of parameters representative of various convolutional networks may be incorporated into the dimensionality reduction architecture. In a further example, the machine learning architecture can have modules added which consider kinematic data.

The system 100 can use the machine learning architecture to process surgical performance video data in real-time or near real-time in some embodiments. The system 100 can implement the process post-operatively to surgical performance video data in some embodiments.

The system 100 implements machine learning architecture for surgical performance tracking and measurement which, when trained, can be used without the need for human reviewing, in some embodiments.

The system 100, in example embodiments, trains the machine learning architecture to identify, based on surgical instrument characteristics, track and measure surgical performance. The system 100 implements a novel modular architecture with reasoning layers to identify surgical tools, operations and performance. A machine learning architecture trained in this way can be more reliable and explainable which is important in medicine.

The system 100 implements an unbiased, objective process to identify, track and measure surgical performance. The system 100 implements a real-time process to detect surgical tools and operating steps, and generates alert notification when an odd occurrence takes place. The system 100 implements a real-time or near real-time process to measure surgical technical performance.

The system 100 trains and uses a machine learning architecture that involves surgical expertise to process surgical procedure video data set (e.g., video data of laparoscopic surgeries, robotic, open) for generating recommendations for different types of quality improvement. The system 100 can process the surgical procedure video data set with the machine learning architecture to generate an alert or recommendation. The system 100 may identify a specific surgical tool or events and simultaneously estimate a performance for analytical purposes and to gather data that can be used to improve surgery.

The system 100 trains machine learning architecture to process surgical video for surgical performance measurement. This can involve pre-processing the received video data, training neural network models, and comparing the performance of the neural network models. Multiple models are trained to identify the surgical tools and technical steps, and those with the best accuracy-to-speed balance are selected for use by system 100.

The system 100 may significantly reduce the time to review a laparoscopic video to review surgical safety, and perform other analytics of interest, on surgical videos. Even the most experienced analysts are subject to traditional human limitations that will negatively affect the quality of this work, and its potential to accurately draw valuable conclusions to guide future surgical performance. These include fatigue, inconsistencies between individuals, inconsistencies within single individuals, biases, honest loss that go uncorrected, among many others. Further, it is nearly impossible to review millions of surgeries with human forces, and therefore the potential to study and learn of deficiencies in operating rooms, is significantly limited. The system 100 efficiently and automatically perform the desired surgical performance tracking and measurement.

The system 100 can run in real-time, near real-time or post-operatively. For example, the system 100 can run in real-time (as opposed to post-operatively) if desired to track a surgical performance and provide real-time or near real-time feedback. The system 100 can implement aspects of a surgeon evaluation system and patient outcome analysis system.

The system 100 can include a means of creating a feedback mechanism for surgeons, which, based on the assessed performance, would allow surgeons to learn from their experiences and refine their skills.

The system 100 includes a platform 100A which may connect to data sources 170 (including one or more cameras, for example) using network 140 to receive one or more surgical procedure video data sets generated by the data sources 170. Network 140 (or multiple networks) is capable of transmitting data between devices or platforms connected to the network 140 and can involve wired connections, wireless connections, or a combination thereof. Network 140 may involve different network communication technologies, standards and protocols, for example.

User interface 150 application can display an interface of visual elements that can represent surgical performance measurement and alerts, for example. In example embodiments, the user interface 150 is a terminal within a clinical setting.

In example embodiments, the platform 100A retrieves one or more surgical procedure video data sets indirectly, from database(s) 112. For example, the platform 100A may be configured to post-operatively determine surgical performance based on one or more captured and stored surgical procedure video data set.

The platform 100A can include an I/O Unit 102, a processor 104, communication interface 106, and data storage 110.

The processor 104 can execute instructions in memory 108 to implement aspects of processes described herein.

The processor 104 can execute instructions in memory 108 to process one or more surgical performance video data with one or more machine learning architectures (MLA), for example MLAs 120A or 120B, and other functions described herein. The platform 100A may be software (e.g., code segments compiled into machine code), hardware, embedded firmware, or a combination of software and hardware, according to various embodiments.

According to example embodiments, the processor 104 executes instructions in memory 108 to train the MLA 120A, which includes a plurality of parameters representative of an dimensionality reduction architecture 122, and a plurality of parameters representative of a long short term memory (sequential relation architecture) 124.

The dimensionality reduction architecture 122 can be configured to compress data input into the dimensionality reduction architecture 122 (e.g., frames of surgical procedure video data set) and subsequently reconstruct the compressed data into a reconstructed data input. Any type of dimensionality reduction architecture is contemplated. Examples of dimensionality reduction architecture 122 include convolutional auto-encoders.

The dimensionality reduction architecture 122 may be stored as a series values for the plurality of parameters which are non-initiated where the dimensionality reduction architecture 122 is not trained. In some embodiments, the plurality of parameters representative of the dimensionality reduction architecture 122 are stored as non-zero values. For example, after training the MLA 120A, the processor 104 may store the trained plurality of parameters representative of the dimensionality reduction architecture 122 in the memory 108.

The plurality of parameters representative of the sequential relation architecture 124 may include any type of sequential relation architecture or commonly understood variant thereof, including a long short term memory (LSTM), a bi-directional LSTM, a Gated Recurrent Unit (GRU), a transformer, an LSTM classifier, and so forth. The sequential relation architecture 124 may have any number or any combination of an input gate, an output gate and a forget gate used to create a sequential relation architecture.

The plurality of parameters representative of the sequential relation architecture 124 may aid in classifying, processing and assessing surgical performance within the surgical procedure video data set based on surgical instrument characteristics between frames within the surgical procedure video data set. For example, the sequential relation architecture 124 may aid in determining whether the surgical instrument is moving at too great a speed between frames.

According to example embodiments, the processor 104 executes instructions in memory 108 to train the MLA 120B, which includes a plurality of parameters representative of a surgical instrument instance segmentation architecture 126, a decomposition model 128, and a sequential relation architecture 130. The MLA 120B may be trained to analyze aspects of texture in the frame to estimate the location of instruments as well as their trajectories, movement range, and economy of motion.

The plurality of parameters representative of surgical instrument instance segmentation architecture 126 generates a mask for each surgical instrument in each frame of the surgical procedure video data set. According to some embodiments, for example, the surgical instrument instance segmentation architecture 126 generates a mask having binary coordinates, wherein a non-zero coordinate is indicative of a mask.

The plurality of parameters representative of surgical instrument instance segmentation architecture 126 may integrate or include a pre-trained Mask-RNN. For example, the surgical instrument instance segmentation architecture 126 may integrate or include a Mask-RN N pre-trained on the COCO database.

The plurality of parameters representative of the decomposition model 128 may processing each of the masks within the respective frames to generate key point mask characteristics based on extracting surgical instrument characteristics for each mask in the respective frame. Decomposing the mask to key point representations can reduce the amount of computing power required to process the surgical procedure video data set with the MLA 120B. For example, whereas a mask may consist of 50 points, only the length, orientation and endpoints of the mask may be relevant to assessing surgical performance.

Similarly, decomposing the mask to key point representations can increase the explainability of the MLA 120B by forcing the decomposition model 128 to adopt explainable key points. For example, the key point mask characteristics can include a length, orientation and endpoints of the mask.

Sequential relation architecture 130 can be similarly configured to sequential relation architecture 124.

The processor 104 can generate output data, which can for example be provided to user interface 150 or I/O unit 102, indicating the technical performance and/or tool tracking episodes and the corresponding performance measurement. A technical performance and/or tool tracking episode can be represented as a collection of video frames that are annotated as surgical events along with the corresponding performance measurement.

The processor 104 can train one or more MLAs (e.g., MLA 120A or MLA 120B) for surgical performance measurement based on frames within surgical performance video data. The MLAs, as is shown in FIG. 1, can be different types of MLAs having different constituent architectures, for example.

In example embodiments, the processor 104 can select an optimal MLA (of the models 120) for technical performance and/or tool tracking measurement. For example, the processor 104 may select the MLA which has been identified as more accurate or faster in assessing the particular type of surgical performance video data object.

In example embodiments, the processor 104 uses the selected MLA to process the video data of surgical events to generate a pipeline of technical performance and/or tool tracking episodes. The processor 104 can use the selected MLA for performance measurement to evaluate each episode of the pipeline.

In some embodiments, the processor 104 is configured to train one or more MLAs for surgical performance and/or tool detection. In some embodiments, the processor 104 is configured to train one or more MLAs for performance measurement using images and results of surgical and/or tool detection to generate performance measurement and features.

In some embodiments, the processor 104 is configured to update the MLA(s) for technical performance and/or tool tracking or performance measurement using online training.

In some embodiments, the processor 104 is configured to sample a plurality of frames within surgical performance video data in order to generate subsets of the data set which can be stored within the memory 108 (not shown), or stored within the data storage 110 such as within databased 112. For example, the processor 104 may store the multiple subsets of sampled frames of surgical performance video data as data sets 112A, wherein a first data set may be used for training, a second data set used for validation and third data set used for testing. According to some embodiments, the processor 104 stores real-time streamed surgical performance video data as sets of a plurality of frames which are processed consecutively.

In some embodiments, the trained MLA(s) are configured to generate visual elements representing events or alerts based on the processed data sets 112A. The visual elements can be used for user interface 150.

The I/O unit 102 can enable the platform 100A to interconnect with one or more input devices, such as a keyboard, mouse, camera, touch screen and a microphone, and/or with one or more output devices such as a display screen and a speaker.

The processor 104 can be, for example, any type of microprocessor or microcontroller, a digital signal processing (DSP) processor, an integrated circuit, a field programmable gate array (FPGA), a reconfigurable processor, or any combination thereof.

Memory 108 may include a suitable combination of any type of computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Data storage devices 110 can include memory 108, databases 112 (e.g., graph database), and persistent storage 114.

The communication interface 106 can enable the platform 100A to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g., Wi-Fi, WiMAX), SS7 signaling network, fixed line, local area network, wide area network, and others, including any combination of these.

The platform 100A can be operable to register and authenticate users (using a login, unique identifier, and password for example) prior to providing access to applications, a local network, network resources, other networks and network security devices. The platform 100A can connect to different machines or entities 160.

The data storage 110 may be configured to store information associated with or created by the platform 100A. The data storage 110 can store raw video data, data samples, marked surgical tool and/or technical performance tracking frames and performance measurements, and so on. The data storage 110 can implement databases, for example. Storage 110 and/or persistent storage 114 may be provided using various types of storage technologies, such as solid state drives, hard disk drives, flash memory, and may be stored in various formats, such as relational databases, non-relational databases, flat files, spreadsheets, extended markup files, and so on.

Figure 2A:
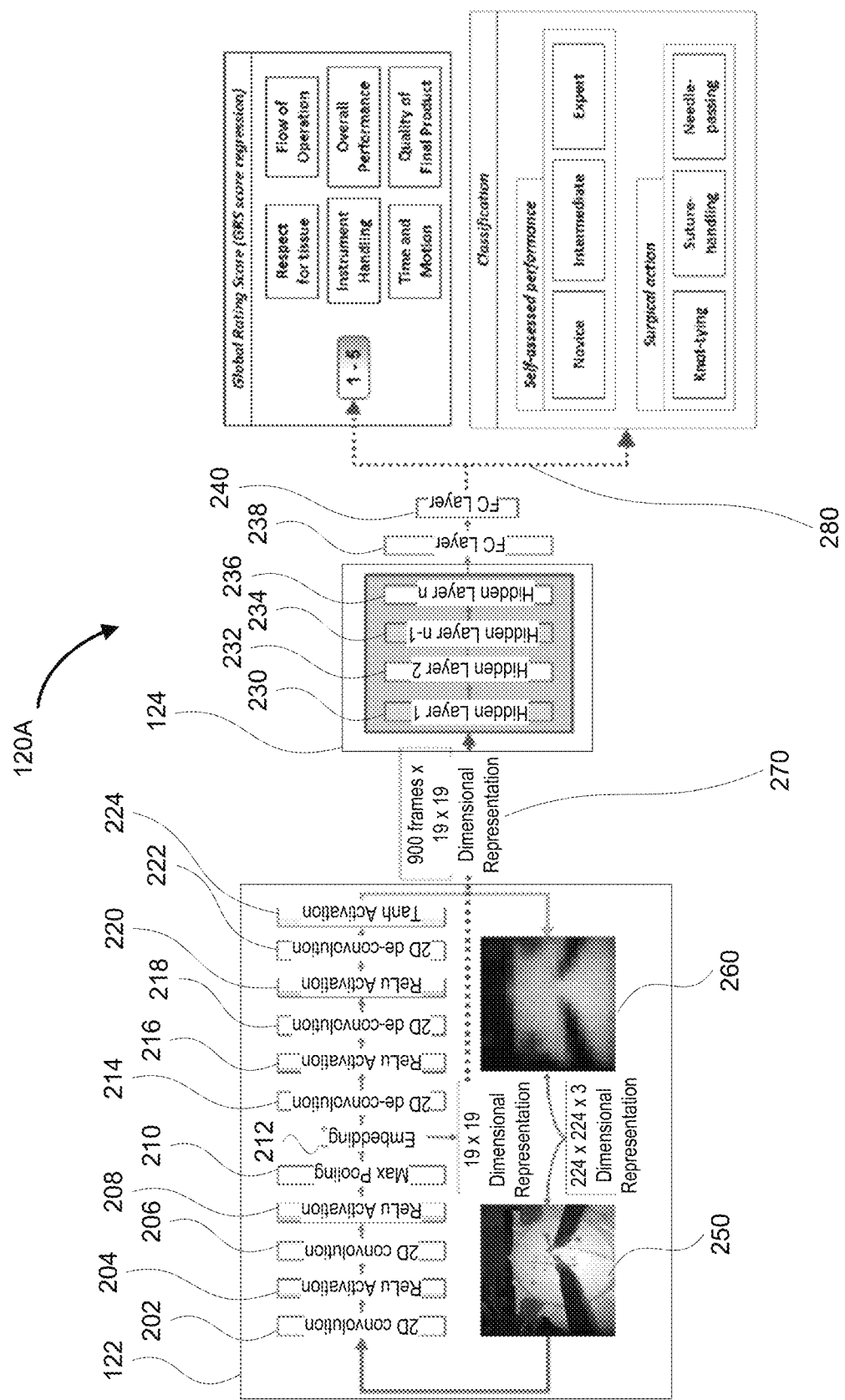
FIG. 2A illustrates an example of a latent representation analysis architecture, in accordance with some embodiments.

Referring now to FIG. 2A, an example MLA 120A for processing latent representations within video data is shown, in accordance with some embodiments. The proposed end-to-end model can be used as a classifier to predict surgical actions and self-reported skill and also as a regression model which predicts scores on the likert-scale for each GRS category.

The MLA 120A shows the dimensionality reduction architecture 122, and the sequential relation architecture 124, including various subcomponents or layers, for example layer 202 of dimensionality reduction architecture 122. Any amount and combination of subcomponents is contemplated.

The dimensionality reduction architecture 122 can be a two-stage neural network that is used for the purpose of dimensionality reduction. The dimensionality reduction architecture 122 is comprised of an encoder and a decoder that can be jointly trained to represent data with a much smaller set of dimensions. The dimensionality reduction architecture's 122 distinguishing characteristic is an hourglass structure as presented in FIGS. 2A and 2B.

Generally, the left portion of the dimensionality reduction architecture 122 is the encoder which applies a series of convolutional, pooling and activation layers to an input (e.g., frame 250) to decrease the dimensionality of the data. The resulting output (e.g., the embedding 212) is effectively a latent representation (i.e. a compressed frame) of the input data, or alternatively referred to as a compact representation of the frame data.

Generally, the right portion of the dimensionality reduction architecture 122 is the decoder which applies a series of up-sampling or 2D transpose convolutions to the data in order to recreate the original image (e.g., a reconstructed image 260) from the low dimensional embedding. The resulting image is then compared to the original image that was used to create the embedding (i.e., the compressed frame) to determine the reconstruction loss.

In the shown embodiments, the dimensionality reduction architecture 122 includes a first convolutional layer 202 connected to a first activation layer 204 for successively compressing a part of each frame 250 (e.g., the input data) in the respective plurality of frames in the respective surgical procedure video data set into a partially compressed frame kernel. In the shown embodiment, the first convolutional layer 202 is a 2D convolutional layer, and the first activation layer 204 is a ReLu activation layer.

In example embodiments, the first convolutional layer 202 can be a convolutional layer for detecting edges in a received frame 250. Any convolution layer is contemplated, for example dilated kernel layer, a combination of 2D and 1D kernel operations, or a 3D kernel layer.

In example embodiments, the first activation layer 204 can be an activation layer configured to pass on data having an edge 250. Any activation layer is contemplated. For example, the activation layer may be a leaky ReLu, an exponential ReLu layer, sigmoid and tanh, and so forth.

The dimensionality reduction architecture 122 further includes a second convolutional layer 206 receiving the partially compressed frame kernel and connected to a second activation layer 208 for processing each of the partially compressed frame kernels in the respective frame 250 into a further partially compressed frame kernel. In the shown embodiment, the second convolutional layer 206 is a 2D convolutional layer, and the second activation layer 208 is a ReLu activation layer.

Similar to the first convolutional layer 202 and the first activation layer 204, the second convolutional layer 206 and the second activation layer 208 may be any convolutional layer and activation layer.

The dimensionality reduction architecture 122 further includes a pooling layer 210 for extracting a respective partial features from each further partially compressed frame kernel. In the embodiment shown, the pooling layer 210 is a max-pooling layer, which extracts respective partial features based on a largest value or outlier within each respective partially compressed frame kernel.

In example embodiments, the pooling layer 210 is an average pooling layer, which extracts respective partial features based on an average of the features within each respective partially compressed frame kernel. Any type of pooling layer is contemplated.

Collectively, the first convolutional layer 202, first activation layer 204, second convolutional layer 206, second activation layer 208, and the pooling layer 210 may hereinafter be referred to as the encoder portion of the dimensionality reduction architecture 122. The encoder portion of the dimensionality reduction architecture 122, as described, reduces the dimensionality of the input frame 250 of surgical performance video data, into a size that is capable of being processed by the sequential relation architecture 124.

The encoder portion of the dimensionality reduction architecture 122 generates the embedding 212 for each frame 250 of the surgical performance video data object, wherein the respective partial feature(s) extracted by the pooling layer 210 of the respective frame 250 is processed into the embedding 212.

The dimensionality reduction architecture 122 further includes a third convolutional layer 214 connected to a third activation layer 216 for successively decompressing a part of each compressed frame into a partially decompressed frame kernel, performing the operations in the opposite direction of the operations carried out by the compressing convolution layers. In the shown embodiment, the third convolutional layer 214 is a 2D de-convolutional layer, and the third activation layer 216 is a ReLu activation layer.

Similar to the first convolutional layer 202 and the first activation layer 204, the third convolutional layer 214 and the third activation layer 216 may be any convolutional layer and activation layer capable of decompressing compressed data.

The dimensionality reduction architecture 122 further includes a fourth convolutional layer 218 connected to a fourth activation layer 220 for successively decompressing the partially decompressed frame kernel of each compressed frame into a further partially decompressed frame kernel. In the shown embodiment, the fourth convolutional layer 218 is a 2D de-convolutional layer, and the fourth activation layer 220 is a ReLu activation layer.

Similar to the first convolutional layer 202 and the first activation layer 204, the fourth convolutional layer 218 and the fourth activation layer 220 may be any convolutional layer and activation layer capable of decompressing compressed data.

The dimensionality reduction architecture 122 further includes a fifth convolutional layer 222 connected to a fifth activation layer 224 for successively decompressing the further partially decompressed frame. In the shown embodiment, the fifth convolutional layer 222 is a 2D de-convolutional layer, and the fifth activation layer 224 is a Tan h activation layer.

Similar to the first convolutional layer 202 and the first activation layer 204, the fifth convolutional layer 222 and the fifth activation layer 224 may be any convolutional layer and activation layer capable of decompressing compressed data.

Collectively, the third convolutional layer 214, third activation layer 216, fourth convolutional layer 218, fourth activation layer 220, fifth convolutional layer 222, and the fifth activation layer 224 may hereinafter be referred to as the decoder portion of the dimensionality reduction architecture 122. The decoder portion of the dimensionality reduction architecture 122, as described, increases the dimensionality of input embeddings of surgical performance video data to generate a reconstructed representation 260 of the respective input frame 250.

The decoder portion of the dimensionality reduction architecture 122 generates the reconstructed representation 260 for each frame 250 of the surgical performance video data object, wherein the further partially decompressed frame of the respective frame 250, generated by the fifth convolutional layer 222 connected to a fifth activation layer 224, is processed into the reconstructed representation 260.

The plurality of parameters which define the dimensionality reduction architecture 122 are updated based on the reconstruction loss, which is a comparison between the input frame 250 and the reconstructed frame 260, training the dimensionality reduction architecture 122 to better compress and reconstruct input frames preserving important information. In the embodiment where the input frame is a frame of the surgical procedure, the dimensionality reduction architecture 122 can learn to preserve surgical instrument characteristics through the compressing enacted by the encoder portion of the dimensionality reduction architecture 122.

The size of the embedding 212 is directly correlated to the quality of the output 250 and depends on the task at hand. The parameters of the encoder and decoder portion of the dimensionality reduction architecture 122 can be set accordingly. It is expected that through training, the dimensionality reduction architecture 122 will learn to retain the most important characteristics of the input data 250 such that it can produce a near-like reconstruction 260 of it from a much smaller embedding size. In an example embodiment, the smallest embedding 212 dimensions that would allow for the construction of a discernible reconstructed frame 260 is chosen.

In example embodiments, the size of the embedding 212 is based on a processing capacity of a processor, used to implement or train the MLA 120A, to process the embedding 212 with the plurality of parameters representative of the sequential relation architecture 124 in an acceptable period of time. For example, the size of the embedding 212 may be configured to allow for processing of videos in real time.

The size of the embedding 212 (i.e., compressed frame) based on a processing capacity of a processor can also include a predicted available computing resource at the location which will implement the MLA 120A. For example, the size of the embedding 212 may be configured to operate on processors connected to limited memories in a surgical operating room.

Mathematically, the operation of the an autoencoder dimensionality reduction architecture 122 can be represented as follows:

$$\text{Encoder: } \mathcal{P} \to \xi \qquad (1)$$

$$\text{Decoder: } \xi \to \mathcal{P}' \qquad (2)$$

$$\mathcal{L}_{oss}(\mathcal{P}, \mathcal{P}') = \|\mathcal{P} - \mathcal{P}'\|^2 \qquad (3)$$

where

𝒫: Original Image
𝒫': Reconstructed. Image
ξ: Embedding

The embedding 212 (e.g., encoded representation) serves the important purpose of allowing for a larger quantity of frames to be fed into the recurrent model (e.g., sequential relation architecture) which can be subsequently trained to learn temporal relations from provided embeddings 212.

In some embodiments, for example, the convolutional and de-convolutional layers (e.g., the second convolutional layer 206, and the fourth convolutional layer 218) both use a kernel dimension of 3 whereas the output channels are 3 and 5 after each layer. The sequential relation architecture 130 consists of two stacked recurrent layers each of which consists of 256 hidden nodes. The output from the last hidden layer is flattened and passed through two fully-connected layers; the first is of dimension 50, and the dimension of the second depends on the predictive task (3 for predicting surgical event and 5 for predicting surgical skill).

In example embodiments, the dimensionality reduction architecture 122 was trained with embeddings 212 of 9,000 frames using the Adam optimizer to update the plurality of parameters representative of the dimensionality reduction architecture 122 with batch sizes ranging from 5 to 10.

Any batch size is completed to allow for varying updating periods of the plurality of parameters. For example, the batch size may be based on the available computing resources (e.g., training on a NVIDIA GeForce GTX1080Ti GPU can only use batch sizes which fill less than ~11 GB of RAM).

In example embodiments, the plurality of parameters representative of the dimensionality reduction architecture 122 are updated based on an Adam optimizer derivative (such as rectified Adam) or adadelta, for example. Any gradient function can be used to update the plurality of parameters representative of the dimensionality reduction architecture 122.

The sequential relation architecture 124 is configured to receive embeddings 212, shown by the path 270, from the dimensionality reduction architecture 122 to generate a value representative of surgical instrument motion 280. In example embodiments, the same surgical procedure video data set used to train the dimensionality reduction architecture 122 are subsequently processed by the dimensionality reduction architecture 122 to generate embeddings 212 sent to the sequential relation architecture 124. According to some embodiments, for example, a surgical procedure video data set separate from the surgical procedure video data set used to train the dimensionality reduction architecture 122 is processed by the dimensionality reduction architecture 122 to generate embeddings 212 which are provided to the sequential relation architecture 124.

The sequential relation architecture 124 of MLA 120A subsequently processes the received embeddings 122. In the example embodiment shown, the sequential relation architecture 124 is configured with a stacked architecture which includes four hidden layers (a first sequential relation architecture layer 230, a second sequential relation architecture layer 232, a third sequential relation architecture layer 234, a fourth sequential relation architecture layer 236). Any number of sequential relation architecture layers are contemplated.

Each intermediate (i.e., not final) layer of sequential relation architecture is configured to provide a sequence of inputs to the subsequent sequential relation architecture layers in the sequential relation architecture 124.

The final sequential relation architecture layer (e.g., the fourth sequential relation architecture layer 236) is configured to generate a single value related to surgical instrument motion 280. The value related to surgical instrument motion 280 will represent the characteristics which the sequential relation architecture 124 is trained to capture during training.

In example embodiments, the value related to surgical instrument motion 280 can include an assessment of the surgical step being performed and the level of the surgeon's competence. For example, the value related to surgical instrument motion 280 can be a representation of a Global Rating Score (GRS), or a category defined by the Objective Structured Assessment of Technical Skills (OSATS), and so forth. These ratings can include novice, intermediate, expert classifications.

In example embodiments, the sequential relation architecture 124 generates the value representative of surgical instrument motion 280 based on surgical instrument motion between frames within in surgical performance video data object.

In example embodiments, the sequential relation architecture 124 provides the value related to surgical instrument motion 280 to the related output layers 238 and 240 (e.g., an LSTM classifier), which interpret or convert the value related to surgical instrument motion 280 generated by the sequential relation architecture 124 into explainable information. In some embodiments, the value related to surgical instrument motion 280 is representative of a classification, such as whether the performance is indicative of a particular surgical procedure (e.g., knot-tying), or a performance assessment (e.g., novice performance).

Any amount and any configuration of output layers is contemplated. More than one output layer may be used to increase the stability of training the MLAs. For example, the output layers may include a single layer having 500-1000 nodes representing possible classifications where value related to surgical instrument motion 280 includes both a class and a label portion, where first layer decreases the 1000 classifications to a manageable ~25 and then finally a layer with ~5. In another non-limiting example, the final layer may have one node for each GRS category.

Figure 2B:
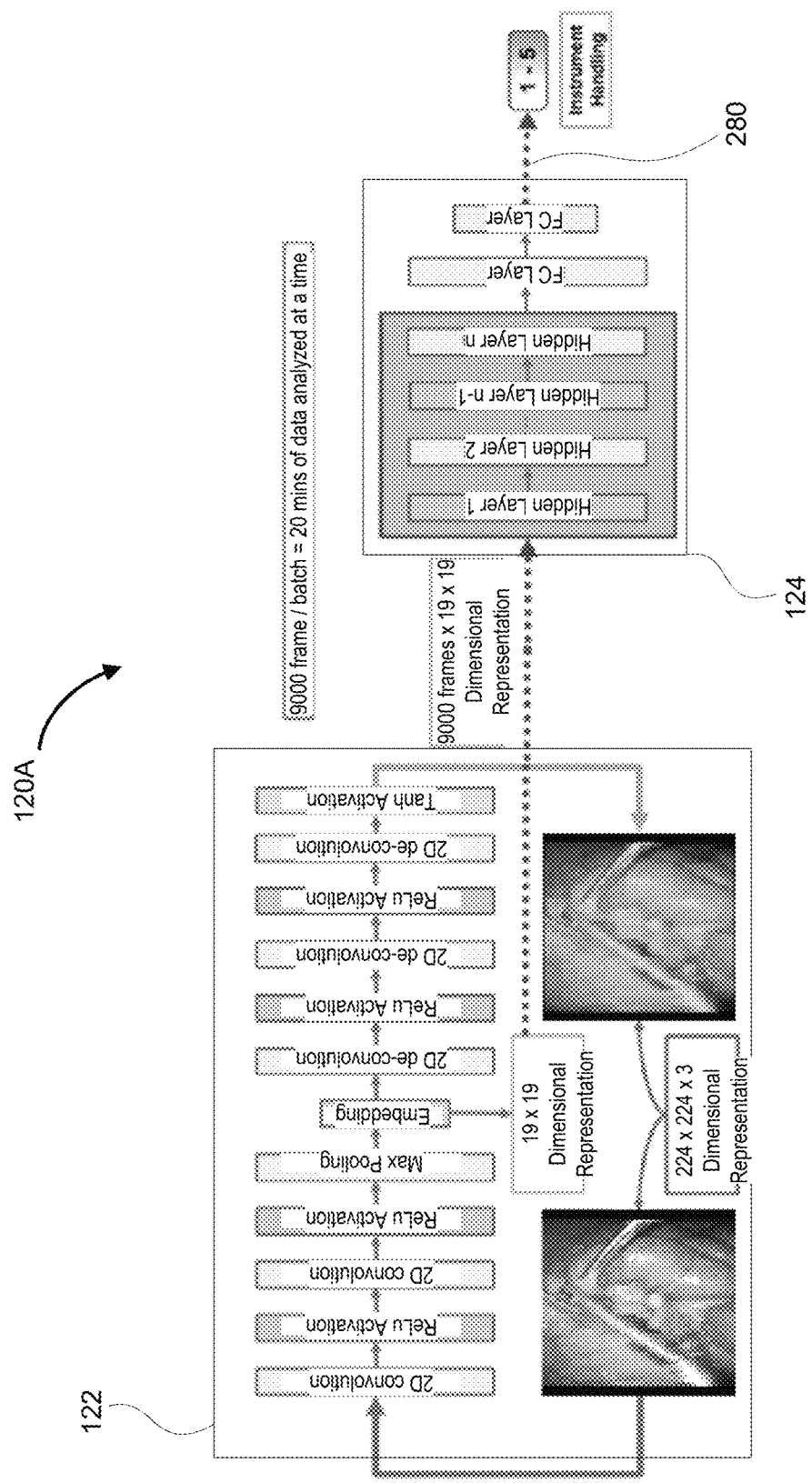
FIG. 2B illustrates an example of a latent representation analysis architecture, in accordance with some embodiments.

FIG. 2B shows an example MLA 120A which includes the dimensionality reduction architecture 122 and the sequential relation architecture 124 where the final layer of the sequential relation architecture 124 is configured to provide a value related to surgical instrument motion 280 which is indicative of instrument handling of the surgical instruments within the frames. For example, the sequential relation architecture 124 may have been trained with training data that teach the sequential relation architecture 124 to detect surgical instrument handling.

Figure 3:
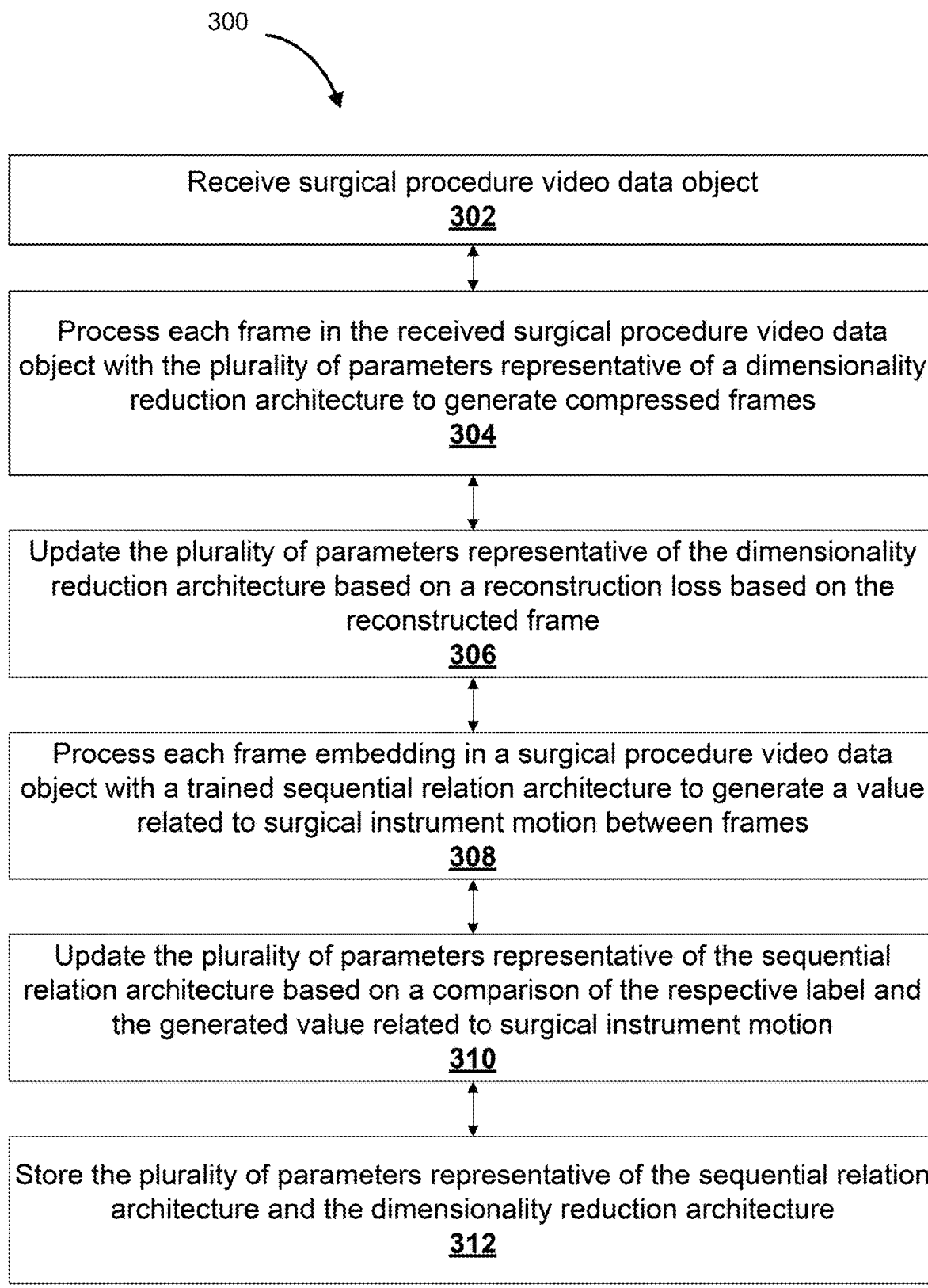
FIG. 3 illustrates, in a flowchart, an example of a method of assessing surgical performance with an example latent representation analysis architecture, in accordance with some embodiments.

Referring now to FIG. 3, a flowchart of an example of a method 300 of training an MLA 120A, within a first data set (e.g., a surgical procedure video data set) in accordance with some embodiments.

At step 302, the method 300 comprises receiving first data set which includes one or more surgical procedure video data sets. The surgical procedure video data set include a plurality of frames comprising at least one surgical instrument and label data for each of the one or more surgical procedure video data sets representative of surgical performance.

In example embodiments, surgical procedure video data set is a full surgical procedure video data set. In example embodiments, the surgical procedure video data set is a partially complete or streaming portion of a full surgical procedure video data set.

According to example embodiments, the MLA 120A receives a first data set which is one of Example 1 or 2 Datasets, described below:

Example 1 Dataset

In one non-limiting example, the first data set consists of 114 full length videos of minimally invasive surgical procedures that have been captured at 30 frames/sec. The full-length procedures were broken down into 20-minute segments which were rated by experienced clinical analysts using the OSATS template. 291 clips were extracted from this dataset. Since it was possible to extract multiple clips from the same video, the training, validation and test sets were created based on a unique ID assigned to each video. This was to ensure that the same case would not appear in more than one set. Each clip was then broken down into its constituent frames and the data was further sub-sampled by only including every fourth frame due to the similarity of adjacent frames.

Each set of 9,000 frames had an associated label consisting of seven integer values, each corresponding to a category on the OSATS global rating scale. These categories are been defined below. The laparoscopic videos used for the training of the models presented in this disclosure are property of Surgical Safety Technologies.

Example 2 Dataset

In one non-limiting example, the first data set consists of the JHU-ISI Gesture and Skill Assessment Working Set (JIGSAWS) dataset. These clips show curated table-top surgical setups and consists of kinematic and video data from surgeons performing five trials of surgical actions such as knot-tying, needle-passing, and suturing. The data was captured using Intuitive Surgical's DaVinci Robotic System and comes with manually annotated labels that correspond to performance scores as defined by a modified version of the Objective Structured Assessment of Technical Skills. The modified version of OSATS is called the Global Rating Score (GRS) and excludes categories such as Use of Assistants, as each clip is of a surgeon completing a short procedure in a controlled environment where assistance is not available. GRS uses a Likert scale with values ranging from 1-5 for the following categories: respect for tissue, suture/needle handling, time and motion, flow of operation overall performance, and quality of product.

JIGSAWS has a well-defined validation scheme that allows for structured comparison of novel algorithms. The scheme includes leave-one-supertrial-out (LOSO), where one trial out of five is removed from the dataset and used for validation for each procedure, and leave-one-user-out (LOUO). This scheme allows for an objective comparison of approaches.

In example embodiments, the first data set used to train dimensionality reduction architecture 122 includes a large collection of unannotated frames. Training the dimensionality reduction architecture 122 with a large collection of unannotated frames allows for unsupervised learning, and can ensure that the MLA 120A can create acceptable generalizations for frames across the range of available surgical procedure video data set in the first dataset.

In example embodiments, the first data set used to train the MLA 120A is augmented to increase the size of available training data. For example, the first data set frames may be augmented by the following methods: rotation of 90°, flip vertically, flip horizontally.

According to example embodiments where the Example 1 Dataset is used, the first data set may include 250,000 frames stochastically extracted from across the a dataset of clips that did not have a corresponding OSATS score assigned to it.

According to some scenarios, a training set (e.g., first data set) of 1,000,000 frames of which 15% were held out for the purpose of validation is used to train the dimensionality reduction architecture 122.

At step 304, the each frame in the received surgical procedure video data set is processed with the dimensionality reduction architecture 122 to generate a reconstructed frame (e.g., reconstructed frame 260) based on a compressed frame (i.e. embedding 270) incorporating surgical instrument characteristics in the respective frame (e.g., frame 250).

In example embodiments, the dimensionality reduction architecture 122 is configured to downsample frames of into the embedding 270 from a 720p resolution into a vector of size 19×19×1.

Figure 4:
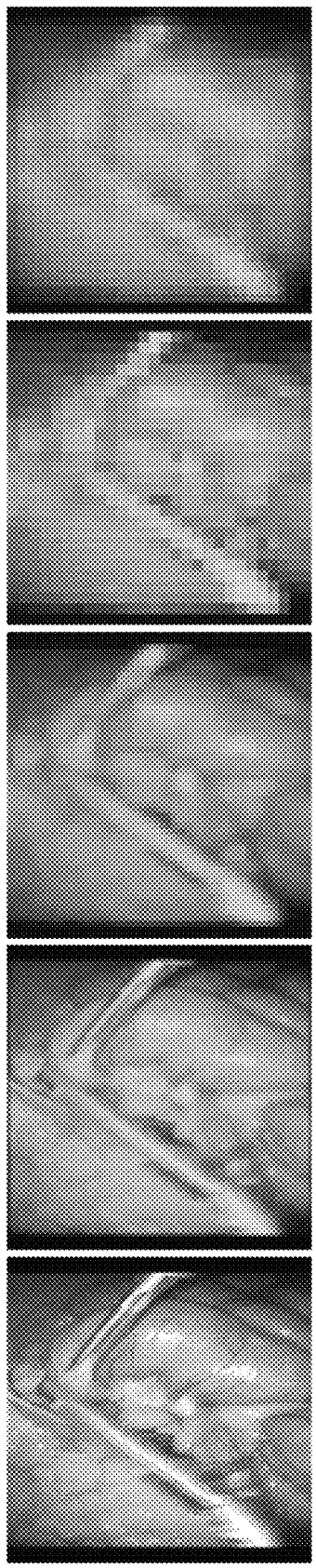
FIG. 4 illustrates and example of decoded reconstructions from a trained convolutional dimensionality reduction architecture, in accordance with some embodiments.

FIG. 4 illustrates an example of decoded reconstructions from a trained convolutional dimensionality reduction architecture 122, in accordance with some embodiments.

In FIG. 4, the aforementioned dataset of 291 clips was broken down and run through the encoder portion (i.e., the first portion) of the dimensionality reduction architecture 122 and the results captured in batches of 9000 frames. FIG. 4 shows the decreasing quality of images from left to right as the encoder was configured to generate embeddings 212 having progressively smaller embedding sizes.

Figure 5:
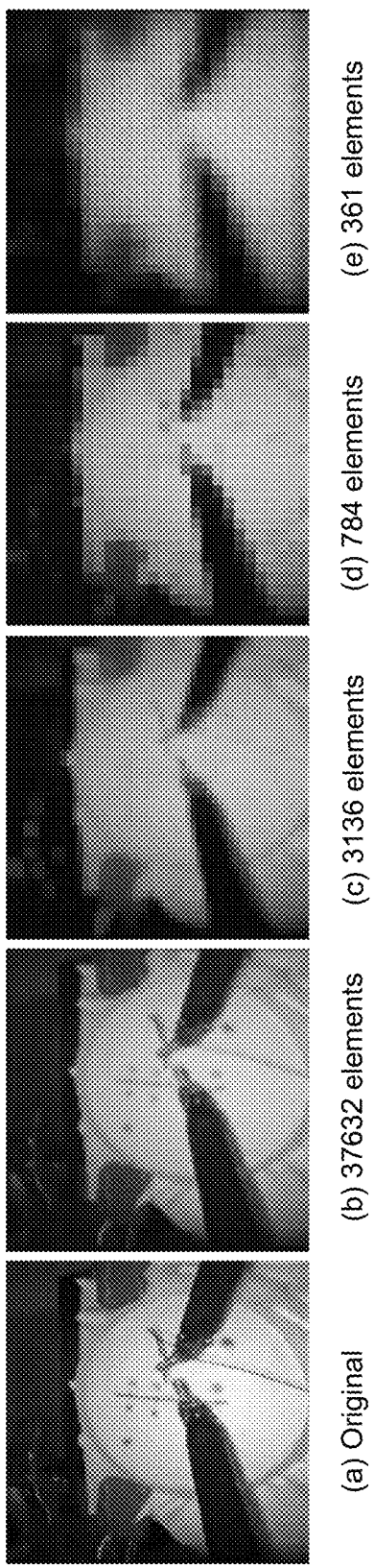
FIG. 5 depicts an image and images reconstructed from embeddings of different dimensions, in accordance with some embodiments.

FIG. 5 depicts an image and images reconstructed from embeddings 212 of different dimensions, in accordance with some embodiments. The 361-element embedding (the right most image) was used in subsequent analyses as it provides the context for the model to infer instrument related motion, and allows for training the model on available hardware.

When training the MLA 120A (either the dimensionality reduction architecture 122 or the sequential relation architecture 124, or both) can be configured to process surgical performance video data according to a variety of sampling schemes. For example, the dimensionality reduction architecture 122 can be trained using both the leave-one-supertrial-out (LOSO), where one trial out of five is removed from the dataset and used for validation for each procedure, and leave-one-user-out (LOUO) scheme. Tables 2 and 3 show the results of various sampling schemes used to train the MLA 120A.

In example embodiments, the dimensionality reduction architecture 122 is trained with a batch size of 10. Any batch size is contemplated, and batch size configuration can allow for more stability during training. For example, a batch size of 25 can be used to approximate each second of the video data.

In example embodiments, the dimensionality reduction architecture 122 is trained for 200 epochs. Any epoch duration is contemplated. For example, the dimensionality reduction architecture 122 can be trained for 150 epochs.

The dimensionality reduction architecture 122 may be configured with any sampling schemes, batch size, and training duration, and any combination of sampling schemes, batch size, and training duration.

An MLA 120A trained as described herein may outperforms state-of-the-art metrics in literature without using any kinematic data, as has been required in previous work. This may allows for the MLA 120A described herein to be used in any surgery, both open-view and laparoscopic.

At step 306, the plurality of parameters which define the dimensionality reduction architecture 112 are updated based on the reconstruction loss. In example embodiments, the reconstruction loss is assessed based on the number of incorrect pixels in the representation 260. In some embodiments, for example, the reconstruction loss is an L1 or L2 loss (alternatively referred to a Least Absolute Deviations and Least Square Errors loss).

The reconstruction loss may be based on an Adam optimizer processing the reconstructed representation 260 and the input frame. For example, the Adam optimizer may be used to dynamically update the gradient used to update the plurality of parameters representative of the dimensionality reduction architecture 112.

At step 308, the each embedding of each frame in the first data set is processed with the sequential relation architecture 124 to generate the value related to surgical instrument motion between frames 280. As described herein, the first data set may include the surgical performance video data used to train the dimensionality reduction architecture 112. In example embodiments, the first data set processed by the sequential relation architecture 124 is not the same surgical performance video data used to train the dimensionality reduction architecture 112, and is subsequently processed by the dimensionality reduction architecture 112 to generate respective embeddings 212 for processing with the sequential relation architecture 124. In example embodiments, the first data set is a subset of the surgical performance video data used to train the dimensionality reduction architecture 112.

In some embodiments, the value related to surgical instrument motion between frames 280 may represent at least one category associated to each frame in the video, and assigning a category score value to the video, where the total score value comprises a combination of each category score value. The at least one category may comprises at least one of tissue, instrument, time, motion, or use of an assistant.

At step 310, the plurality of parameters representative of the sequential relation architecture 124 are updated based on a comparison of the respective label assigned to the surgical performance video data object and the generated value related to surgical instrument motion 280. For example, where the generated value related to surgical instrument motion 280 indicates that the surgical performance shown in the video is a needle passing, where the video is shown to be knot tying, the plurality of parameters representative of the sequential relation architecture 124 may be updated by a first magnitude to train the sequential relation architecture 124.

Similar to the discussion set out regarding the dimensionality reduction architecture 112, the sequential relation architecture 124 may be configured with any sampling schemes, batch size, and training duration, and any combination of sampling schemes, batch size, and training duration.

At step 312, the trained plurality of parameters representative of the sequential relation architecture 124 and the dimensionality reduction architecture 122 are stored. In example embodiments, the trained plurality of parameters are stored in the memory 108.

In example embodiments, the plurality of parameters representative of the dimensionality reduction architecture 122 are stored after step 306. Although steps 302 to 312 are shown occurring sequentially, any order of the steps in method 300 is contemplated. For example, the embeddings 212 generated by the dimensionality reduction architecture 122 in step 304 can be used in step 308 by the sequential relation architecture 124 prior to the dimensionality reduction architecture 122 being completely trained.

Results

In an example embodiment, a flattened 19×19×1 dimensional embedding 212 was chosen for subsequent analysis. The data (e.g., Example 1 Dataset) was run through the encoder portion of the dimensionality reduction architecture 122 and the results are captured in batches of 900 frames. Then, the resulting batches were used to train the sequential relation architecture 124 shown in FIG. 2A.

The resource intensive nature of the training data made hyper-parameter tuning a challenge. The stability of the training was found to increase with a larger hidden dimension value and with a larger batch size. A hidden dimension of 2250 with the largest batch size of 7 yielded the most promising results.

A set of 3 full-length test videos were run through the model and the results captured in Table 1.

TABLE 1

Model accuracies on test data for a.) Latent representation analysis and b.) Key-point analysis; where i.) Prediction matches label exactly, ii.) Prediction is a close under-estimation of the actual value, iii.) Scores 3 & 4 are interchangeable

| Condition | Case A | Case B | Case C | Case D | Condition | Case A | Case B | Case C | Case D |
|---|---|---|---|---|---|---|---|---|---|
| i. | 0.29 | 0.31 | 0.58 | 0.32 | i. | 0.33 | 0.45 | 0.56 | 0.40 |
| ii. | 0.50 | 1.00 | 0.88 | 0.63 | ii. | 0.42 | 0.78 | 0.56 | 0.72 |
| iii. | 0.79 | 0.51 | 1.00 | 0.51 | iii. | 0.84 | 0.45 | 0.78 | 0.57 |
| (a) Latent representation analysis | | | | | (b) Key-point analysis | | | | |

The model prediction and the labels are plotted against each other over the length of the video in FIGS. 10A-10D.

In order to use the trained MLA 120A, in example embodiments surgical performance video data sets, which can be data sets used to train the MLA 120A, (i.e., the first data) are processed by the plurality of parameters representative of the dimensionality reduction architecture to generate a compressed frame incorporating surgical instrument characteristics in the respective frame.

The compressed frames are processed by the plurality of parameters representative of the sequential relation architecture to generate the value related to surgical instrument motion.

Alerts can be configured based on the value related to surgical instrument motion, where for example the value is indicative of poor performance.

Figure 6A:
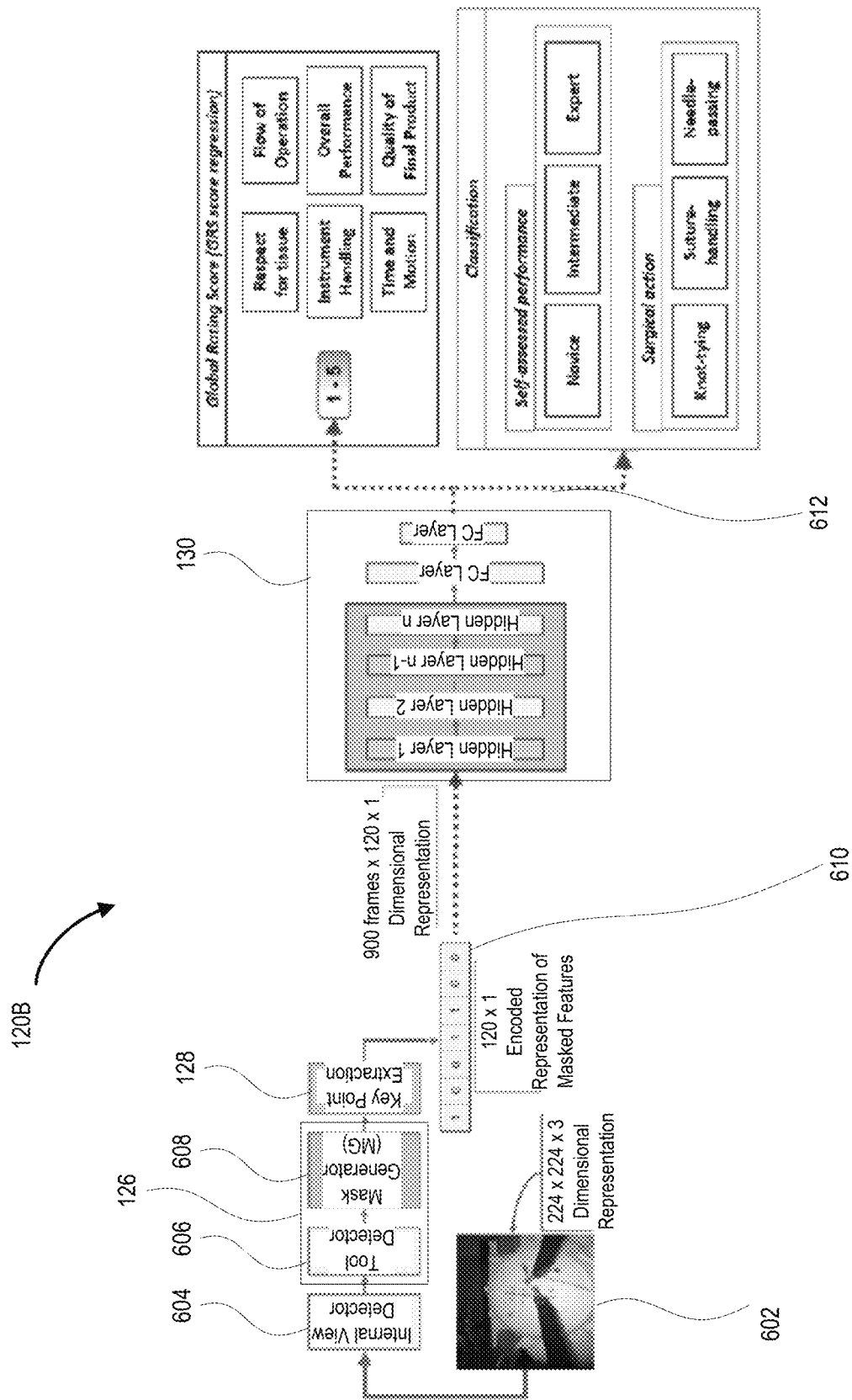
FIG. 6A illustrates an example of a key-point representation analysis architecture, in accordance with some embodiments.
Figure 6B:
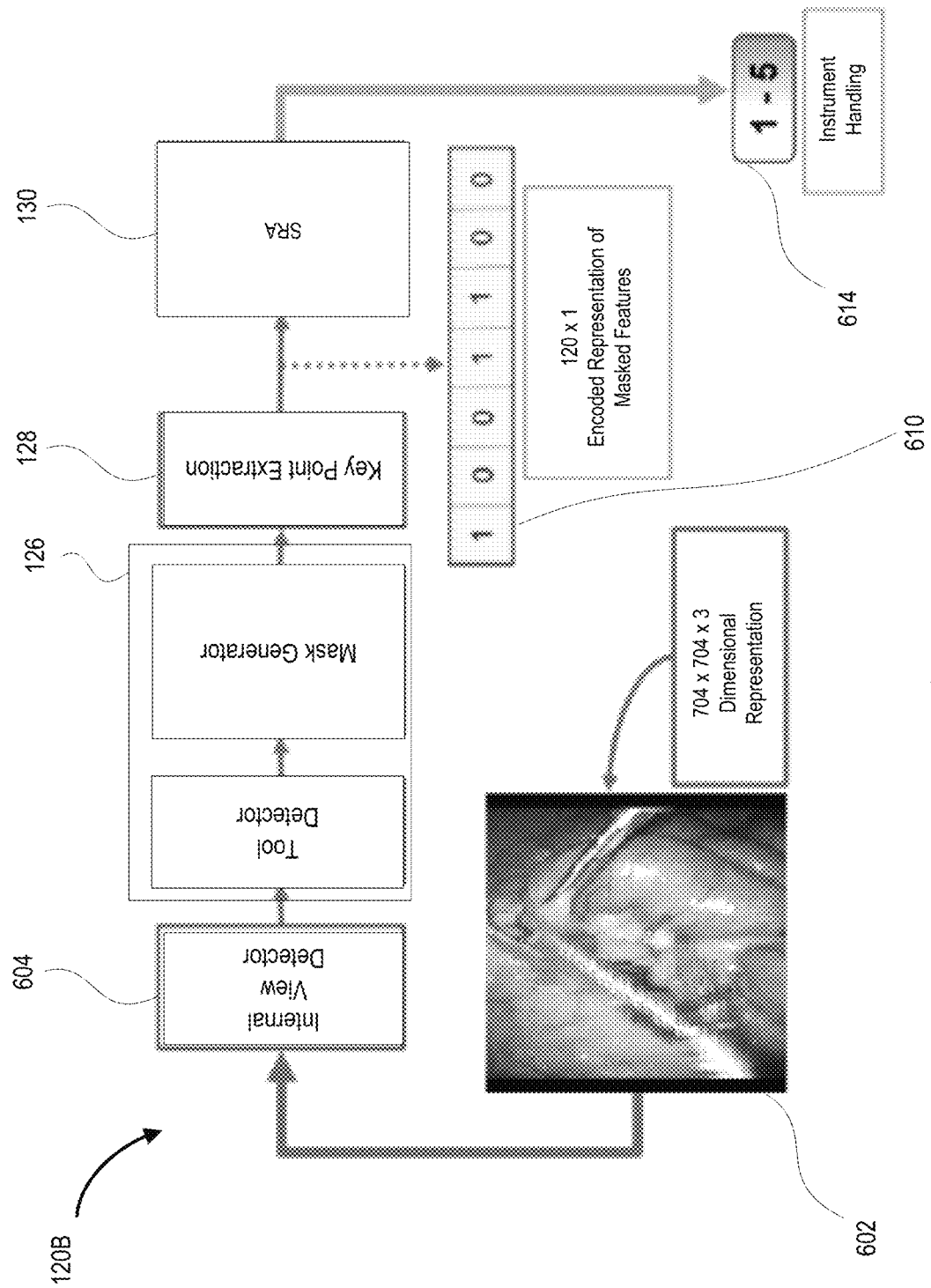
FIG. 6B illustrates an example of a key-point representation analysis architecture, in accordance with some embodiments.

FIGS. 6A and 6B show example embodiments of MLA 120B. The proposed end-to-end MLAs can be used as a classifier to predict surgical actions and self-reported skill and also as a regression model which predicts scores on the likert-scale for each GRS category.

In the embodiment shown in FIG. 6A, MLA 120B includes the surgical instrument instance segmentation architecture 126, the decomposition model 128, and the sequential relation architecture 130 processing the input frame 602 (e.g., a frame in a surgical procedure video data set which shows a laparoscopic procedure).

In the embodiment shown, the MLA 120B further includes an internal view detector 604 which processes each frame of the surgical procedure video data set. In example embodiments, the MLA 120B does not include the internal view detector 604, and frames are provided directly to the surgical instrument instance segmentation architecture 126.

In example embodiments, the internal view detector 604, is used to filter out frames that consist of content which is irrelevant to assessing surgical performance, such as an external view of the surgical staff. The internal view detector 604 can help in efficiently allocating computing resources, or increasing speed or accuracy as it can remove irrelevant frames, which may be a feature of the surgical performance video data object (e.g., the camera capturing the laparoscopic procedures will capture video data of it being inserted into and removed from the body multiple times during the surgery).

Figure 7:
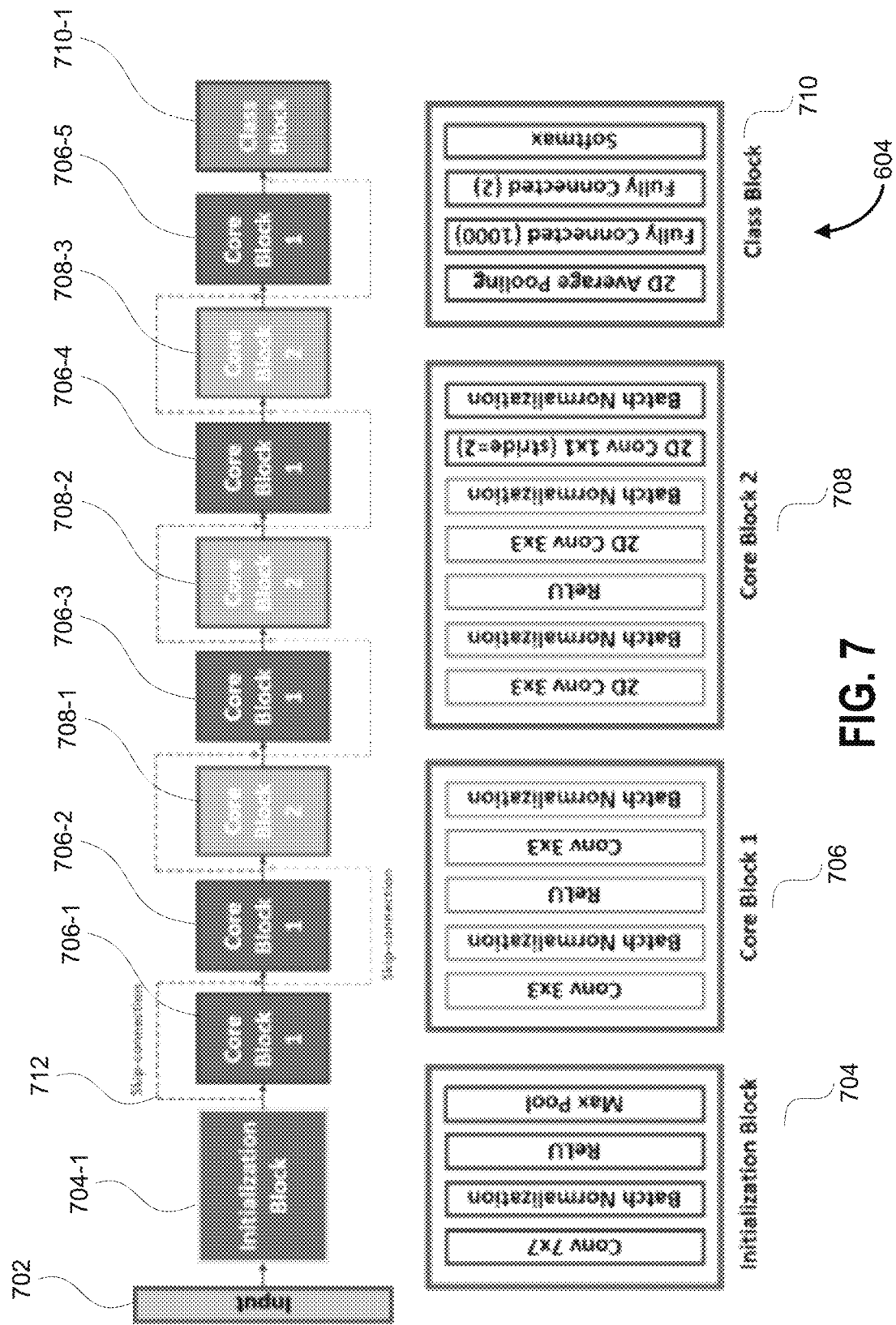
FIG. 7 illustrates an example interior view extractor architecture for internal/external classification, in accordance with some embodiments.

FIG. 7 shows an example embodiment of the internal view detector 604. In example embodiments, the internal view detector 604 includes a binary classifier based on a ResNet18 backbone.

In the embodiment shown, the internal view detector 604 includes an initialization block type architecture 704, a core block one type architecture 706, a core block two type architecture 708 and a class block one type architecture 710.

According to example embodiments, as skip connections between earlier and subsequent architectural elements is based on has the ability to capture both high-level and low-level data. Adding skip connections may improve training performance so by reducing gradient based errors (vanishing gradient) in long models such as a ResNet model.

FIG. 7 shows the internal view detector 604 as including the following arrangement of architectural elements to process the input 702:

An initialization block 704-1 processes the input and passes the processed information to both the subsequent core block one type architecture 706-1 and the core block one type architecture 706-2 via a skip connection.

The core block one type architecture 706-1 processes the received information (referred to hereinafter as output of 706-1) and passes the output to both the subsequent core block one type architecture 706-2 and the core block two type architecture 708-1 via a skip connection.

Similarly, as shown in FIG. 7, core block one type architecture 706-2 passes its processed output to both core block two type architecture 708-1 and core block one type architecture 706-3 via a skip connection.

Similarly, core block two type architecture 708-1 passes its processed output to both core block one type architecture 706-3 and core block two type architecture 708-2 via a skip connection.

Similarly, core block one type architecture 706-3 passes its processed output to both core block two type architecture 708-2 and core block one type architecture 706-4 via a skip connection.

Similarly, core block two type architecture 708-2 passes its processed output to both core block one type architecture 706-4 and core block two type architecture 708-3 via a skip connection.

Similarly, core block one type architecture 706-4 passes its processed output to both core block two type architecture 708-3 and core block one type architecture 706-5 via a skip connection.

Similarly, core block two type architecture 708-3 passes its processed output to both core block one type architecture 706-5 and class block type architecture 710-1 via a skip connection.

Finally, core block one type architecture 706-5 passes its processed output to class block type architecture 710-1.

In example embodiments, any combination of architecture types and skip patterns is contemplated.

Referring again to FIG. 6A, the surgical instrument instance segmentation architecture 126 of MLA 120B may include a tool detector 606 and a mask generator architecture 608 (e.g., Mask-RNN) to determine whether an instrument is present and to assign each pixel in the respective frame a likelihood of belonging to at least one surgical instrument to generate a respective mask for each surgical instrument, respectively, in the respective frame. Capturing the type of tool, its position and orientation in each frame are insights that can be acquired by modeling the problem as a semantic segmentation task (e.g., which outlines and labels regions in an image). Detecting tools and generating a mask can be configured as a semantic segmentation task by assigning each pixel in each frame a value for what tool it belongs to, and subsequently masks were generated that correspond to each visible tool.

The tool detector 606 may be configured to determine whether a surgical instrument is present in the frame the input frame 602. The tool detector 606 may act as a filter of varying specificity to determine whether a tool is present. For example, the tool detector 606 may prevent input frame 602 with only tissue showing in the frame from being passed on to Mask-RNN 608 to reduce computation load for the Mask-RNN 608.

The tool detector 606 may be a variant of a ResNet with or without skip connections. Any configuration of the tool detector 606 is contemplated.

The mask generator architecture 608 (hereinafter referred to as Mask-RNN 608, and shown as MG 608 in FIG. 6A) assigns a pixel level likelihood of each pixel within the input frame 602 of belonging to a surgical instrument. In example embodiments, the Mask-RNN 608 may be configured to assign a pixel level likelihood of each pixel within the input frame 602 of belonging to a surgical instrument where the Mask-RNN 608 determines that on a balance of probabilities the pixel belongs to a surgical instrument. Segmenting a frame at pixel level can for example allow an analysis of orientation of the instrument.

The Mask-RNN 608 generates a mask based on the pixel level likelihood of each pixel within the input frame 602 of belonging to a surgical instrument. For example, the mask may generate a set having binary coordinates representative of a mask, wherein a non-zero coordinate is indicative of a mask.

A challenge of Mask-RNN 608 generating an accurate mask of surgical can include in fine-tuning Mask-RNN 608 as it requires, what is considered to be, an exorbitant amount of training data especially if Mask-RNN 608 is generalized to all surgical videos.

In example embodiments, the Mask-RN N 608 may include separate loss functions that are minimized during training for classifying the type of surgical instrument and generating the mask. For example, the Mask-RNN 608 may have a first loss which is a classifier loss which predicts what class the mask belongs to and a second loss which attempts to refine the pixel area covered by the mask.

In example embodiments, the plurality of parameters which define the Mask-RNN 608 are pre-trained with previous data sets (e.g., a pre-trained mask generator architecture) prior to processing the information resulting from the input frame 602. For example, the surgical instrument instance segmentation architecture may be the Mask-RNN 608 pre-trained on the COCO dataset, or pre-trained on openly available datasets in non-medical domains. This can be beneficial, as the Mask-RNN 608 does not have to be trained from scratch.

In example embodiments, the pre-trained Mask-RNN 608 may further be trained based on the information resulting from the input frame 602 (i.e., "fine tuned" for generating surgical instrument masks). For example, the pre-trained Mask-RNN 608 may subsequently be further trained with a data set which includes surgical instruments by freezing a fixed number of layers (represented by a plurality of interconnected parameters) of the mask generator machine learning architecture to focus the mask generator machine learning architecture on a reduced number of mask types.

In example embodiments, to prevent overloading available computing resources, the pre-trained Mask-RNN 608 of the surgical instrument instance segmentation architecture 126 may have every layer therein frozen, and a final layer modified to have only outputs indicative of surgical instruments or surgical instruments characteristics or classifications. For example, the final layer may limit the pre-trained Mask-RNN 608 to predicting one of 80 surgical instruments, or other instruments. Subsequent training of the pre-trained Mask-RNN 608 based on input surgical performance video data may teach the pre-trained Mask-RNN 608 to more accurately identify surgical instruments.

The decomposition model 128 may processes the masks received from the surgical instrument instance segmentation architecture 126 to generate key point mask characteristics based on extracting surgical instrument characteristics for each mask in the respective frame.

The decomposition model 128 may capture certain characteristics of the surgical instruments that appear within each processed frame 602. Instead of extracting representations of the data, the decomposition model 128 encodes the spatial characteristics of the surgical instruments (e.g., tools) appearing in each frame 602, which may ensure standardization. In contrast, a manual review process requires skilled analysts to rate the performance of surgical teams using videos of minimally invasive procedures. In doing so, they are required to follow a set of guidelines to ensure standardization of the rating process across different procedures and different analysts. For most practical applications, this is difficult to achieve.

The decomposition model 128 may be trained to create a fixed length encoded low dimensional representation vector 610 (alternatively referred to as key point mask characteristics 610) from extracted frame-level key-point data.

The key point mask characteristics 610 can include geometric characteristics extracted for each mask. In example embodiments, the key point mask characteristics 610 include a mask centroid, a position of the centroid or other reference point of the surgical instrument, size, length and orientation, and generally the degrees of freedom representing the mask (where a line represents the mask, for example).

Any number of key point mask characteristics 610 can be used to represent the surgical instrument mask. In example embodiments, the key point mask characteristics 610 is a 120-element vector, with 5 elements used to represent each instrument in each frame. In some embodiments, the key point mask characteristics can include color, size, and so forth.

Figure 8:
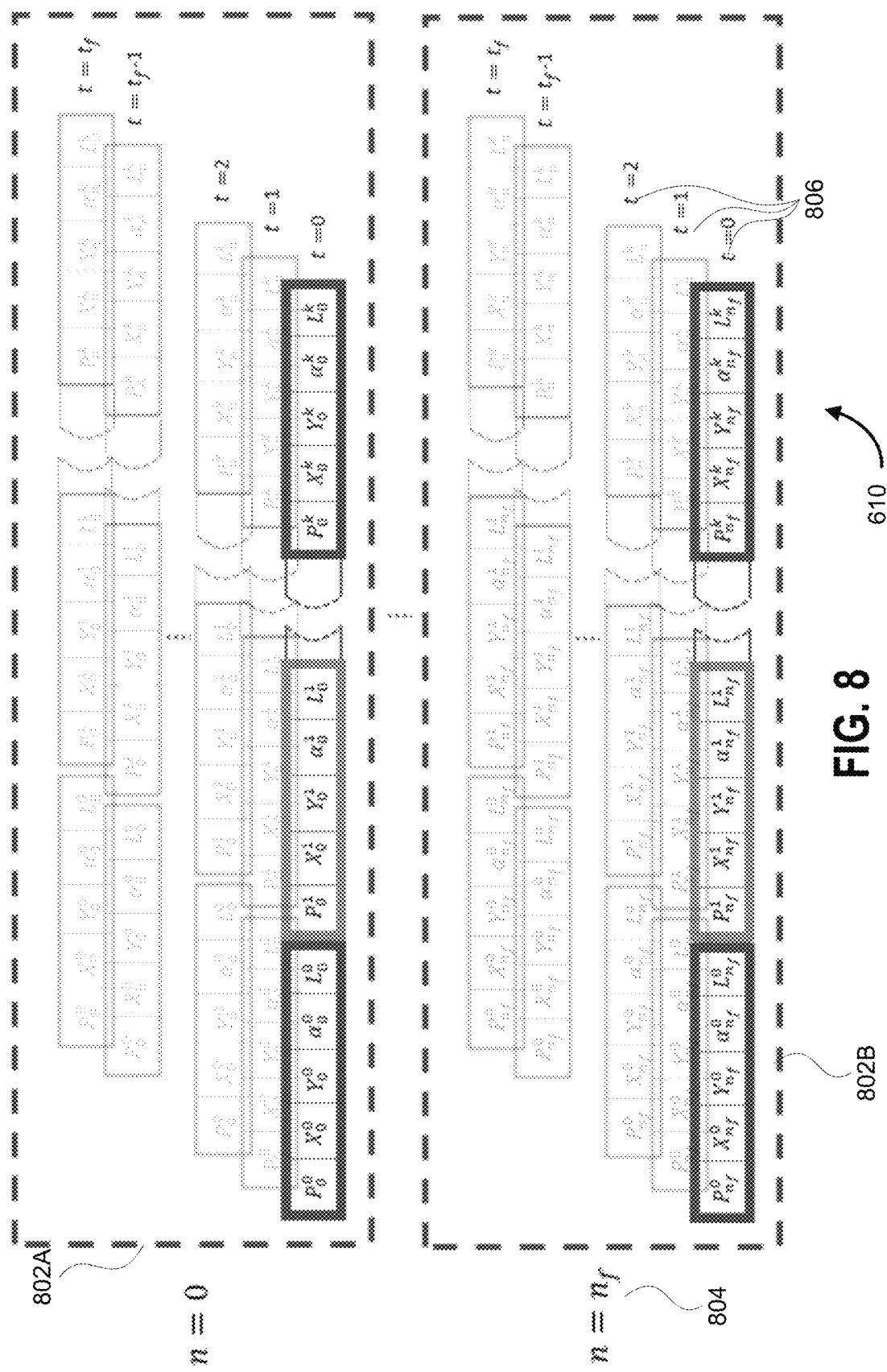
FIG. 8 illustrates an example of a visual representation of a key-point feature vector, in accordance with some embodiments.

Referring now to FIG. 8, an example of a visual representation of key point mask characteristics 610 is shown. $n_f$ 802 refers to the total no. of batches for training (two key point mask characteristics 610 (802A and 802B) are shown in FIG. 8 corresponding to the same key point mask characteristics 610 being updated as successive frames are processed); $t_f$ 806 refers to the no. of time-steps in each batch; k refers to the total no. of expected instruments in the frames. For the purposes of the herein disclosure, k=1; P, X, Y, α, & L, correspond to presence of instrument, x and y coordinates of a point on the segmented mask, orientation of the tool in radians, and the length of the visible instrument in mm.

Algorithm 1 (below) describes an example process of calculating these values. In the example of Algorithm 1, the key point mask characteristics 610 are configured to represent the generated mask(s) as line objects, to reduce the amount of information processed by the sequential relation architecture 130. This approach may be advantageous where the tools have geometries and functions which are captured well with a line representation, for example a needle. In example embodiments, key point mask characteristics 610 are configured to represent the generated mask(s) as any type of geometry (2D or 3D or otherwise), and features that result from the more complex geometries. For example, a 3D object may include at least 6 key point mask characteristics 610 representing each degree of freedom that the object experiences. In another non-limiting example, a 2D object may include key point mask characteristics 610 which include a second largest eigenvalue'd eigenvector which is used to calculate a predicted width or size of the surgical instrument.

| Algorithm 1 Instrument Key-Point Calculation | |
|---|---|
| 1: | Inputs: Mask $\mathcal{M}$ |
| 2: | for frame = 0 to n do |
| 3: |    for mask = 0 to m do |
| 3: |       Initialize {x, y} ← non-zero coordinates of mask |
| 3: |       $\mathcal{C}$ = cov({x, y}) |
| 3: |       {$E_{value}$, $E_{vector}$} = ED($\mathcal{C}$); Eigenvalue Decomposition |
| 3: |       $v_0, w_0$ ← $E_{vector}$[0]; Eigenvector corresponding to the direction of largest variance |
| 3: |       $v_1, w_1$ ← $E_{vector}$[1]; Eigenvector corresponding to the direction of $2^{nd}$ largest variance |
| 3: |       ε = Contours($\mathcal{M}$); Mask contour extraction |
| 3: |       q = M(ε); Moments calculation |
| 3: |       X = $q_{10}/q_{00}$; Centroid (X) |
| 3: |       Y = $q_{01}/q_{00}$; Centroid (Y) |
| 3: |       α = atan($w_0, v_0$); Instrument Orientation |
| 3: |       $\mathcal{L}$ ← $\mathcal{F}$(X, Y, α); Length of mask is calculated using mask characteristics |
| 4: |    end for |
| 5: | end for |

In Algorithm 1, in step 1 the mask (e.g., a plurality of locations on the frame having an associated binary value, either part of the mask or not part of the mask) is received.

In the example of a circle mask, each of the points on this circle to get a set of x, y points, and the range of points x and the range of points y would be the same. In examples including masks with complex 2D geometries, a coordinate system is established and each point on this blob is assigned an x-value and a y-value.

For each frame which has a mask (step 2), and for each mask in each frame (step 3), the covariance matrix for the mask is determined for each mask pixel (i.e., a square matrix giving the covariance between each (coordinates of the mask in the frame) of the mask pixel vector).

The covariance matrix (which may be square) for each mask is subsequently mathematically decomposed into a set of eigenvectors and eigenvalues. Each eigenvector of the covariance matrix satisfies the eigenvalue equation.

The eigenvectors corresponding to the largest variance (i.e. the largest eigenvector) (and in example embodiments the second largest variance (i.e., the second largest eigenvector), etc.) are extracted from the decomposition of the mask into a set of eigenvectors and eigenvalues.

In Algorithm 1, the largest variance (i.e. the largest eigenvalue'd eigenvector) is used to determine the orientation of the mask, and the contours are used to determine the centroid of the mask itself.

Generally, the larger the eigenvalue, the more the distribution of points in the mask act in the direction of the eigenvector that the eigenvalue corresponds to. For a 2D mask, the largest eigenvalue'd eigenvector points in the direction that the values are most widely distributed in and the next eigenvector corresponds to a direction that is exactly perpendicular to the direction of the first eigenvector.

In the example of a 2D circle, there would not be a largest eigenvalue'd eigenvectors as all the eigenvectors would have the same eigenvalue. This implies that there is no "direction" to the circle.

In the example embodiment where the mask is a rectangular mask, the range points along a side that the rectangular mask is longest will be larger than the perpendicular smaller side (absent the rectangle being a square). For example, if the rectangular mask has a width=x=2 and a height=y=50, the range of points for y will be [0,50] and that of x will be [0,2]. This range, captured by the eigenvector, gives a sense of where the object "points".

In examples including masks with complex geometries, eigenvalue decomposition results in a pair of values {eigenvalue, eigenvector}, similarly sorted based on the eigenvalues.

At step 3, based on the non-zero values of the mask, the contours of the mask can be extracted by determining the boundary between mask and non-mask pixels.

The centroid, and the orientation of the mask, can used to determine a length of the mask, for example where the surgical instrument is represented by a line.

In example embodiments, the second largest eigenvalue'd eigenvector is used to determine a size of the instrument. This second vector can be advantageously used to represent masks represented by 2D shapes, for example a rectangle. In some embodiments, for example where the surgical instrument is represented by a line, the second largest eigenvalue'd eigenvector is not used.

In some embodiments, for example, in order to create the decomposition model 128, a preliminary analysis was done to ensure that the newly annotated segmentation data would yield acceptable results.

The acceptability of the result depends on the ability of the decomposition model 128 to precisely create segmentations and associate to those segmentations the correct instrument. A series of incorrect detections and classifications across the videos would yield key point mask characteristics 610 with inconsistent values which would make it difficult for the sequential relation architecture 130 classifier to learn temporary coherencies from the input data. In some embodiments, for example, the Mask-RCNN 608 pre-trained on the COCO dataset alleviated this issue.

The sequential relation architecture 130 can be similarly trained as described with respect to sequential relation architecture 124 to processing the key point mask characteristics 610 in each frame to generate the value related to surgical instrument motion 612 (e.g., a temporal coherency related to the motion of the surgical instrument). For example, the key point mask characteristics 610 can be used to train the sequential relation architecture 130 for extracting temporal insights and assigning a score for the OSATS categories under consideration.

Similar to sequential relation architecture 124, sequential relation architecture 130 can generate the value related to surgical instrument motion 612 which is representative of a GRS score, or a classification, or instrument handling (as shown in FIG. 6B by the value related to surgical instrument motion 614).

Similar to sequential relation architecture 124, sequential relation architecture 130 can be trained using the Adam optimizer with batch sizes ranging from 5 to 20.

Similar to the dimensionality reduction architecture 122, any constituent element of the MLA 120B may be configured with any sampling scheme, batch size, and training duration, and any combination of sampling scheme, batch size, and training duration.

Figure 9:
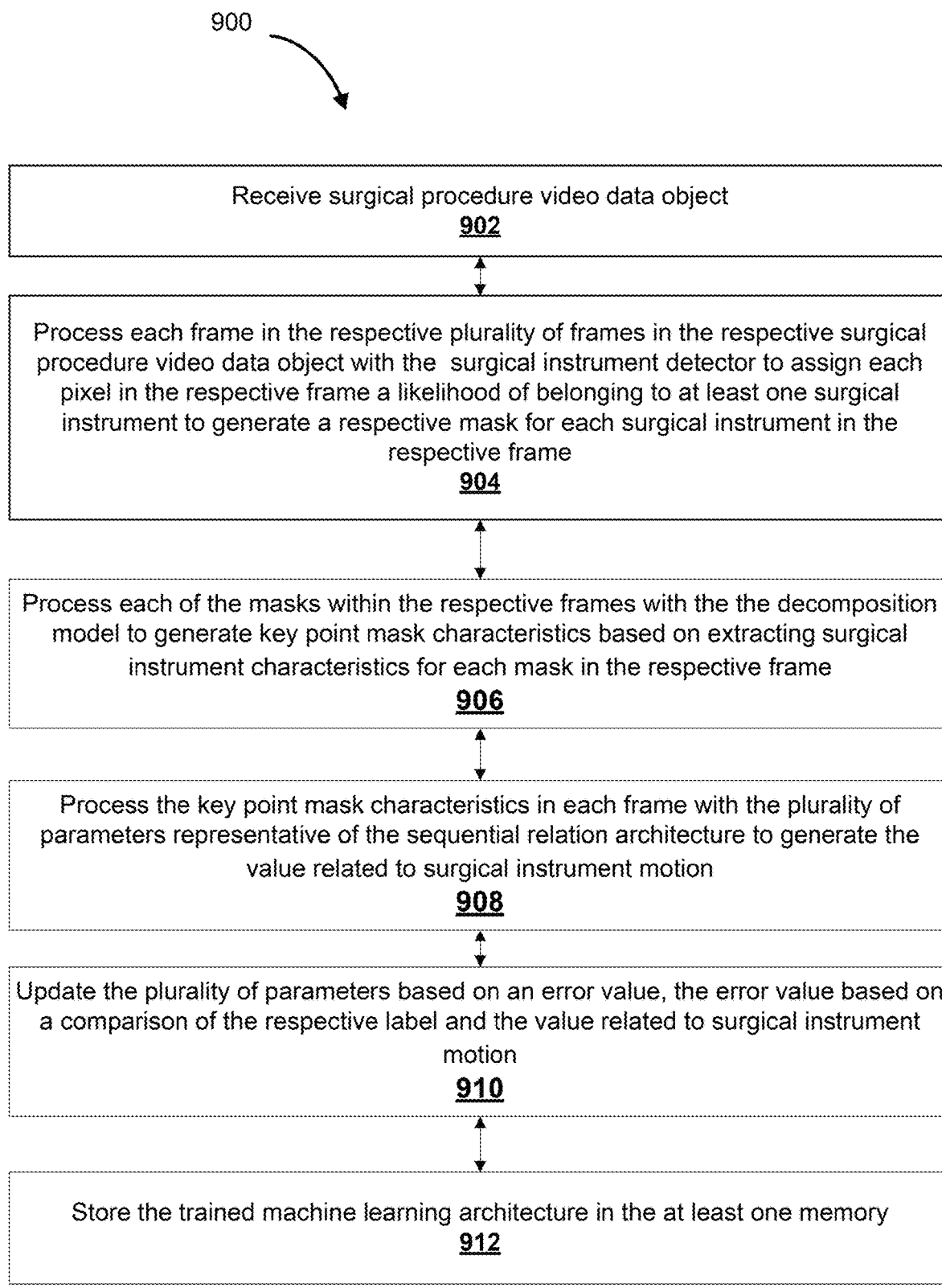
FIG. 9 illustrates, in a flowchart, an example of a method of assessing surgical performance with an example latent representation analysis architecture, in accordance with some embodiments.
Figure 10A:
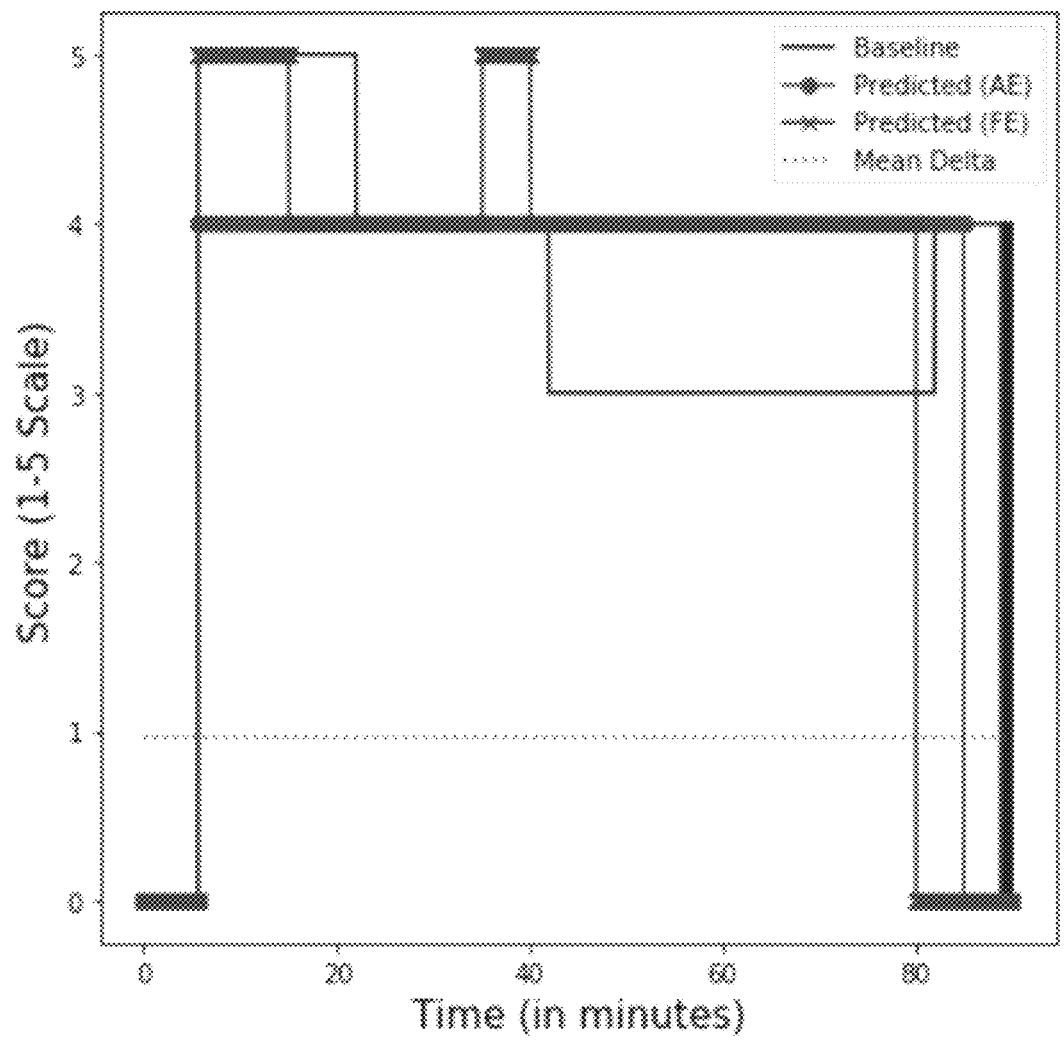
FIGS. 10A-10D illustrates an example of predicted vs. annotated OSATS scores for the latent representation analysis, in accordance with some embodiments.
Figure 10B:
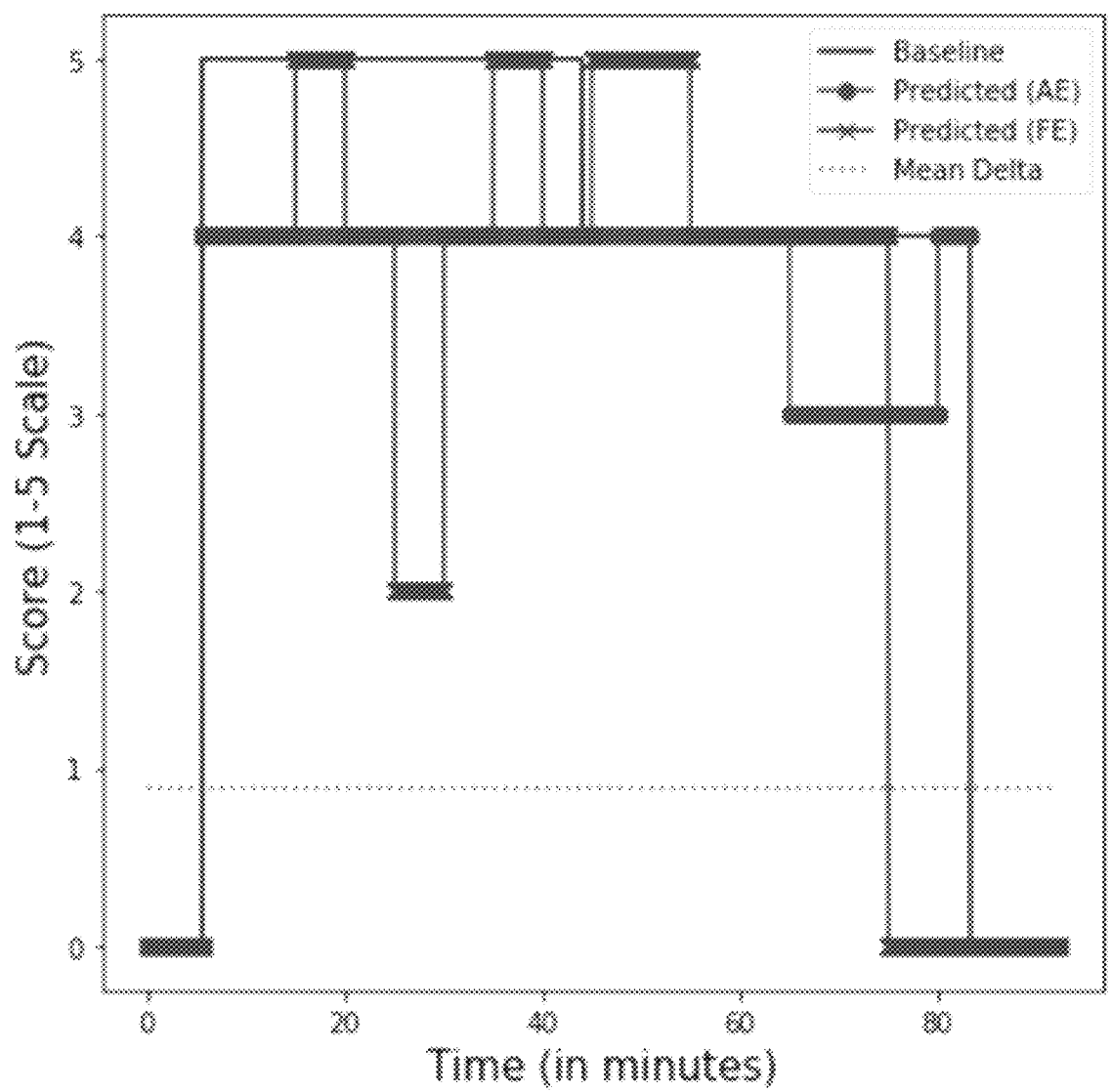
Figure 10C:
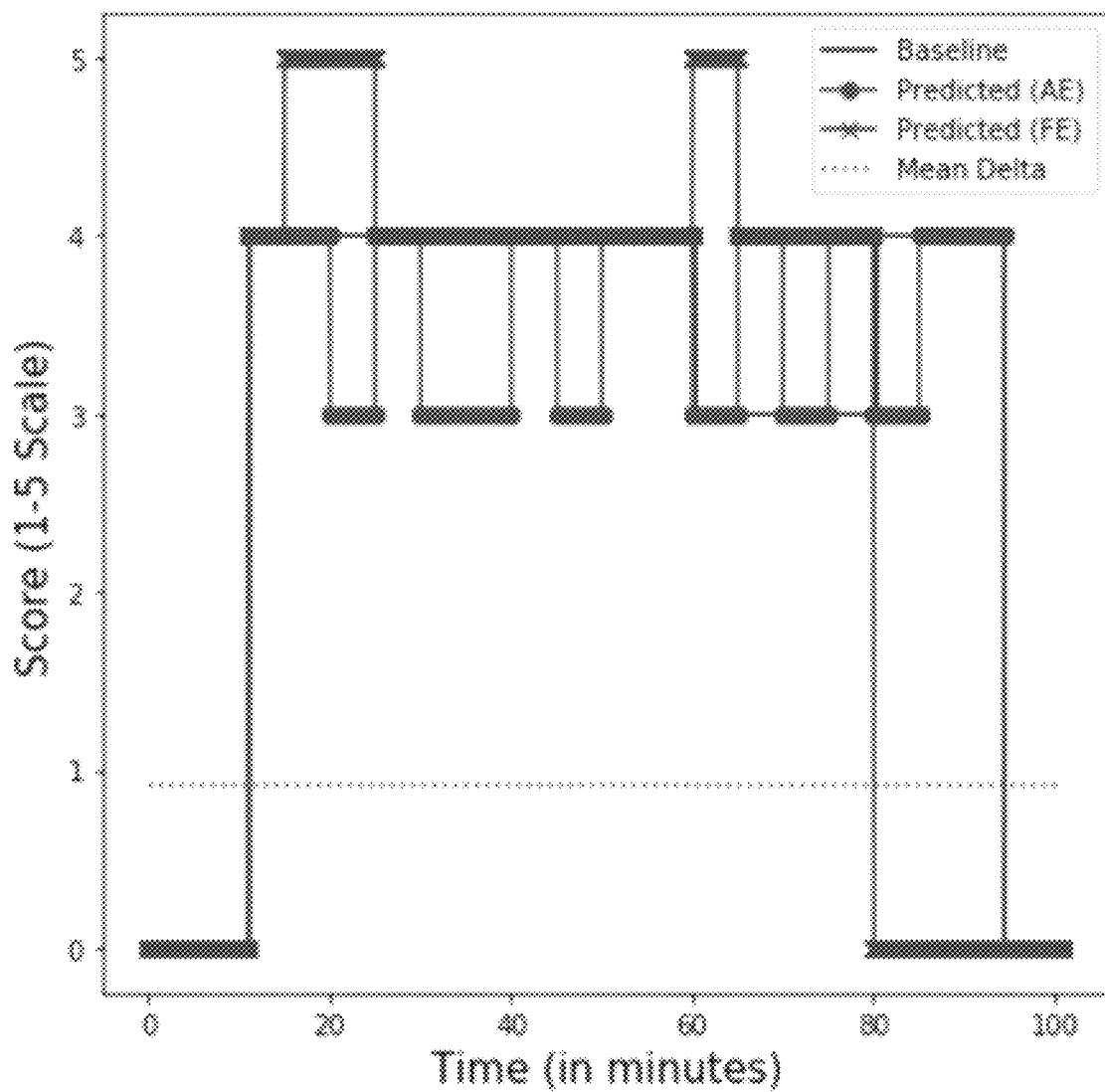
Figure 10D:
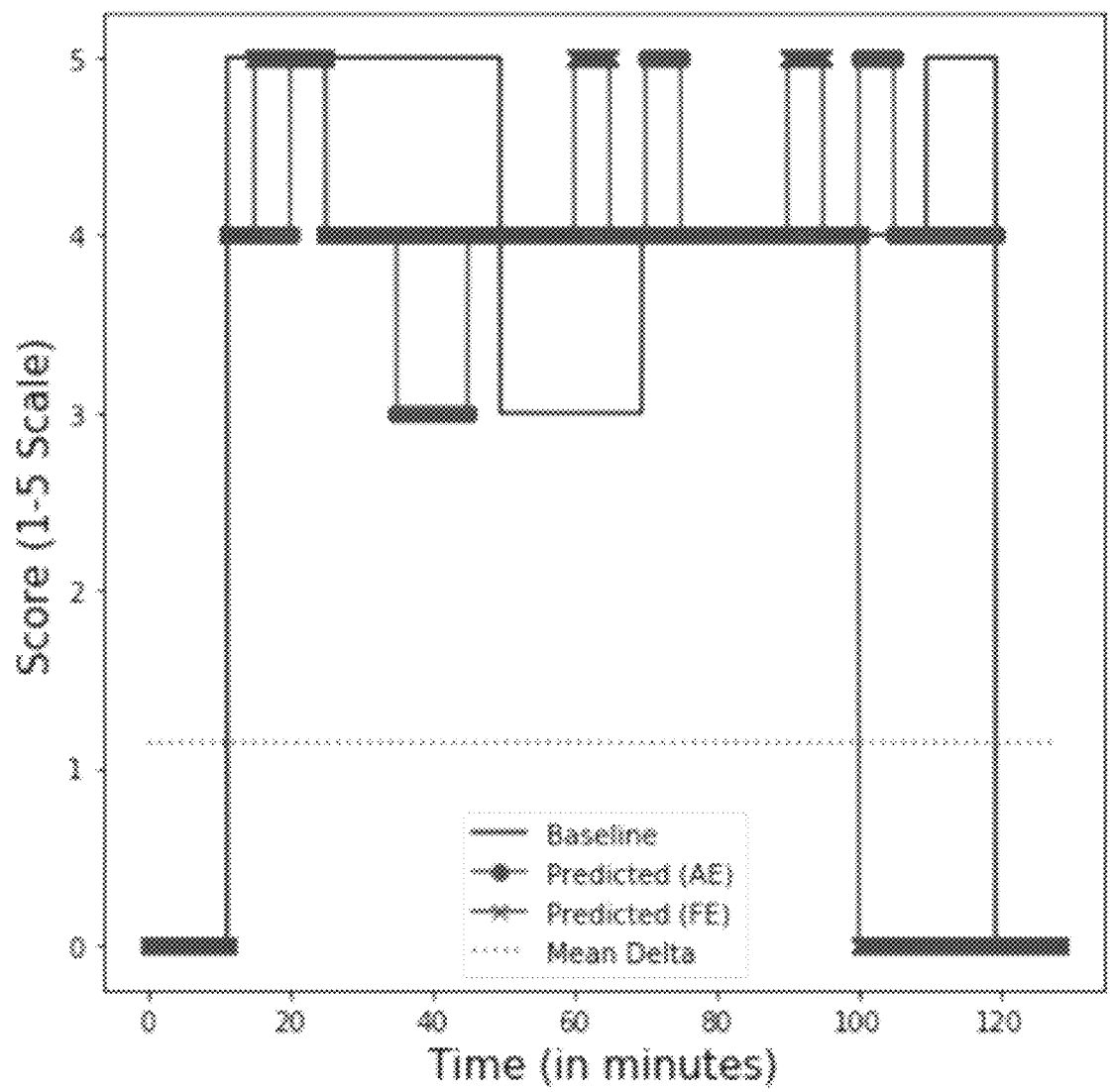

Referring now to FIG. 9, a method 900 of training the MLA 120B is shown.

At step 902, surgical procedure video data set (e.g., the first data set) are received. The surgical procedure video data set include a plurality of frames comprising at least one surgical instrument and label data for each of the one or more surgical procedure video data sets representative of surgical performance.

In example embodiments, surgical procedure video data set is a full surgical procedure video data set. In example embodiments, the surgical procedure video data set is a partially complete or streaming portion of a full surgical procedure video data set.

In example embodiments, the received surgical procedure video data set are processed prior to being used to train the MLA constituent elements. For example, certain tools are very likely to appear as they are very common and more than one of them can exist in a frame at once. These frames can be augmented by applying the following transformations: rotation 90°, flip vertically, flip horizontally.

According to example embodiments, the first data set can include a training set of 16,000 frames of which 30% were held out and split evenly to create the validation and test sets.

At step 904, each frame in the respective plurality of frames in the respective surgical procedure video data set with is processed with the surgical instrument instance segmentation architecture 126 to assign each pixel in the respective frame a likelihood of belonging to at least one surgical instrument to generate a respective mask for each surgical instrument in the respective frame.

Optionally, as a precursor to step 904, the pre-trained Mask-RCNN 608, on example embodiments, is fine-tuned with a prepared and segmented set of images (e.g., a set of 4180 images). The prepared and segmented set of images can be as balanced as possible with an approximately equal number of examples for each surgical instrument.

At step 906, each of the masks within the respective frames is processed with the decomposition model 128 to generate key point mask characteristics 610 based on extracting surgical instrument characteristics for each mask in the respective frame.

At step 908, key point mask characteristics 610 in each frame are processed with the plurality of parameters representative of the sequential relation architecture 130 to generate the value related to surgical instrument motion 612.

At step 910, the plurality of parameters of any one or any combination of the surgical instrument instance segmentation architecture 126, the decomposition model 128, and the sequential relation architecture 130 are updated based on a loss value, the loss value based on a comparison of the respective label and the value related to surgical instrument motion 610. For example, where a pre-trained surgical instrument instance segmentation architecture 126 is used which will not be fine tuned, the plurality of parameters representative of the surgical instrument instance segmentation architecture 126 are not updated. In another example, the plurality of parameters of the surgical instrument instance segmentation architecture 126, the decomposition model 128, and the sequential relation architecture 130 are updated.

At step 912, the trained MLA 120B, including the plurality of parameters updated based on the first data set, is stored in the at least one memory 108, for example.

In order to use the trained MLA 120B, in example embodiments surgical performance video data sets, which can be data sets used to train the MLA 120A, (i.e., the first data) are processed by the plurality of parameters representative of the surgical instrument instance segmentation architecture to assign each pixel in the respective frame a likelihood of belonging to at least one surgical instrument to generate a respective mask for each surgical instrument in the respective frame.

Each of the generated masks within the respective frames is processed with the plurality of parameters representative of the decomposition model to generate key point mask characteristics based on extracting surgical instrument characteristics for each mask in the respective frame.

The key point mask characteristics in each frame is processed with the plurality of parameters representative of the sequential relation architecture to generate the value related to surgical instrument motion.

Alerts can be configured based on the value related to surgical instrument motion, where for example the value is indicative of poor performance.

TABLE 2

Surgical task recognition literature review

| Group | Data | Scheme | Model | Metric | Surgical Tasks | | |
|---|---|---|---|---|---|---|---|
| | | | | | ST | KT | NP |
| Gurcan et al. [10] | K | Holdout | MS-RNN | A | 0.90 (0.08) | 0.90 (0.08) | 0.90 (0.08) |
| Sarikaya et al. [23] | K | Holdout | Optical flow | A | 0.91 (0.01) | 0.88 (0.03) | 0.74 (0.04) |
| Tao et al. [26] | K | LOSO | Sparse HMM | A | 0.81 | 0.76 | 0.83 |
| | | LOUO | Sparse HMM | A | 0.68 | 0.59 | 0.66 |
| DiPietro et al. [4] | K | LOUO | bi-LSTM | A | 0.83 | 0.83 | 0.83 |
| Sefati et al. [24] | K | LOUO | SC-CRF | A | 0.80 | 0.79 | 0.75 |
| Forestier et al. [6] | K | LOSO | DIP | A | 0.94 | 0.93 | 0.81 |
| | | LOUO | DIP | A | 0.88 | 0.90 | 0.75 |
| Gao et al. [8] | K | LOSO | AS-DTW | P | 0.93 (0.1) | 0.93 (0.1) | 0.93 (0.1) |
| | | | | R | 0.93 (0.1) | 0.93 (0.1) | 0.93 (0.1) |
| | | | | F1 | 0.92 (0.1) | 0.92 (0.1) | 0.92 (0.1) |
| | | LOUO | AS-DTW | P | 0.91 (0.1) | 0.93 (0.1) | 0.91 (0.1) |
| | | | | R | 0.90 (0.1) | 0.90 (0.1) | 0.90 (0.1) |
| | | | | F1 | 0.89 (0.1) | 0.89 (0.1) | 0.89 (0.1) |
| Lea et al. [16] | V | LOUO | ST-CNN +Seg | A | 0.82 | 0.82 | 0.82 |
| Tao et al. [26] | V | LOSO | BoSTF | A | 0.85 | 0.72 | 0.84 |
| | | LOUO | BoSTF | A | 0.76 | 0.62 | 0.79 |
| Lin et al. [18] | V | LOUO | TCN | A | 0.82 | 0.82 | 0.82 |
| Latent Repr. Analysis | V | LOSO | bi-LSTM (attention) | A | 0.97 (0.03) | 0.97 (0.03) | 0.97 (0.03) |
| | | | | P | 1.00 (0.00) | 0.99 (0.01) | 0.91 (0.11) |
| | | | | R | 0.94 (0.08) | 1.00 (0.00) | 0.99 (0.01) |
| | | | | F1 | 0.97 (0.04) | 0.99 (0.01) | 0.95 (0.06) |
| | | LOUO | bi-LSTM (attention) | A | 0.84 (0.20) | 0.84 (0.20) | 0.84 (0.20) |
| | | | | P | 1.00 (0.00) | 0.92 (0.22) | 0.75 (0.43) |
| | | | | R | 0.88 (0.21) | 1.00 (0.00) | 0.70 (0.42) |
| | | | | F1 | 0.92 (0.14) | 0.94 (0.17) | 0.72 (0.42) |
| Key-point Repr. Analysis | V | LOSO | bi-LSTM | A | 0.36 (0.04) | 0.36 (0.04) | 0.36 (0.04) |
| | | | | P | 1.00 (0.04) | 0.01 (0.04) | 0.01 (0.01) |
| | | | | R | 1.00 (0.25) | 0.35 (0.17) | 0.32 (0.13) |
| | | | | F1 | 1.00 (0.18) | 0.13 (0.07) | 0.03 (0.01) |

TABLE 3

Surgical skill assessment literature review

| Group | Data | Scheme | Model | Metric | Surgical Skill | | |
|---|---|---|---|---|---|---|---|
| | | | | | N | I | E |
| Wang et al. [30] | K | LOSO | CNN | A | 0.93 | 0.89 | 0.85 |
| | | | | F1 | 0.94 | 0.75 | 0.93 |
| | | Holdout | CNN | F1 | 0.95 | 0.77 | 0.94 |

TABLE 3-continued

Surgical skill assessment literature review

| Group | Data | Scheme | Model | Metric | Surgical Skill N | I | E |
|---|---|---|---|---|---|---|---|
| Latent Repr. Analysis | V | LOSO | bi-LSTM (attention) | A | 0.77 (0.14) | 0.77 (0.14) | 0.77 (6.14) |
| | | | | P | 0.85 (0.09) | 0.67 (0.07) | 0.79 (0.12) |
| | | | | R | 0.85 (0.05) | 0.69 (0.14) | 0.80 (0.13) |
| | | | | F1 | 0.85 (0.07) | 0.68 (0.10) | 0.79 (0.12) |
| | | LOUO | GRU | A | 0.70 (0.21) | 0.70 (0.21) | 0.70 (0.21) |
| | | | | P | 0.91 (0.05) | 0.48 (0.11) | 0.70 (0.15) |
| | | | | R | 0.76 (0.08) | 0.67 (0.19) | 0.75 (0.11) |
| | | | | F1 | 0.83 (0.05) | 0.55 (0.12) | 0.72 (0.13) |
| Key-point Repr. Analysis | | LOUO | bi-LSTM | A | 0.73 (0.33) | 0.73 (0.33) | 0.73 (0.33) |
| | | | | P | 1.00 (0.39) | 0.01 (0.00) | 1.00 (0.40) |
| | | | | R | 0.47 (0.18) | 0.29 (0.11) | 1.00 (0.40) |
| | | | | F1 | 0.64 (0.25) | 0.02 (0.01) | 1.00 (0.40) |

In Tables 2 and 3, A, P, R, FI, K, V, ST, KT, and NP refer to Accuracy, Precision, Recall, FI score, Kinematic, Video, Suturing, Knot-tying, and Needle-passing, respectively. RMSE values are placed inside the parentheses.

Precision is a measure of the number of true-positives divided by the sum of the true-positives and the false-positives. Recall is a measure of the number of true-positives divided by the sum of true-positives and false-negatives. The F1 score represents the balance that exists between the precision and recall scores. It is defined as the product of precision and recall divided by the sum of precision and recall.

Tables 2 and 3 show that, in the example embodiment, the embedding representation (e.g., MLA 120A) analysis outperformed the previous state-of-the-art models and did so without using any kinematic data, which was required in previous work that was not robot assisted. For example, for suturing, the embedding representation analysis using LOSO had a mean (root mean square error [RMSE]) accuracy of 0.97 (0.03), a mean (RMSE) precision of 1.00 (0), a mean (RMSE) recall of 0.94 (0.08), and a mean (RMSE) F1 score of 0.97 (0.04). Using the LOUO, the embedding representation analysis had a mean (RMSE) accuracy of 0.84 (0.20), a mean (RMSE) precision of 1.00 (0), a mean (RMSE) recall of 0.88 (0.21), and a mean (RMSE) F1 score of 0.92 (0.14). The second highest-performing model on accuracy was from the study by Forestier et al, 17 with an accuracy of 0.94 (RMSE not reported). The second highest mean (RMSE) precision score (0.93 [0.01]), mean (RMSE) recall score (0.93 [0.01]), and mean (RMSE) F1 score (0.92 [0.01]) belonged to the LOSO model presented by Gao et al. 10 Overall, the embedding representation had a mean (RMSE) precision of 1.00 (0) for suturing, 0.99 (0.01) for knot tying, and 0.91 (0.11) for needle passing, resulting in a mean (RMSE) precision of 0.97 (0.01). Its mean (RMSE) recall was 0.94 (0.08) for suturing, 1.00 (0) for knot tying, and 0.99 (0.01) for needle passing, resulting in a mean (RMSE) recall of 0.98 (0.01) (Table 2). Using the LOSO scheme, it estimated scores on the Objected Structured Assessment of Technical Skill Global Rating Scale categories, with a mean (RMSE) precision of 0.85 (0.09) for novice level, 0.67 (0.07) for intermediate level, and 0.79 (0.12) for expert level, resulting in a mean (RMSE) precision of 0.77 (0.04). Its mean (RMSE) recall was 0.85 (0.05) for novice level, 0.69 (0.14) for intermediate level, and 0.80 (0.13) for expert level, resulting in a mean (RMSE) recall of 0.78 (0.03) (Table 3).

The MLAs disclosed herein also estimated scores for GRS categories when used as a regression model, with a mean (RMSE) accuracy of 0.54 (0.03) for suture handling, 0.32 (0.14) for time and motion, 0.46 (0.10) for flow of operation, 0.41 (0.12) for overall performance, and 0.51 (0.10) for quality of final product.

Table 4 illustrates the generalization potential of the MLAs (as visualized in FIGS. 2A, 2B, 6A, and 6B) to predict scores for GRS categories if it is used as regression:

TABLE 4

Predicted GRS accuracies using latent representation analysis (video data only)

| | | Surgical Skill (GRS Categories) | | | | | |
|---|---|---|---|---|---|---|---|
| Method | Model | Respect for Tissue | Suture Handling | Time and Motion | Flow of Operation | Overall Performance | Quality of Final Product |
| Latent Repr. Analysis | bi-LSTM | 0.43 | 0.54 | 0.31 | 0.46 | 0.41 | 0.51 |

Dataset 1

Based on the findings for the first dataset example compiled in Table 5, surgical procedure video data set showing the suction, stapler and trocar may yield the best predictions from MLA 120B. This is not surprising as each of these instruments has features that are unique to it in contrast to the bowel grasper and needle driver each of which are regularly mistaken for each other. The suture needle, which was the most difficult surgical instrument to segment when creating the training set, understandably may have the lowest Intersection over Union (IoU) value of any of the instruments.

It can be noted that the Bowel Grasper and Needle Driver are instruments that were most prominently featured in the Example 1 and 2 Datasets as they are amongst the most commonly used instruments in reconstruction procedures.

TABLE 5

Intersection over Union (IoU) of surgical instruments with at least one detection

| Instrument | Detections | Mean IoU - % |
|---|---|---|
| Trocar | 3 | 86.4 |
| Nathanson Retractor | 48 | 67.0 |
| Bowel Grasper | 128 | 78.6 |
| Stapler | 41 | 87.2 |
| Clip | 1 | 63.7 |
| Needle Driver | 109 | 82.7 |
| Scissors | 2 | 79.5 |
| Suture Needle | 2 | 59.0 |
| Maryland | 10 | 79.8 |
| Suction | 18 | 88.8 |
| Bougie | 8 | 84.9 |
| Endo-Close | 8 | 70.1 |
| Retractor | 13 | 86.6 |
| Overall | 391 | 71.9 |

These results indicated that the generalization capability of MLA 120B was acceptable and that not only were the per-frame segmentations possible to capture, but also extracting insights from them to construct the proposed key point mask characteristics 610 as depicted in FIG. 8.

The surgical instrument instance segmentation architecture 126 threshold was set to 0.9 to reduce the quantity of observed false positives. Some examples of correct and incorrect segmentations are presented in FIGS. 11-AA to 11-AH. FIGS. 11-AA to 11-AH illustrates examples of a predicted segmentation masks overlaid on original image, in accordance with some embodiments. FIGS. 11-AA through 11-AE consist of correctly classified and segmented instruments whereas FIGS. 11-AF through 11-AH are either incorrectly classified or segmented or both. Each image contains the original image overlaid with the predicted masks, the class prediction and associated probabilities. It is important to also consider the cases where either the mask or the associated class were incorrectly chosen. An important component of this analysis is to infer if the next step of the pipeline, the sequential relation architecture 130, is able to correctly infer temporal relations from this data and predict the correct score associated with the surgical performance video data object.

During training it was observed that the MLA 120B would quickly converge to the local minima by predicting a score of four for each of the cases. In doing so, an accuracy of 40% was achieved, as the most common score in the dataset is a score of four. It was not until wider and deeper architectures were experimented with having larger batch sizes that allowed for MLA 120B to learn of the temporal relations in this data to predict the corresponding OSATS scores.

The presence of incorrect values in the key-point matrix due to faulty detections, hardware limitations which restricted the maximum value of the hidden layers to 3375 and the inability of sequential relation architecture architectures to learn from extremely large data sequences are all possible reasons for the instability experienced during training. Tables 6 and 7 are reflective of this behaviour as the mean validation accuracies fluctuate between 0.36 and 0.45.

TABLE 6

Grid-search parameters and validation accuracies for Latent representation analysis

| | Batch | H. Dim. | Layer | Acc. (Mean/Max) |
|---|---|---|---|---|
| 1 | 5 | 500 | 2 | 0.80/1.00 |
| 2 | 5 | 1125 | 2 | 0.44/0.80 |
| 3 | 5 | 2250 | 1 | 0.83/1.00 |
| 4 | 5 | 3375 | 1 | 0.53/1.00 |
| 5 | 10 | 562 | 2 | 0.67/0.80 |
| BL | — | — | — | 0.60/0.60 |

TABLE 7

Grid-search parameters and validation accuracies for Key-point analysis

| | Batch | H. Dim. | Layer | Acc. (Mean/Max) |
|---|---|---|---|---|
| 1 | 15 | 1000 | 1 | 0.45/0.53 |
| 2 | 7 | 2250 | 1 | 0.40/0.57 |
| 3 | 15 | 500 | 2 | 0.37/0.53 |
| 4 | 30 | 562 | 1 | 0.36/0.50 |
| BL | — | — | — | 0.40/0.40 |

The model predictions and labels are plotted against each other for three chosen cases over the length of the video as depicted in FIGS. 10A-10D. FIGS. 10A-10D illustrates an example of predicted vs. annotated OSATS scores for the latent representation analysis, in accordance with some embodiments.

Dataset 2

Examples of correct and incorrect segmentations for the example 2 dataset are shown in FIGS. 11-BA-11BH. FIGS. 11-BA-11BH illustrate another example set of predicted segmentation masks overlaid on original image, in accordance with some embodiments. FIGS. 11-BA-11BD comprise correctly segmented instruments whereas FIGS. 11-BE-11BH are incorrectly segmented. Each image contains the original image overlaid with the predicted segmentation masks. It is important to also consider the cases where either the mask or the associated class were incorrectly chosen. An important component of this analysis is to infer if the next step of the pipeline, the sequential relation architecture 130, is able to correctly infer temporal relations from these data and predict the correct score associated with the clip.

The results in Tables 2 and 3 show that MLA 120A is superior to the MLA 120B for this testing. The sequential relation architecture classifiers depicted in FIGS. 2 and 6 were trained using an NVIDIA TeslaV for 6 hours for each training phase. The training times varied slightly based on the depth of the model and the chosen batch size. During training, the GRS regression model would quickly converge to the local minima by predicting a score of three for each of the cases. In doing so, an accuracy of 30% was obtained. Wider and deeper architectures, with larger batch sizes, allow the MLAs to learn temporal relations and predict the corresponding GRS scores. A two-layer sequential relation architecture with 900 hidden dimensions is used. Table 3 demonstrates the per-category mean validation accuracies for this approach fluctuate between 0.313 and 0.538.

Figure 12:
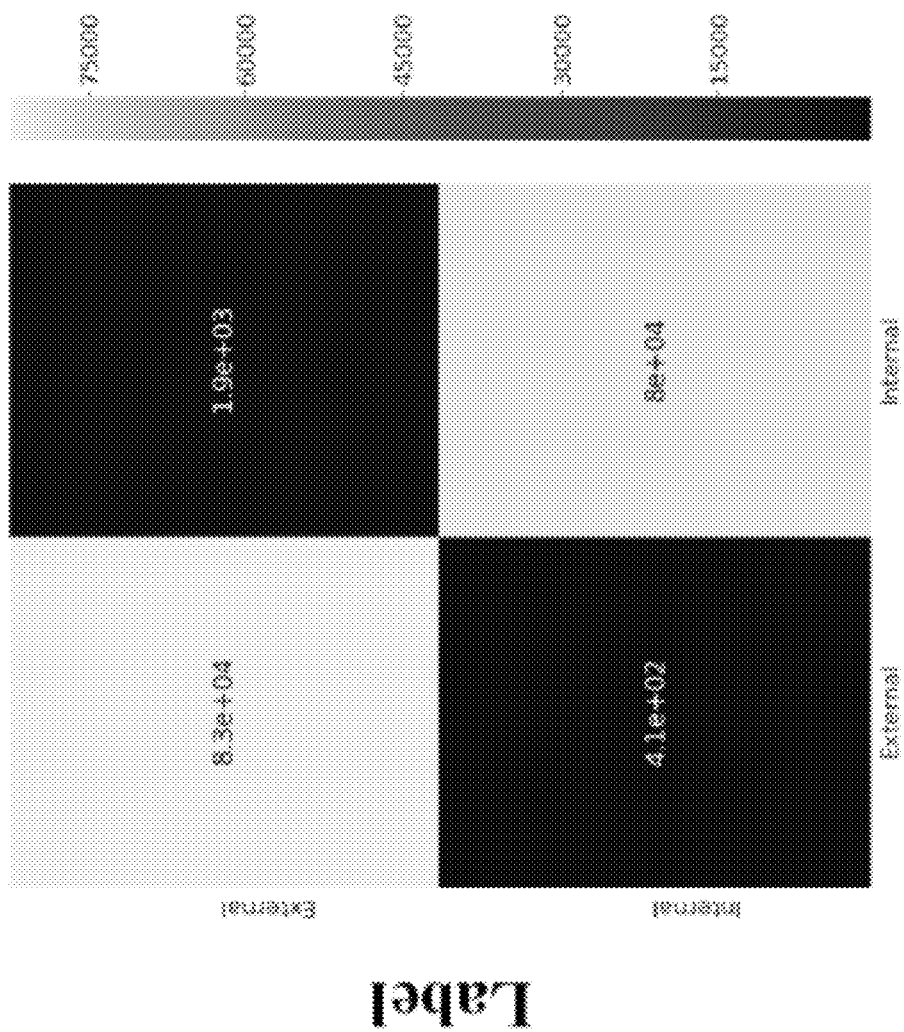
FIG. 12 illustrates an example of a confusion matrix for internal/external view classification, in accordance with some embodiments.

An external view classifier was used to eliminate external view frames for both approaches presented in this paper. The model statistics are captured in the form of a confusion matrix (see FIG. 12). FIG. 12 illustrates an example of a confusion matrix for internal/external view classification, in accordance with some embodiments.

CONCLUSION

Described above are example multiple methodologies that are aimed towards creating an end-to-end MLAs that can process a sequence of frames and assign the sequence a score out of 5 based on the Objective Structured Assessment of Technical Skills (OSATS). Each proposed MLA explores the encoding of each 1080×720 pixel frame into a representation to train a sequence-to-label model. It was found that both the MLA 120A and MLA 120B are able to capture enough information from the temporal data to infer a score that is close to the actual score. However, the MLAs can confuse certain scores such as three and four. In some embodiments, the viability of the MLAs may depend on a consensus regarding what an acceptable score should be.

Two MLAs were proposed in this disclosure for converting surgical video frames into a smaller representations that can be used to adequately train sequential relation architecture based classifiers; one being unsupervised (Latent representation analysis based on MLA 120A) and the other being supervised (Key-point representation analysis based on MLA 120B) in nature. Each MLA can be further improved to yield more promising predictions for associating surgical clips with OSATS scores. The supervised technique requires a more balanced dataset, which should theoretically yield an improvement on the average overall IoU of 72% observed in this disclosure above.

The results indicate that the proposed MLAs can infer temporal coherencies from surgical instrument motions and relate them to instrument handling. In some embodiments, the proposed MLAs can be extended to other OSATS categories, such as flow of procedure, and time and motion of instruments.

Figure 13:
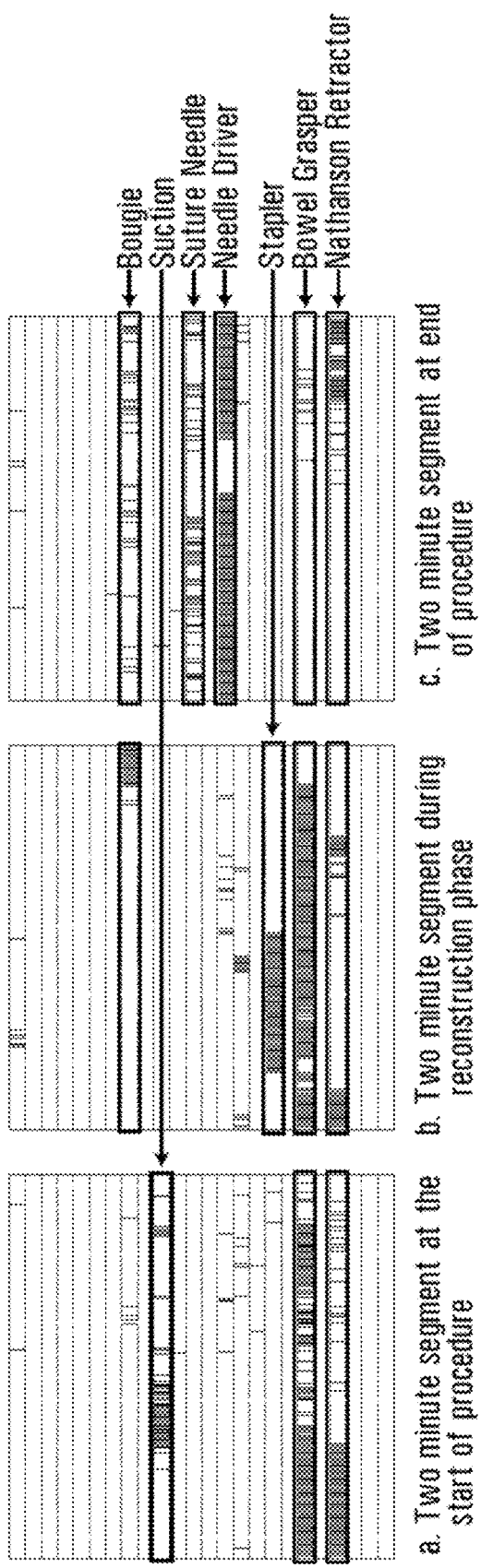
FIG. 13 illustrates an example of a visual representation of key-point feature vector, in accordance with some embodiments.

The key-point representation analysis above shoes that the detection of tools for each frame in a video has the added benefit of being able to visualize and even demark the various phases of the surgical procedure as depicted (see FIG. 13). In some embodiments, this process may be extended to use key-point analysis and extend it to surgical phase or task detection.

FIG. 13 illustrates an example of a visual representation of key-point feature vector 610, in accordance with some embodiments. The vector is for 2-minute clips during the procedure. Each row corresponds to an instrument and the demarcations within these rows indicate the presence of tools.

Figure 14:
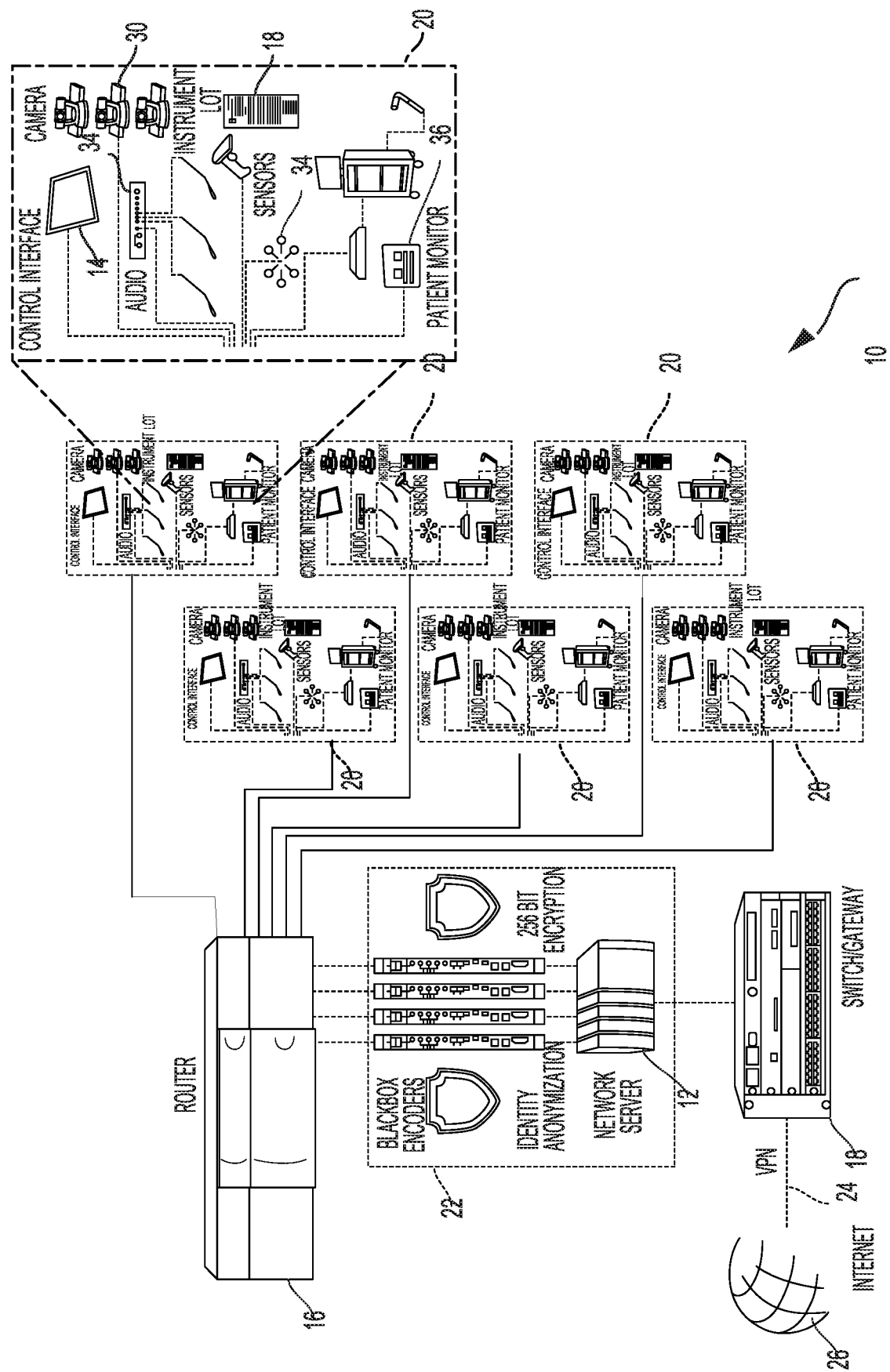
FIG. 14 illustrates a schematic of an architectural platform for data collection in a live OR setting or patient intervention area, in accordance with some embodiments.

FIG. 14 illustrates a schematic of an architectural platform 10 for data collection in a live operating room setting or patient intervention area, in accordance with some embodiments. Further details regarding data collection and analysis are provided in International (PCT) Patent Application No. PCT/CA2016/000081 entitled "OPERATING ROOM BLACK-BOX DEVICE, SYSTEM, METHOD AND COMPUTER READABLE MEDIUM FOR EVENT AND ERROR PREDICTION" and filed Mar. 26, 2016 and International (PCT) Patent Application No. PCT/CA2015/000504, entitled "OPERATING ROOM BLACK-BOX DEVICE, SYSTEM, METHOD AND COMPUTER READABLE MEDIUM" and filed Sep. 23, 2015, the entire contents of each of which is hereby incorporated by reference.

The data collected relating to the handwashing activity and be correlated and/or synchronized with other data collected from the live OR setting by the platform 10. For example, hand washing activity for a particular individual participating in a surgery can be linked and/or synchronized with other data collected from the live OR setting for the surgery. This can also include data post-surgery, such as data related to the outcome of the surgery.

The platform 10 can collect raw video data for processing in order to detect surgical tool usage and/or technical performance, and performance measurement. The output data (surgical tool usage and/or technical performance tracking and performance measurement) can be aggregated with other data collected from the live OR setting for the surgery or otherwise generated by platform 10 for analytics.

The platform 10 can collect raw video data for processing in order to track and measure surgical tools and/or technical performance as described herein. The output data (e.g., performance measurement and/or alerts) can be aggregated with other data collected from the live OR setting for surgery or otherwise generated by platform 10 for analytics.

The platform 10 includes various hardware components such as a network communication server 12 (also "network server") and a network control interface 14 (including monitor, keyboard, touch interface, tablet, processor and storage device, web browser) for on-site private network administration.

Multiple processors may be configured with operating system and client software (e.g., Linux, Unix, Windows Server, or equivalent), scheduling software, backup software. Data storage devices may be connected on a storage area network.

The platform 10 can include a surgical or medical data encoder 22. The encoder may be referred to herein as a data recorder, a "black-box" recorder, a "black-box" encoder, and so on. The platform 10 may also have physical and logical security to prevent unintended or unapproved access. A network and signal router 16 connects components.

The platform 10 includes hardware units 20 that include a collection or group of data capture devices for capturing and generating medical or surgical data feeds for provision to encoder 22. The hardware units 20 may include cameras 30 (e.g., including cameras for capturing video for surgical tool tracking and/or technical performance, and performance measurement) internal to patient to capture video data for provision to encoder 22. The encoder 22 can implement the surgical tool and/or technical performance tracking, and performance measurement described herein in some embodiments. The video feed may be referred to as medical or surgical data. An example camera 30 is a laparoscopic or procedural view camera resident in the surgical unit, ICU, emergency unit or clinical intervention units. Example video hardware includes a distribution amplifier for signal splitting of Laparoscopic cameras. The hardware units 20 can have audio devices 32 mounted within the surgical unit, ICU, emergency unit or clinical intervention units to provide audio feeds as another example of medical or surgical data. Example sensors 34 installed or utilized in a surgical unit, ICU, emergency unit or clinical intervention units include but not limited to: environmental sensors (e.g., temperature, moisture, humidity, etc., acoustic sensors (e.g., ambient noise, decibel), electrical sensors (e.g., hall, magnetic, current, mems, capacitive, resistance), flow sensors (e.g., air, fluid, gas) angle/positional/displacement sensors (e.g., gyroscopes, altitude indicator, piezoelectric, photoelectric), and other sensor types (e.g., strain, level sensors, load cells, motion, pressure). The sensors 34 provide sensor data as another example of medical or surgical data. The hardware units 20 also include patient monitoring devices 36 and an instrument lot 18.

The customizable control interface 14 and GUI (may include tablet devices, PDA's, hybrid devices, convertibles, etc.) may be used to control configuration for hardware components of unit 20. The platform 10 has middleware and hardware for device-to-device translation and connection and synchronization on a private VLAN or other network. The computing device may be configured with anonymization software, data encryption software, lossless video and data compression software, voice distortion software, transcription software. The network hardware may include cables such as Ethernet, RJ45, optical fiber, SDI, HDMI, coaxial, DVI, component audio, component video, and so on to support wired connectivity between components. The network hardware may also have wireless base stations to support wireless connectivity between components.

The platform 10 can include anonymization software for anonymizing and protecting the identity of all medical professionals, patients, distinguishing objects or features in a medical, clinical or emergency unit. This software implements methods and techniques to detect facial, distinguishing objects, or features in a medical, clinical or emergency unit and distort/blur the image of the distinguishing element. The extent of the distortion/blur is limited to a localized area, frame by frame, to the point where identity is protected without limiting the quality of the analytics. The software can be used for anonymizing hand washing activity video data as well.

Data encryption software may execute to encrypt computer data in such a way that it cannot be recovered without access to the key. The content may be encrypted at source as individual streams of data or encrypted as a comprehensive container file for purposes of storage on an electronic medium (i.e., computer, storage system, electronic device) and/or transmission over Internet 26. Encrypt/decrypt keys may either be embedded in the container file and accessible through a master key, or transmitted separately.

Lossless video and data compression software executes with a class of data compression techniques that allows the original data to be perfectly or near perfectly reconstructed from the compressed data.

Device middleware and hardware may be provided for translating, connecting, formatting and synchronizing of independent digital data streams from source devices. The platform 10 may include hardware, software, algorithms and methods for the purpose of establishing a secure and reliable connection and communication directly, or indirectly (via router, wireless base station), with the OR encoder 22, and third-party devices (open or proprietary) used in a surgical unit, ICU, emergency or other clinical intervention unit.

The hardware and middleware may assure data conformity, formatting and accurate synchronization. Synchronization may be attained by utilizing networking protocols for clock synchronization between computer systems and electronics devices over packet-switched networks like NTP, etc.

The encoder 22 can implement the surgical tool and/or technical performance tracking and performance measurement described herein in some embodiments. The encoder 22 can provide video data and other data to another server for surgical tool and/or technical performance tracking and performance measurement described herein in some embodiments. The OR or Surgical encoder (e.g., encoder 22) may be a multi-channel encoding device that records, integrates, ingests and/or synchronizes independent streams of audio, video, and digital data (quantitative, semi-quantitative, and qualitative data feeds) into a single digital container. The digital data may be ingested into the encoder as streams of metadata and is sourced from an array of potential sensor types and third-party devices (open or proprietary) that are used in surgical, ICU, emergency or other clinical intervention units. These sensors and devices may be connected through middleware and/or hardware devices which may act to translate, format and/or synchronize live streams of data from respected sources.

The Control Interface (e.g., 14) may include a Central control station (non-limiting examples being one or more computers, tablets, PDA's, hybrids, and/or convertibles, etc.) which may be located in the clinical unit or another customer designated location. The Customizable Control Interface and GUI may contain a customizable graphical user interface (GUI) that provides a simple, user friendly and functional control of the system.

The encoder 22 may be responsible for synchronizing all feeds, encoding them into a signal transport file using lossless audio/video/data compression software. Upon completion of the recording, the container file will be securely encrypted. Encrypt/decrypt keys may either be embedded in the container file and accessible through a master key, or transmitted separately. The encrypted file may either be stored on the encoder 22 or stored on a Storage area network until scheduled transmission.

According to some embodiments, this information then may be synchronized (e.g., by the encoder 22) and/or used to evaluate: technical performance of the healthcare providers; non-technical performance of the clinical team members; patient safety (through number of registered loss and/or adverse events); occupational safety; workflow; visual and/or noise distractions; and/or interaction between medical/surgical devices and/or healthcare professionals, etc. According to some embodiments, this may be achieved by using objective structured assessment tools and questionnaires and/or by retrieving one or more continuous data streams from sensors 34, audio devices 32, an anesthesia device, medical/surgical devices, implants, hospital patient administrative systems (electronic patient records), or other data capture devices of hardware unit 20. According to some embodiments, significant "events" may be detected, tagged, time-stamped and/or recorded as a time-point on a timeline that represents the entire duration of the procedure and/or clinical encounter. The timeline may overlay captured and processed data to tag the data with the time-points. In some embodiments, the events may be surgical tool and/or technical performance tracking events or episodes.

Upon completion of data processing and analysis, one or more such events (and potentially all events) may be viewed on a single timeline represented in a GUI, for example, to allow an assessor to: (i) identify event clusters; (ii) analyze correlations between two or more registered parameters (and potentially between all of the registered parameters); (iii) identify underlying factors and/or patterns of events that lead up to adverse outcome; (iv) develop predictive models for one or more key steps of an intervention (which may be referred to herein as "hazard zones") that may be statistically correlated to loss/adverse event/adverse outcomes, v) identify a relationship between performance outcomes and clinical costs. These are non-limiting examples of uses an assessor may make of a timeline presented by the GUI representing recorded events.

Analyzing these underlying factors according to some embodiments may allow one or more of: (i) proactive monitoring of clinical performance; and/or (ii) monitoring of performance of healthcare technology/devices (iii) creation of educational interventions—e.g., individualized structured feedback (or coaching), simulation-based crisis scenarios, virtual-reality training programs, curricula for certification/ re-certification of healthcare practitioners and institutions; and/or identify safety/performance deficiencies of medical/surgical devices and develop recommendations for improvement and/or design of "intelligent" devices and implants—to curb the rate of risk factors in future procedures and/or ultimately to improve patient safety outcomes and clinical costs.

The device, system, method and non-transitory computer readable medium according to some embodiments, may combine capture and synchronization, and secure transport of video/audio/metadata with rigorous data analysis to achieve/demonstrate certain values. The device, system, method and non-transitory computer readable medium according to some embodiments may combine multiple inputs, enabling recreation of a full picture of what takes place in a clinical area, in a synchronized manner, enabling analysis and/or correlation of these factors (between factors and with external outcome parameters (clinical and economical). The system may bring together analysis tools and/or processes and using this approach for one or more purposes, examples of which are provided herein.

Beyond development of a data platform 10, some embodiments may also include comprehensive data collection and/or analysis techniques that evaluate multiple aspects of any procedure including video data internal to the patient for surgical tool usage and/or technical performance tracking, and performance measurement. One or more aspects of embodiments may include recording and analysis of video, audio and metadata feeds in a synchronized fashion. The data platform 10 may be a modular system and not limited in terms of data feeds—any measurable parameter in the OR/patient intervention areas (e.g., data captured by various environmental acoustic, electrical, flow, angle/positional/displacement and other sensors, wearable technology video/data stream, etc.) may be added to the data platform 10. One or more aspects of embodiments may include analyzing data using validated rating tools which may look at different aspects of a clinical intervention.

According to some embodiments, all video feeds and audio feeds may be recorded and synchronized for an entire medical procedure. Without video, audio and data feeds being synchronized, rating tools designed to measure the technical skill and/or non-technical skill during the medical procedure may not be able to gather useful data on the mechanisms leading to adverse events/outcomes and establish correlation between performance and clinical outcomes.

According to some embodiments, measurements taken (e.g., loss rates, number of adverse events, individual/team/technology performance parameters) may be collected in a cohesive manner. According to some embodiments, data analysis may establish correlations between all registered parameters if/as appropriate. With these correlations, hazard zones may be pinpointed, high-stakes assessment programs may be developed and/or educational interventions may be designed.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, numerous references will be made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

Although the embodiments have been described in detail, it should be understood that various changes, substitutions and alterations can be made herein.

Moreover, the scope of the present application is not intended to be limited to the particular embodiments of the process, machine, manufacture, composition of matter, means, methods and steps described in the specification.

As can be understood, the examples described above and illustrated are intended to be exemplary only.

What is claimed is:

1. A system for training a machine learning architecture for surgical performance tracking and measurement, the system comprising:

at least one memory storing the machine learning architecture for estimating a value related to surgical instrument motion, the machine learning architecture defined by a plurality of parameters representative of a sequential relation architecture and a dimensionality reduction architecture;

at least one processor in communication with the at least one memory, the at least one processor configured to:

receive a first data set comprising one or more surgical procedure video data sets comprising a plurality of frames, the plurality of frames comprising at least one surgical instrument, and label data for each of the one or more surgical procedure video data sets representative of surgical performance;

train the machine learning architecture based on the first data set by:

for each surgical procedure video data set in the first data set:

processing each frame in the respective plurality of frames of the respective surgical procedure video data set with the plurality of parameters representative of the dimensionality reduction architecture to generate a compressed frame incorporating surgical instrument characteristics in the respective frame;

for each compressed frame generated by the plurality of parameters representative of the dimensionality reduction architecture:

processing each compressed frame with the plurality of parameters representative of the sequential relation architecture to generate the value related to surgical instrument motion;

updating the plurality of parameters representative of the sequential relation architecture based on a loss value, the loss value based on a comparison of the respective label and the generated value related to surgical instrument motion; and store the trained machine learning architecture in the at least one memory.

2. The system of claim 1, the at least one processor further configured to:

train the machine learning architecture based on the first data set by:

for each surgical procedure video data set in the first data set:

processing each frame in the respective plurality of frames of the respective surgical procedure video data set with a first portion the plurality of parameters representative of the dimensionality reduction architecture to generate a compressed frame incorporating surgical instrument characteristics in the respective frame;

processing the generated compressed frame in the respective surgical procedure video data set with a second portion the plurality of parameters representative of the dimensionality reduction architecture to generate a reconstructed frame;

updating the plurality of parameters representative of the dimensionality reduction architecture based on a reconstruction loss comparing each frame and the respective reconstructed frame.

3. The system of claim 2, wherein the reconstruction loss is based on a comparison of each frame and the respective reconstructed frame on a pixel level.

4. The system of claim 1, wherein a size of each compressed frame is based on a processing capacity of the processor to process the compressed frame with the plurality of parameters representative of the sequential relation architecture.

5. The system of claim 1, wherein the respective label comprises ratings score for surgical performance, and the value related to surgical instrument motion is a predicted ratings score.

6. The system of claim 1, wherein the plurality of parameters representative of the dimensionality reduction architecture comprise a plurality of parameters representative of a convolutional layer, a pooling layer, and an activation layer.

7. The system of claim 1, wherein the plurality of parameters representative of the dimensionality reduction architecture comprise a plurality of parameters representative of:

a first convolutional layer connected to a first activation layer for successively compressing a part of each frame in the respective plurality of frames in the respective surgical procedure video data set into a partially compressed frame kernel;

a second convolutional layer receiving the partially compressed frame kernel and connected to a second activation layer for processing each the partially compressed frame kernel in the respective frame into a further partially compressed frame kernel;

a pooling layer for extracting a respective partial feature from each further partially compressed frame kernel;

wherein the respective partial features of the respective frame are processed into the compressed frame;

a third convolutional layer connected to a third activation layer for successively decompressing a part of each compressed frame into a partially decompressed frame kernel;

a fourth convolutional layer connected to a fourth activation layer for successively decompressing the partially decompressed frame kernel of each compressed frame into a further partially decompressed frame kernel;

a fifth convolutional layer connected to a fifth activation layer for successively decompressing the further partially decompressed frame;

wherein the respective further partially decompressed frame of the respective frame are processed into a reconstructed representation of the respective frame; and wherein the reconstruction loss is based on a comparison of the respective frame and the reconstructed representation of the respective frame.

8. The system of claim 7, wherein the first activation layer, second activation layer, third activation layer, and fourth activation layer are ReLu activation layers, and the fifth activation layer is a Tan h activation layer, and the first convolutional layer and second convolutional layer are 2D convolution layers, and the third convolutional layer, fourth convolutional layer, and fifth convolutional layer are 2D de-convolution layers.

9. The system of claim 1, wherein the respective label comprises a classification of a surgical action in the respective surgical procedure video data set, and the value related to surgical instrument motion is a predicted surgical action.

10. The system of claim 1, wherein the respective label comprises a classification of a surgical skill in the respective surgical procedure video data set, and the value related to surgical instrument motion is a predicted surgical skill.

11. A system for a machine learning architecture for surgical performance tracking and measurement, the system comprising:

at least one memory storing the machine learning architecture for estimating a value related to surgical instrument motion, the machine learning architecture defined by a plurality of parameters representative of a surgical instrument instance segmentation architecture, a decomposition model, and a sequential relation architecture;

at least one processor in communication with the at least one memory, the at least one processor configured to:

receive a first data set comprising one or more surgical procedure video data sets comprising a plurality of frames, the plurality of frames comprising at least one surgical instrument, and label data for each of the one or more surgical procedure video data sets;

train the machine learning architecture based on the first data set by:

for each surgical procedure video data set in the first data set:

processing each frame in the respective plurality of frames in the respective surgical procedure video data set with the plurality of parameters representative of the surgical instrument instance segmentation architecture to assign each pixel in the respective frame a likelihood of belonging to at least one surgical instrument to generate a respective mask for each surgical instrument in the respective frame;

processing each of the generated masks within the respective frames with the plurality of parameters representative of the decomposition model to generate key point mask characteristics based on extracting surgical instrument characteristics from each mask in the respective frame;

processing each of the key point mask characteristics in each frame with the plurality of parameters representative of the sequential relation architecture to generate the value related to surgical instrument motion;

updating the plurality of parameters based on a loss value, the loss value based on a comparison of the respective label and the value related to surgical instrument motion; and store the trained machine learning architecture in the at least one memory.

12. The system of claim 11, wherein the decomposition model extracts surgical instrument characteristics to generate key point mask characteristics based on:

determining a covariance matrix for each mask;

decomposing the covariance matrix into eigenvectors to determine a first eigenvector for each mask in the respective frame corresponding to a direction of a largest variance within the mask; and incorporating a mask orientation characteristic based on the first eigenvector for each mask into the key point mask characteristics to define surgical instrument characteristics for each mask.

13. The system of claim 11, wherein the decomposition model extracts surgical instrument characteristics to generate key point mask characteristics based on:

determining a centroid mask characteristic based on a contour of the mask to define surgical instrument characteristics for each mask.

14. The system of claim 11, wherein the key point mask characteristics are a fixed-length vector representative of one or more geometric properties of each mask in the respective frame.

15. The system of claim 11, wherein the respective label comprises a rating scale score indicative of surgical performance within the one or more surgical procedure video data sets, and the value related to surgical instrument motion is a predicted rating scale score.

16. The system of claim 11, wherein the respective label comprises a classification of a surgical action in the respective surgical procedure video data set, and the value related to surgical instrument motion is a predicted surgical action.

17. The system of claim 11, wherein the respective label comprises a classification of a surgical skill in the respective surgical procedure video data set, and the value related to surgical instrument motion is a predicted surgical skill.

18. The system of claim 11, wherein the plurality of parameters representative of the feature detector model comprises a plurality of parameters representative of a pre-trained mask generator architecture.

19. The system of claim 18, wherein the plurality of parameters representative of the pre-trained mask generator architecture are configured to include a final layer modified to represent surgical instrument classifications.

20. A non-transitory computer readable medium storing machine interpretable instructions, which when executed, cause one or more processors to perform one or more steps corresponding to a method comprising:

receiving a first data set comprising one or more surgical procedure video data sets comprising a plurality of frames, the plurality of frames comprising at least one surgical instrument, and label data for each of the one or more surgical procedure video data sets;

training a machine learning architecture for estimating a value related to surgical instrument motion, the machine learning architecture defined by a plurality of parameters representative of a surgical instrument instance segmentation architecture, a decomposition model, and a sequential relation architecture by;

for each surgical procedure video data set in the first data set:

processing each frame in the respective plurality of frames in the respective surgical procedure video data set with the plurality of parameters representative of the surgical instrument instance segmentation architecture to assign each pixel in the respective frame a likelihood of belonging to at least one surgical instrument to generate a respective mask for each surgical instrument in the respective frame;

processing each of the masks within the respective frames with the plurality of parameters representative of the decomposition model to generate key point mask characteristics based on extracting surgical instrument characteristics for each mask in the respective frame;

processing the key point mask characteristics in each frame with the plurality of parameters representative of the sequential relation architecture to generate the value related to surgical instrument motion;

updating the plurality of parameters based on a loss value, the loss value based on a comparison of the respective label and the value related to surgical instrument motion; and storing the trained machine learning architecture in a memory.

* * * * *